US011084847B2

(12) United States Patent
Cai et al.

(10) Patent No.: US 11,084,847 B2
(45) Date of Patent: Aug. 10, 2021

(54) POLYAMIDE COMPOUND AND USE THEREOF

(71) Applicant: SICHUAN KELUN-BIOTECH BIOPHARMACEUTICAL CO., LTD., Chengdu (CN)

(72) Inventors: Jiaqiang Cai, Chengdu (CN); Qiang Tian, Chengdu (CN); Mingliang Zhao, Chengdu (CN); Hong Zeng, Chengdu (CN); Hongmei Song, Chengdu (CN); Nan Yu, Wenjiang (CN); Hua Deng, Chengdu (CN); Wei Zhong, Chengdu (CN); Long Yang, Chengdu (CN); Lei Wu, Chengdu (CN); Haitao Huang, Chengdu (CN); Yongyong Wu, Chengdu (CN); Donghai Su, Chengdu (CN); Xin Zhou, Chengdu (CN); Yuting Tan, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 0 days.

(21) Appl. No.: 16/321,430

(22) PCT Filed: Sep. 22, 2017

(86) PCT No.: PCT/CN2017/103027
§ 371 (c)(1),
(2) Date: Jan. 28, 2019

(87) PCT Pub. No.: WO2018/059331
PCT Pub. Date: Apr. 5, 2018

(65) Prior Publication Data
US 2020/0109166 A1 Apr. 9, 2020

Related U.S. Application Data

(63) Continuation of application No. PCT/CN2017/103027, filed on Sep. 22, 2017.

(30) Foreign Application Priority Data

Sep. 27, 2016 (CN) .......................... 201610852604.8

(51) Int. Cl.
*C07K 5/107* (2006.01)
*A61P 23/00* (2006.01)
*A61K 38/00* (2006.01)

(52) U.S. Cl.
CPC ............ *C07K 5/1016* (2013.01); *A61P 23/00* (2018.01); *A61K 38/00* (2013.01)

(58) Field of Classification Search
None
See application file for complete search history.

(56) References Cited

U.S. PATENT DOCUMENTS

| 8,906,859 B2* | 12/2014 | Schteingart ............. A61P 35/00 514/18.4 |
|---|---|---|
| 2004/0010014 A1 | 1/2004 | Breslin et al. |
| 2004/0142379 A1 | 7/2004 | Hilaire et al. |
| 2011/0212882 A1 | 9/2011 | Schteingart et al. |
| 2017/0007574 A1 | 1/2017 | Spencer et al. |
| 2017/0183307 A1 | 6/2017 | Murayama et al. |
| 2018/0078605 A1 | 3/2018 | Spencer et al. |
| 2018/0282369 A1 | 10/2018 | Desai et al. |
| 2019/0144499 A1 | 5/2019 | Li et al. |

FOREIGN PATENT DOCUMENTS

| CN | 1665501 A | 9/2005 |
|---|---|---|
| CN | 101535336 A | 9/2009 |
| CN | 101627049 B | 9/2012 |

(Continued)

OTHER PUBLICATIONS

Beck et al., Therapeutic Potential of Kappa Opioid Agonists. Pharmaceuticals, 2019, 12, p. 1-13.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Roberts et al., Chemistry for peptide and protein PEGylation. Advanced Drug Delivery Reviews, 2012, 64, 116-127.*
Japanese Office Action dated Aug. 4, 2020, for Patent Application No. 2019-504693, filed Jan. 28, 2019, 6 pages. (English translation attached).
Chinese (First) Office Action and Search Report dated May 8, 2020, for Patent Application No. 2017800468206, filed Jan. 28, 2019, eighteen pages. (English translation attached).

(Continued)

*Primary Examiner* — Po-Chih Chen
(74) *Attorney, Agent, or Firm* — Morrison & Foerster LLP

(57) ABSTRACT

The invention relates to a polyamide compound and a use thereof. Specifically, the invention relates to a type of polyamide compound (which preferably comprise one or more amide bonds formed by condensation of same or different L-amino acids or D-amino acids), or stereoisomers, crystalline polymorphs, solvates, metabolites, prodrugs or pharmaceutically acceptable salts or esters thereof, or pharmaceutical compositions thereof, as well as a method for preparing the polyamide compound and a use thereof in the prevention or treatment of diseases associated with κ-opioid receptor. The polyamide compound of the invention has excellent κ-opioid receptor agonistic activity and hydrophilicity, thus having a lesser ability of penetrating the blood-brain barrier and a lower capacity for entering the brain. The compound of the invention has higher selectivity for a κ-opioid receptor, lower addictiveness, improved pharmacokinetic properties, and improved safety (lower toxicity and/or fewer side effects), good patient compliance, and/or lesser propensity for developing tolerance, among other excellent medicinal properties.

42 Claims, No Drawings

(56) References Cited

FOREIGN PATENT DOCUMENTS

| | | | |
|---|---|---|---|
| CN | 107098871 A | 8/2017 | |
| JP | 5244810 B2 | 7/2013 | |
| JP | 2018-516894 A | 6/2018 | |
| JP | 2019-517530 A | 6/2019 | |
| TW | 201601743 A | 1/2016 | |
| WO | WO-1999/32510 A1 | 7/1999 | |
| WO | WO-2003/092688 A2 | 11/2003 | |
| WO | WO-2008/057608 A2 | 5/2008 | |
| WO | WO-2008/060552 A2 | 5/2008 | |
| WO | WO-2013/184794 A2 | 12/2013 | |
| WO | WO-2015/065867 A2 | 5/2015 | |
| WO | WO-2016/073443 A2 | 5/2016 | |
| WO | WO-2017/211272 A1 | 12/2017 | |

OTHER PUBLICATIONS

European Extended Search Report dated Apr. 24, 2020, for Patent Application No. 17854781.6, filed Sep. 22, 2017, eight pages.

Baldrick, P. (2000). "Pharmaceutical Excipient Development: The Need for Preclinical Guidance," Regulatory Toxicology and Pharmacology 32:210-218.

Chiswell, D.J. et al. (Mar. 1992). "Phage Antibodies: Will New 'Coliclonal' Antibodies Replace Monoclonal Antibodies?", Trend Biotechnol. 10(3):80-84.

Davidson, B.L. (Mar. 1993). "A Model System for In Vivo Gene Transfer into the Central Nervous System using an Adenoviral Vector," Nature Genetics 3(3):219-223.

Dutta, A.S. et al. (2000). "Potent Cyclic Monomeric and Dimeric Peptide Inhibitors of VLA-4 (α4 β1 Integrin)-Mediated Cell Adhesion Based on the Ile-Leu-Asp-Val Tetrapeptide", J. Peptide Sci. 6(7):321-341.

Grosschedl, R. et al. (Jul. 1985). "Cell-Type Specificity of Immunoglobulin Gene Expression is Regulated by at Least Three DNA Sequence Elements," Cell. 41(3):885-897.

Huse, W.D. et al. (Dec. 8, 1989). "Generation of a Large Combinatorial Library of the Immunoglobulin Repertoire in Phage Lambda," Science 246(4935):1275-1281.

Killen, J.A. et al. (Nov. 1984). "Specific Killing of Lymphocytes that Cause Experimental Autoimmune Myasthenia Gravis by Ricin Toxin-Acetylcholine Receptor Conjugates", J Immunol. 133(5):2549-2553.

Kozbor, D. et al. (Mar. 1993). "The Production of Monoclonal Antibodies from Human Lymphocytes", Immunol. Today 4(3):72-79.

Le Gal La Salle, G. et al. (Feb. 12, 1993). "An Adenovirus Vector for Gene Transfer into Neurons and Glia in the Brain", Science 259(5097):988-990.

Scott, J.K. (Jul. 1992). "Discovering Peptide Ligands Using Epitope Libraries", Trends Biochem Sci. 17(7):241-245.

Wang, W. (Aug. 2000). "Lyophilization and Development of Solid Protein Pharmaceuticals", Int. J. Pharm. 203(1-2):1-60.

Auh, Q.-S. et al. (Aug. 30, 2012; e-pub. Jul. 20, 2012). "Effects of Peripheral $_\kappa$ Opioid Receptor Activation on Inflammatory Mechanical Hyperalgesia in Male and Female Rats," Neuroscience Letters 524(2):111-115.

Barber, A. et al. (1994). "A Pharmacological Profile of the Novel, Peripherally-Selective k-opioid Receptor Agonist, EMD 61753," Br. J. Pharmacol 113:1317-1327.

Camilleri, M. (Sep. 2008). "Novel pharmacology: Asimadoline, a k-opioid Agonist, and Visceral Sensation," Neurogastroenterology and Motility 20(9):971-979.

Clark, C.R. et al. (1988). "Highly Selective $_\kappa$ Opioid Analgesics. Synthesis and Structure-Activity Relationships of Novel N-[(2-Aminocyclohexyl)aryl]acetamide and N-[(2-Aminocyclohexyl)aryloxy]acetamide Derivatives," J. Med. Chem. 31(4):831-836.

Cunha, T.M. et al. (2012). "Stimulation of Peripheral Kappa Opioid Receptors Inhibits Inflammatory Hyperalgesia Via Activation of the PI3Kγ/AKT/nNOS/NO Signaling Pathway," Molecular Pain 8(10):1-8.

Persson, T. et al. (2002). "Specific Granules of Human Eosinophils Have Lysosomal Characteristics: Presence of Lysosome-Associated Membrane Proteins and Acidification upon Cellular Activation," Bio Biophys Res Comm. 291(4):844-854.

Japanese Office Action dated Mar. 10, 2020, for Patent Application No. 2019-504693, filed Jan. 28, 2019, 10 pages. (English translation attached).

* cited by examiner

POLYAMIDE COMPOUND AND USE THEREOF

CROSS REFERENCE TO RELATED APPLICATIONS

This application is the National Stage filing of PCT/CN2017/103027 entitled POLYAMIDE COMPOUND AND USE THEREOF with the International Filing Date of Sep. 22, 2017 which claims priority to Chinese application 201610852604.8 filed on Sep. 27, 2016.

TECHNICAL FIELD

The invention relates to medicinal field, particularly relates to a polyamide compound (preferably a compound containing one or more amide bonds formed by condensation of same or different L-amino acids or D-amino acids), a pharmaceutical composition comprising the compound, and use thereof for the prevention or treatment of a disease associated with κ-opioid receptor.

BACKGROUND ART

Opioid receptors (μ, δ and κ) are widely distributed in the central nervous system and the peripheral nervous system. Traditional opioid receptor agonists (such as morphine and derivatives thereof) are the most effective drugs for treating chronic arthritis, inflammatory neuralgia, post-surgery pain and moderate to severe pain caused by various cancers. However, systemic administration can result in side effects such as respiratory depression, drug addiction, constipation, nausea, confusion, and tolerance. Unlike μ-opioid receptor agonists, κ-opioid receptor agonists will not cause respiratory depression and constipation, and some studies have shown that κ-opioid receptor agonists are less addictive (Clark C, Halfpenny P, Hill R et al., J. Med. Chem., 1988, 31, 831-836). By peripheral administration of a low dose of a κ-opioid receptor agonist directly to the infected part, it does not generate a systemic response, thus avoiding undesirable symptoms such as sedation and anxiety. Peripheral administration of an opioid receptor agonist to an organism under normal conditions has no analgesic effect, however, when there is inflammation or tissue damage, the function of peripheral opioid receptors is enhanced, and opioid receptor agonists exert an analgesic effect (Persson T, Calafat J, Janssen H et al., Biochem. Biophys. Res. Commun., 2002, 291, 844-854). In addition, it is not easy for the organism to develop tolerance to κ-opioid receptor agonists (Stein A, Helmke K, Szopko C et al., Dtsch. Med. Wochenschr., 1996, 121, 255).

Auh and Ro et al. injected complete Freund's adjuvant (CFA) into the plantar surface of the right hind paws of SD rats to cause hyperalgesia, followed by an injection of three concentrations of U50488 (a specific κ-opioid receptor agonist) 3 days later. The research result showed: peripheral administration of a κ-opioid receptor agonist could significantly alleviate pain and hyperalgesia, and the gender difference in anti-hyperalgesia is more significant at a high dose. This result was further confirmed in clinical pain models (Auh Q S, Ro J Y. Neurosci. Lett., 2012, 524, 111-115). It is reported that activation of κ-opioid receptors can inhibit inflammatory hyperalgesia, and the likely mechanism may be stimulation of PI3Kγ/AKT signaling through nNOS/NO pathway (Cunha T M, Souza G R, Domingues A C et al., Mol. Pain, 2012, 8, 10).

The first-generation of κ-opioid receptor agonists include spiradoline and enadoline, which can enter the brain after oral administration. Although these drugs have less side effects than morphine at an effective dose, their further development is stopped due to side effects such as dysphoria and hallucination. The second-generation of κ-opioid receptor agonists (such as asimadoline) have similar chemical structure to the first-generation of κ-opioid receptor agonists but a higher peripheral selectivity (Barber A, Bartoszyk G, Bender H et al, Br. J. Pharmacol. 1994, 113, 1317-1327). However, due to their poor anesthetic effect at an allowed dose, the development as opioid narcotics has been abandoned, instead, they are developed as drugs for treating digestive diseases such as irritable bowel syndrome (Camilleri M. Neurogastroenterol. Motil., 2008, 20, 971-979).

CN 101627049 B discloses a type of synthetic peptide amides having a polypeptide chain, which can be used as ligands of κ-opioid receptors. It still needs further study for its druggability.

Although there are some κ-opioid receptor agonists in the prior art, still there is a need for a novel κ-opioid receptor agonist with improved activity and/or druggability.

Contents of Invention

Through intensive research and creative work, the inventor of the present application obtains a type of novel compound containing amide bond, which has not only an excellent κ-opioid receptor agonistic activity (high affinity for κ-opioid receptor), but also a very high hydrophilic ability and thus a lesser ability of penetrating the blood-brain barrier and a lower capacity of entering the brain. In some preferred embodiments, the compound of the invention also has a higher selectivity for κ-opioid receptor over μ and δ-opioid receptors (the $EC_{50}$ for μ and δ-opioid receptor may be at least 10-fold, preferably at least 100-fold, and particularly preferably at least 1000-fold higher than the $EC_{50}$ for κ-opioid receptor), lower addictiveness, better physiochemical properties (e.g. solubility, physical and/or chemical stability), improved pharmacokinetic properties (e.g. lower inhibition of cytochrome $P_{450}$ isoenzymes, improved bioavailability, appropriate half-life and duration of action), improved safety (lower toxicity and/or fewer side effects (such as side effects of the central nervous system, respiratory depression, sedation, hallucination, antidiuresis, nausea, vomiting, constipation, and dependence)), good patient compliance, and/or lesser propensity for developing tolerance, among other excellent medicinal properties.

In an aspect, the invention provides a compound, or a stereoisomer, a crystalline polymorph, a solvate, a metabolite, a prodrug or a pharmaceutically acceptable salt or ester thereof, wherein the compound has a structure of Formula (I):

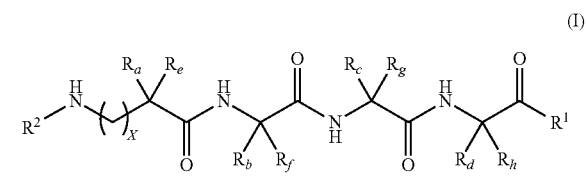

wherein:

X is an integer selected from 0-6;

$R_a$, $R_b$, $R_c$ and $R_d$ each are independently selected from the following substituents: H, $CH_3$—, $CH_3CH_2$—, CH₃CH₂CH₂—, (CH₃)₂CH—, CH₃(CH₂)₂CH₂—, (CH₃)₂CHCH₂—, (CH₃)₂CHCH₂CH₂—, CH₃CH₂CH(CH₃)—, (CH₃)₃C—, (CH₃)₃CCH₂—, CH₃SCH₂CH₂—, HOCH₂—, CH₃CH(OH)—, H₂NC(O)CH₂—, H₂NC(O)CH₂CH₂—, HSCH₂—, HOOCCH₂—, HOOCCH₂CH₂—, H₂NCH₂—, H₂NCH₂CH₂—, H₂N(CH₂)₂CH₂—, H₂N(CH₂)₃CH₂—, H₂N(CH₂)₄CH₂—, H₂N(CH₂)₅CH₂—, H₂NC(=NH)CH₂—, H₂NC(=NH)NHCH₂—, H₂NC(=NH)NHCH₂CH₂—, H₂NC(=NH)NH(CH₂)₂CH₂—, H₂NC(=NH)NH(CH₂)₃CH₂—,

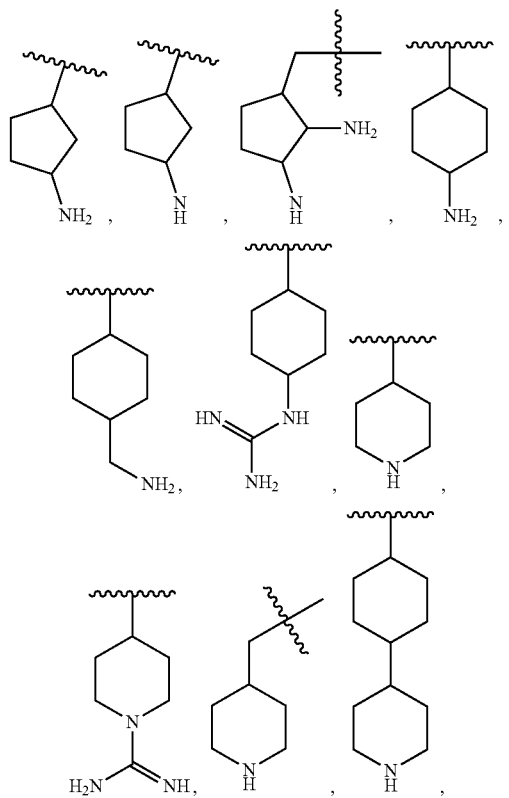

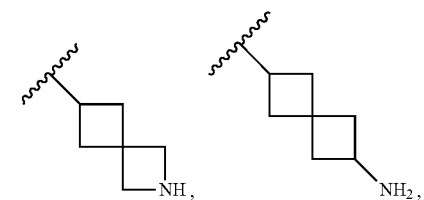

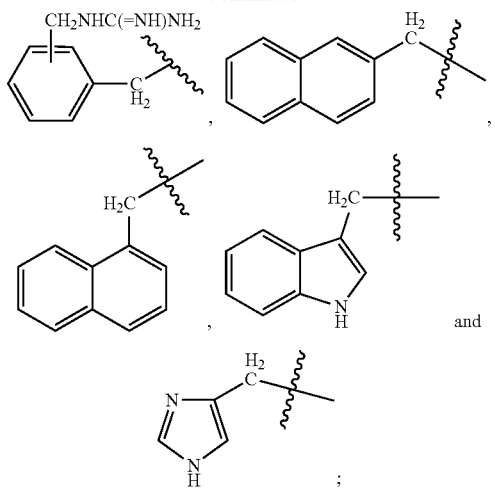

each of the substituents is optionally substituted with one or more groups independently selected from H, halogen, hydroxyl, amino, nitro, cyano, $C_{1-6}$alkyl, $C_{1-6}$haloalkyl, —CONH₂, $C_{3-10}$cycloalkyl, 3-10-membered heterocyclic group, $C_{6-14}$aryl and 5-14-membered heteroaryl;

$R_e$, $R_f$, $R_g$ and $R_h$ each are independently selected from H and $C_{1-4}$alkyl;

$R^2$ is selected from H, $C_{1-6}$alkyl, tert-butyloxycarbonyl, benzyloxycarbonyl, 9-fluorenylmethoxycarbonyl, allyloxycarbonyl, trimethylsilylethoxycarbonyl, methoxycarbonyl, ethoxycarbonyl, phthaloyl, p-toluenesulfonyl, o-nitrobenzenesulfonyl, p-nitrobenzenesulfonyl, formyl, acetyl, trifluoroacetyl, propionyl, pivaloyl, phenyl, benzoyl, triphenylmethyl, benzyl, 2,4-dimethoxybenzyl and p-methoxybenzyl, wherein, $R^2$ (e.g. $C_{1-6}$alkyl) is optionally substituted with one or more groups independently selected from halogen, hydroxyl, amino, nitro, cyano, carboxyl and —CONH₂; or, $R^2$ and $R_a$, together with the atoms to which they are separately linked, form a cyclic group selected from:

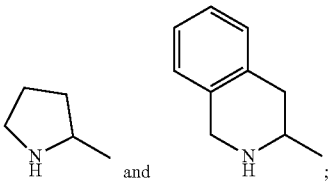

$R^1$ may be selected from:

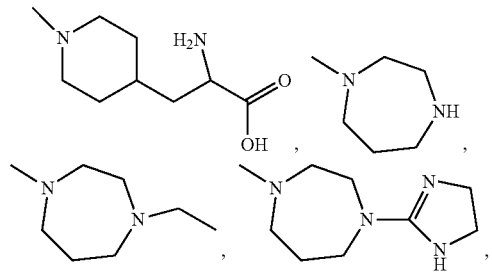

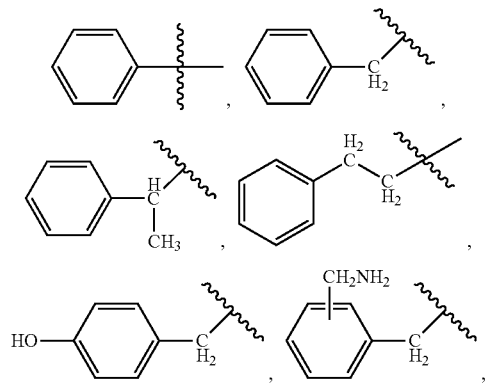

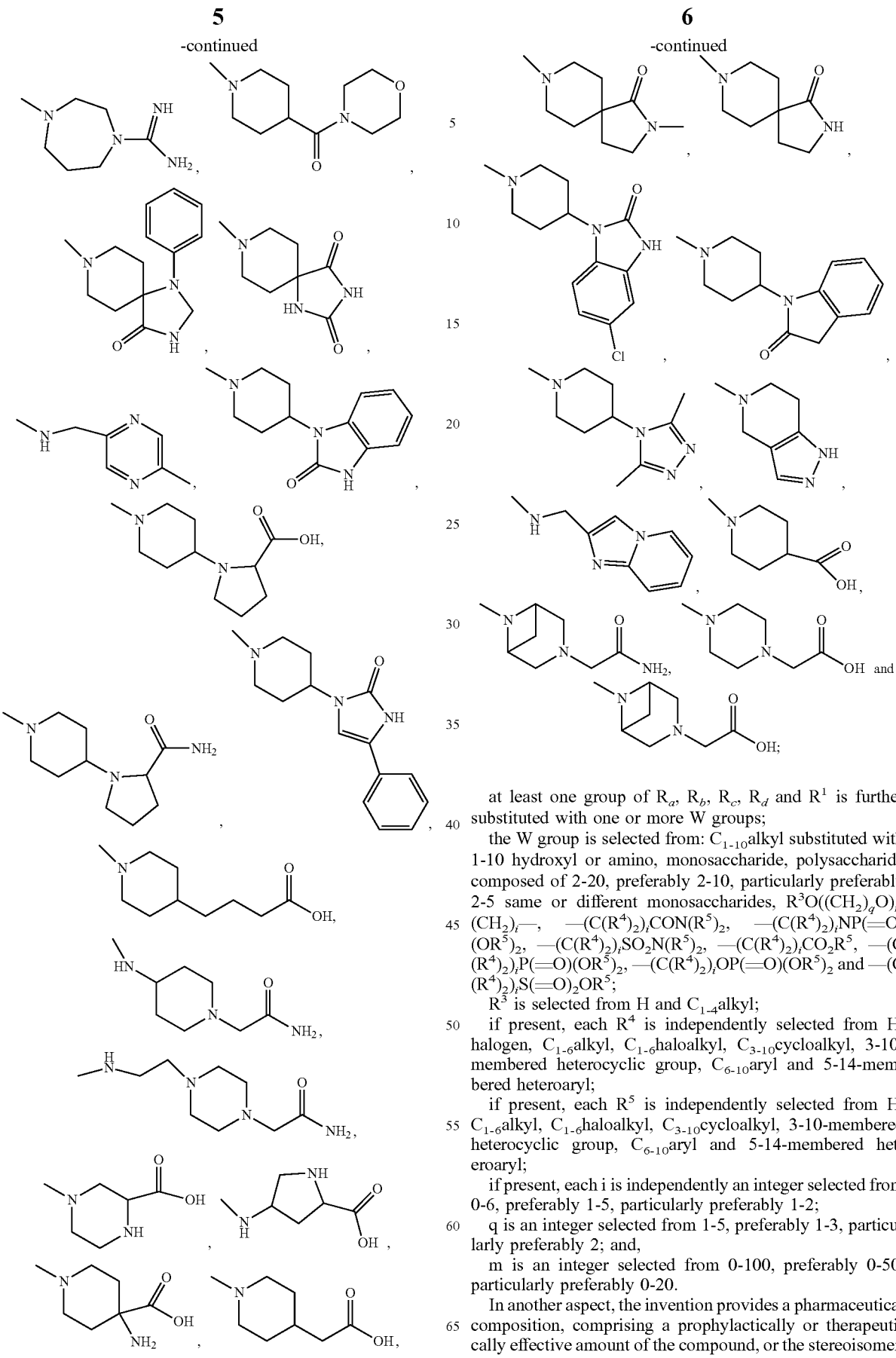

at least one group of $R_a$, $R_b$, $R_c$, $R_d$ and $R^1$ is further substituted with one or more W groups;

the W group is selected from: $C_{1-10}$alkyl substituted with 1-10 hydroxyl or amino, monosaccharide, polysaccharide composed of 2-20, preferably 2-10, particularly preferably 2-5 same or different monosaccharides, $R^3O((CH_2)_qO)_m(CH_2)_i$—, —$(C(R^4)_2)_iCON(R^5)_2$, —$(C(R^4)_2)_iNP(=O)(OR^5)_2$, —$(C(R^4)_2)_iSO_2N(R^5)_2$, —$(C(R^4)_2)_iCO_2R^5$, —$(C(R^4)_2)_iP(=O)(OR^5)_2$, —$(C(R^4)_2)_iOP(=O)(OR^5)_2$ and —$(C(R^4)_2)_iS(=O)_2OR^5$;

$R^3$ is selected from H and $C_{1-4}$alkyl;

if present, each $R^4$ is independently selected from H, halogen, $C_{1-6}$alkyl, $C_{1-6}$haloalkyl, $C_{3-10}$cycloalkyl, 3-10-membered heterocyclic group, $C_{6-10}$aryl and 5-14-membered heteroaryl;

if present, each $R^5$ is independently selected from H, $C_{1-6}$alkyl, $C_{1-6}$haloalkyl, $C_{3-10}$cycloalkyl, 3-10-membered heterocyclic group, $C_{6-10}$aryl and 5-14-membered heteroaryl;

if present, each i is independently an integer selected from 0-6, preferably 1-5, particularly preferably 1-2;

q is an integer selected from 1-5, preferably 1-3, particularly preferably 2; and, m is an integer selected from 0-100, preferably 0-50, particularly preferably 0-20.

In another aspect, the invention provides a pharmaceutical composition, comprising a prophylactically or therapeutically effective amount of the compound, or the stereoisomer, the crystalline polymorph, the solvate, the metabolite, the prodrug or the pharmaceutically acceptable salt or ester thereof according to the invention, and one or more pharmaceutically acceptable carriers.

In another aspect, the invention provides the compound, or the stereoisomer, the crystalline polymorph, the solvate, the metabolite, the prodrug or the pharmaceutically acceptable salt or ester thereof according to the invention, or the pharmaceutical composition according to the invention in manufacture of a medicament for prevention or treatment of a disease associated with κ-opioid receptor.

In another aspect, the invention provides the compound, or the stereoisomer, the crystalline polymorph, the solvate, the metabolite, the prodrug or the pharmaceutically acceptable salt or ester thereof according to the invention, or the pharmaceutical composition according to the invention, for use in prevention or treatment of a disease associated with κ-opioid receptor.

In another aspect, the invention provides a method for preventing or treating a disease associated with κ-opioid receptor, comprising administering to an individual in need thereof an effective amount of the compound, or the stereoisomer, the crystalline polymorph, the solvate, the metabolite, the prodrug or the pharmaceutically acceptable salt or ester thereof according to the invention, or the pharmaceutical composition according to the invention.

In the invention, the disease associated with κ-opioid receptor is selected from pain, inflammation, itching, edema, hyponatremia, hypopotassaemia, intestinal obstruction, cough and glaucoma. The pain includes neuropathic pain, somatic pain, visceral pain, skin pain, arthritis pain, nephrolith pain, hysterotrismus, dysmenorrhea, endometriosis, post-surgical pain, pain after medical treatment, eye pain, otitis pain, cancer pain and pain associated with gastrointestinal dysfunction.

In another aspect, the invention provides the compound, or the stereoisomer, the crystalline polymorph, the solvate, the metabolite, the prodrug or the pharmaceutically acceptable salt or ester thereof according to the invention, or the pharmaceutical composition according to the invention in manufacture of an agent for enhancing the level or activity of κ-opioid receptor in a cell.

In another aspect, the invention provides The compound, or the stereoisomer, the crystalline polymorph, the solvate, the metabolite, the prodrug or the pharmaceutically acceptable salt or ester thereof according to the invention, or the pharmaceutical composition according to the invention, for use in enhancing the level or activity of κ-opioid receptor in a cell.

In another aspect, the invention provides a method for enhancing the level or activity of κ-opioid receptor in a cell, comprising administering to the cell an effective amount of The compound, or the stereoisomer, the crystalline polymorph, the solvate, the metabolite, the prodrug or the pharmaceutically acceptable salt or ester thereof according to the invention, or the pharmaceutical composition according to the invention.

SPECIFIC MODES FOR CARRYING OUT THE INVENTION

Definition

Unless otherwise defined hereinafter, all technical and scientific terms used herein have the same meaning as commonly understood by those skilled in the art. A technique used herein refers to a technique that is generally understood in the art, including the variations of techniques or replacements of equivalent techniques apparent to those skilled in the art. Although it is believed that the following terms are well understood by those skilled in the art, the following definitions are still provided for better illustration of the invention.

The term "include", "comprise", "have", "contain" or "relate to" and other variant forms thereof mean that it is inclusive or open-ended, and does not exclude other unlisted elements, methods or steps.

As used herein, the term "a compound containing an amide bond" refers to a compound of any general formula of the present application, or a stereoisomer, a crystalline polymorph, a solvate, a metabolite, a prodrug or a pharmaceutically acceptable salt or ester thereof. The compound containing an amide bond preferably contains one or more amide bonds formed by condensation of same or different L-amino acids or D-amino acids.

The compound of the invention preferably comprises at least one W group, which is preferably a hydrophilic group (also called "lipophobic group"), covering all the atomic groups as known by those skilled in the art that are readily hydrophilic, can attract water molecules or enable the molecules comprising them be easily dissolved in water, or reduce the lipid-water partition coefficient of the molecules comprising them. The hydrophilic group includes, but is not limited to, the group containing a functional group such as a hydroxyl group, an ether group, an aldehyde group, an amino group, a quaternary ammonium group, an amide group, a sulfonylamino group, a phosphorylamino group, a carboxyl group, a sulfonic group, a sulfate group, and a phosphate group.

As used herein, the term "alkyl" is defined as a saturated aliphatic hydrocarbon group, which includes linear and branched aliphatic hydrocarbon groups. In some embodiments, alkyl has 1 to 6, e.g. 1 to 4 carbon atoms. For example, as used herein, the term "$C_{1-6}$alkyl" refers to a linear or branched, saturated aliphatic hydrocarbon group having 1 to 6 carbon atoms (e.g. methyl, ethyl, n-propyl, isopropyl, n-butyl, isobutyl, sec-butyl, tert-butyl, n-pentyl or n-hexyl); in some embodiments, the $C_{1-6}$alkyl is optionally substituted with one or more (e.g. 1 to 3) suitable substituents such as halogen (in this situation, the substituted $C_{1-6}$alkyl group is named as "$C_{1-6}$haloalkyl", e.g. $CF_3$, $C_2F_5$, $CHF_2$, $CH_2F$, $CH_2CF_3$, $CH_2Cl$ or —$CH_2CH_2CF_3$, etc.). The term "$C_{1-4}$alkyl" refers to a linear or branched, saturated aliphatic hydrocarbon group having 1 to 4 carbon atoms (e.g. methyl, ethyl, n-propyl, isopropyl, n-butyl, isobutyl, sec-butyl or tert-butyl).

As used herein, the term "cycloalkyl" refers to a saturated or unsaturated, non-aromatic monocyclic or polycyclic (such as bicyclic) hydrocarbon ring group (e.g. a single ring, such as cyclopropyl, cyclobutyl, cyclopentyl, cyclohexyl, cycloheptyl, cyclooctyl, cyclononyl, or a bicyclo, including spiro-ring, fused or bridged system (such as bicyclo[1.1.1] pentyl, bicyclo[2.2.1]heptyl, bicyclo[3.2.1]octyl or bicyclo [5.2.0]nonyl, decahydronaphthalenyl, etc.); in some embodiments, the cycloalkyl is optionally substituted with one or more (e.g. 1 to 3) suitable substituents. The cycloalkyl as used herein has 3 to 15 carbon atoms. For example, the term "$C_{3-10}$cycloalkyl" refers to a saturated or unsaturated, non-aromatic monocyclic or polycyclic (such as bicyclic) hydrocarbon ring group having 3 to 10 ring-forming carbon atoms (e.g. cyclopropyl, cyclobutyl, cyclopentyl, cyclohexyl or bicyclo[1.1.1]pentyl); in some embodiments, the $C_{3-10}$cycloalkyl is optionally substituted with one or more (e.g. 1 to 3) suitable substituents, such as cyclopropyl substituted with methyl.

As used herein, the term "heterocyclic group" refers to a saturated or unsaturated monocyclic or bicyclic group, wherein the ring has 2, 3, 4, 5, 6, 7, 8 or 9 carbon atoms and one or more (e.g. 1, 2, 3 or 4) heteroatoms selected from O, S, S(=O), S(=O)$_2$ and NR$^a$, wherein R$^a$ represents hydrogen atom, $C_{1-6}$alkyl or $C_{1-6}$haloalkyl; the heterocyclic group can be linked to the remaining moiety of a molecule via any one of the carbon atoms or a nitrogen atom (if present). In some preferred embodiments, at least one (e.g. one or two) carbon atoms of the heterocyclic group is substituted with an oxygen group (=O). Particularly, 3-10-membered heterocyclic group is a group having 3-10 ring-forming carbon atoms and heteroatoms, for example, including, but not limited to oxiranyl, aziridinyl, azetidinyl, oxetanyl, tetrahydrofuranyl, dioxolinyl, pyrrolidinyl, pyrrolidonyl, imidazolidinyl, pyrazolidinyl, pyrrolinyl, tetrahydropyranyl, piperidinyl, morpholinyl, dithianyl, thiomorpholinyl, piperazinyl and trithianyl.

As used herein, the term "aryl" refers to an all-carbon monocyclic or polycyclic aromatic group having a conjugated n-electron system. For example, as used herein, the term "$C_{6-14}$aryl" refers to an aromatic group having 6 to 14 carbon atoms, such as phenyl or naphthyl. In some embodiments, the aryl is optionally substituted with one or more (e.g. 1 to 3) suitable substituents.

As used herein, the term "heteroaryl" refers to a monocyclic or polycyclic aromatic group containing one or more same or different heteroatoms, such as oxygen, nitrogen or sulfur; further, the heteroaryl refers to a monocyclic, bicyclic or tricyclic aromatic group having 5, 6, 8, 9, 10, 11, 12, 13 or 14 ring atoms, particularly 1, 2, 3, 4, 5, 6, 9 or 10 carbon atoms, and comprising at least one heteroatom which may be same or different, such as oxygen, nitrogen or sulfur; and the heteroaryl group may be a benzo-fused group. In particular, the heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiadiazolyl, and the like, and benzo-fused derivatives thereof; or pyridyl, pyridazinyl, pyrimidinyl, pyrazinyl, triazinyl, and the like, and benzo-fused derivatives thereof.

As used herein, the term "halo" or "halogen" is defined as including F, Cl, Br or I.

As used herein, the term "monosaccharide" refers to a polyhydroxy aldehyde or polyhydroxy ketone compound containing 3 to 6 carbon atoms, including, but not limited to triose (such as glyceraldehyde), pentose (such as ribose, arabinose, xylose, ribulose), hexose (such as glucose, fructose, galactose), etc.

As used herein, the term "polysaccharide" refers to a carbohydrate chain formed by multiple (e.g. 2-20, preferably 2-10, particularly preferably 2-5) monosaccharides units bound together by glycosidic linkages, including, but not limited to maltose, lactose, sucrose, trehalose, starch, cellulose, etc.

The term "substituted" means that one or more (e.g. one, two, three or four) hydrogens on a specified atom are selectively replaced by specified group(s), provided that the valence of the specified atom does not exceed its normal valence in the current situation, and a substantially stable compound is formed by the substitution. The combination of the substituent(s) and/or variant(s) is only permissible when such a combination leads to a substantially stable compound.

The term "optionally" means that the group or substituent described herein may be unsubstituted or substituted by a specific group or an atomic group.

As used herein, the term "one or more" refers to one or more than one under reasonable conditions, such as 2, 3, 4, 5 or 10.

In the chemical structure, when a bond of a substituent is displayed as cross over a bond connecting two atoms in a ring, the substituent may be bonded to any of the ring-forming atoms in the substitutable ring.

If the compound, group or substituent described herein is described as: "optionally" substituted with a specified group or atomic group, it means that the compound, group or substituent may be (1) unsubstituted or (2) substituted with the specified group or atomic group.

The compound according to the invention may comprise one or more (e.g. one, two, three or four) isotopic replacements. For example, in the compound, H may be in any isotopic form, including $^1$H, $^2$H (D or deuterium) and $^3$H (T or tritium); C may be in any isotopic form, including $^{12}$C, $^{13}$C and $^{14}$C; O may be in any isotopic form, including $^{16}$O and $^{18}$O; etc.

The term "stereoisomer" refers to an isomer resulted from the presence of at least one asymmetric center in a compound. In a compound having one or more (e.g. one, two, three or four) asymmetric centers, it leads to generation of racemates, a racemic mixture, a single enantiomer, a mixture of diastereomers and a single diastereomer. A specific individual molecule may also be present in a geometric (cis/trans) isomer. Similarly, the compound of the invention may be present in a mixture of two or more forms of different structures (commonly referred to as tautomers) that are in a quick equilibrium. Representative examples of tautomers include keto-enol tautomers, phenol-ketone tautomers, nitroso-oxime tautomers, imine-enamine tautomers, etc. It is understood that the scope of the present application covers all the isomers or mixtures thereof in such a ratio (e.g. 60%, 65%, 70%, 75%, 80%, 85%, 90%, 95%, 96%, 97%, 98%, 99%).

The invention covers all the possible crystalline forms or polymorphs of the compound of the invention, which may be a single polymorph or a mixture of more than one polymorph in any ratio.

It should also be understood that some compounds of the invention may be present in a free form for treatment, or if appropriate, may be present in a form of its pharmaceutically acceptable derivative. According to the invention, a pharmaceutically acceptable derivative includes, but is not limited to, a pharmaceutically acceptable salt, ester, solvate, metabolite or prodrug, which can directly or indirectly provide the compound of the invention or a metabolite or residue thereof, after administration to a patient in need thereof. Thus, when "the compound of the invention" is mentioned herein, it also intends to cover the above mentioned derivative forms of the compound.

A pharmaceutically acceptable salt of the compound of the invention includes its acid addition salt and base addition salt.

Suitable acid addition salts are formed from acids that form pharmaceutically acceptable salts. Examples include acetate, adipate, aspartate, benzoate, besylate, bicarbonate/carbonate, bisulfate/sulfate, borate, camphorsulfonate, citrate, cyclamate, ethanedisulfonate, ethanesulfonate, formate, fumarate, glucoheptonate, gluconate, glucuronate, hexafluorophosphate, hydrochloride/chloride, hydrobromide/bromide, hydroiodide/iodide, isethionate, lactate, malate, maleate, malonate, methanesulfonate, methyl sulfate, naphthylate, 2-naphthalenesulfonate, nicotinate, nitrate, orotate, oxalate, palmitate, pamoate, phosphate/biphosphate/dihydric phosphate, pyroglutamate, bisaccharate, stearate, succinate, tannate, tartrate, tosylate, trifluoroacetate and xinofoate.

Suitable base addition salts are formed from bases that form pharmaceutically acceptable salts. Examples include aluminum salts, arginine salts, benzathine benzylpenicillin salts, calcium salts, choline salts, diethylamine salts, diethanolamine salts, glycinates, lysine salts, magnesium salts, meglumine salts, ethanolamine salts, potassium salts, sodium salts, tromethamine salts and zinc salts.

Reviews on suitable salts could be found in Stahl and Wermuth, "Handbook of Pharmaceutical Salts: Properties, Selection, and Use" (Wiley-VCH, 2002). Methods for preparing pharmaceutically acceptable salts of the compound of the invention are known to those skilled in the art. In some preferred embodiments, the pharmaceutically acceptable salts are selected from the group consisting of formates, acetates, hydrochlorides, and trifluoroacetates.

As used herein, the term "ester" refers to an ester derived from a compound of the general formula in the present application, including a physiologically hydrolysable ester which is hydrolysable under physiological conditions to release the compound of the invention in a form of a free acid or alcohol. The compound of the invention may also be an ester itself.

The compound of the invention may be present in the form of a solvate and a hydrate, and the solvent or water may be present in an amount as calculated in a stoichiometric or non-stoichiometric ratio.

The scope of the invention also includes the metabolite of the compound of the invention, i.e. the substance formed in vivo upon the administration of the compound of the invention.

The scope of invention further includes a prodrug of the compound of the invention. Generally, such a prodrug may be a derivative formed from the functional group of the compound which is readily converted in vivo to a therapeutically active compound as desired. Thus, under these conditions, the term "administering/administration" used in the therapeutic method according to the invention shall include the treatment of various diseases or disorders with a prodrug form of one or more of the claimed compounds, however, the prodrug form is converted to the above compound in vivo upon administration to an individual. For example, in "Design of Prodrug", ed. H. Bundgaard, Elsevier, 1985, a conventional method for selecting and preparing a suitable prodrug derivative is described.

During the preparation of the compound of the invention, it is necessary and/or desirable to protect the sensitive group or reactive group on any relevant molecule, thereby forming a chemically protected form of the compound of the invention. This can be accomplished by conventional protecting groups, for example, the protecting groups described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, which are incorporated herein by reference. By using the method known in the art, the protecting group can be removed in a suitable later phase.

Compounds

In an embodiment, the invention provides a compound, or a stereoisomer, a crystalline polymorph, a solvate, a metabolite, a prodrug or a pharmaceutically acceptable salt or ester thereof, wherein the compound has a structure of Formula (I):

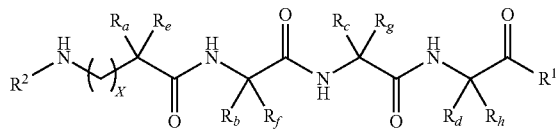

wherein:

X is an integer selected from 0-6;

$R_a$, $R_b$, $R_c$ and $R_d$ each are independently selected from the following substituents: H, $CH_3$—, $CH_3CH_2$—, $CH_3CH_2CH_2$—, $(CH_3)_2CH$—, $CH_3(CH_2)_2CH_2$—, $(CH_3)_2CHCH_2$—, $(CH_3)_2CHCH_2CH_2$—, $CH_3CH_2CH(CH_3)$—, $(CH_3)_3C$—, $(CH_3)_3CCH_2$—, $CH_3SCH_2CH_2$—, $HOCH_2$—, $CH_3CH(OH)$—, $H_2NC(O)CH_2$—, $H_2NC(O)CH_2CH_2$—, $HSCH_2$—, $HOOCCH_2$—, $HOOCCH_2CH_2$—, $H_2NCH_2$—, $H_2NCH_2CH_2$—, $H_2N(CH_2)_2CH_2$—, $H_2N(CH_2)_3CH_2$—, $H_2N(CH_2)_4CH_2$—, $H_2N(CH_2)_5CH_2$—, $H_2NC(=NH)CH_2$—, $H_2NC(=NH)NHCH_2$—, $H_2NC(=NH)NHCH_2CH_2$—, $H_2NC(=NH)NH(CH_2)_2CH_2$—, $H_2NC(=NH)NH(CH_2)_3CH_2$—,

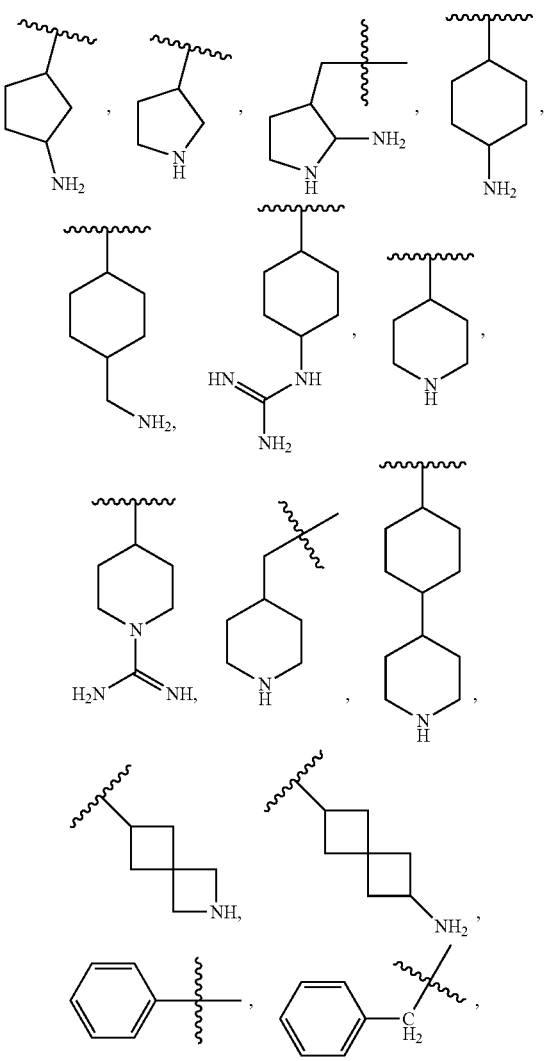

-continued

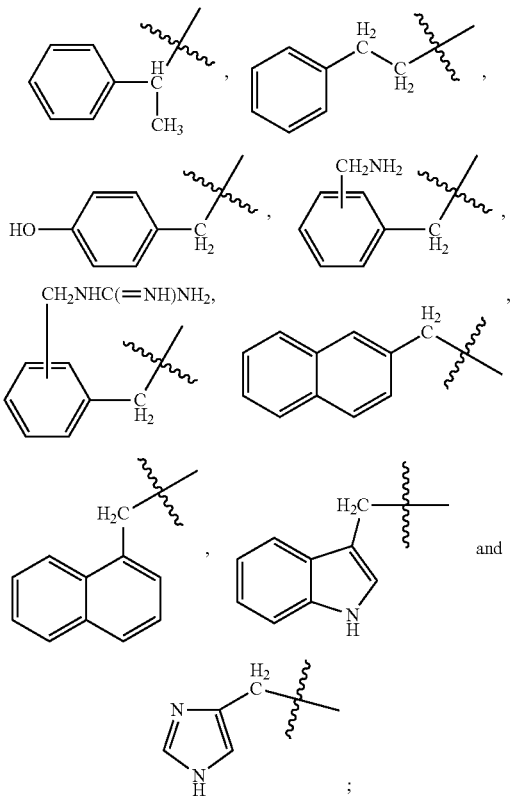

each of the substituents is optionally substituted with one or more groups independently selected from H, halogen, hydroxyl, amino, nitro, cyano, $C_{1-6}$alkyl, $C_{1-6}$haloalkyl, —$CONH_2$, $C_{3-10}$cycloalkyl, 3-10-membered heterocyclic group, $C_{6-14}$aryl and 5-14-membered heteroaryl;

$R_e$, $R_f$, $R_g$ and $R_h$ each are independently selected from H and $C_{1-4}$alkyl;

$R^2$ is selected from H, $C_{1-6}$alkyl, tert-butyloxycarbonyl, benzyloxycarbonyl, 9-fluorenylmethoxycarbonyl, allyloxycarbonyl, trimethylsilylethoxycarbonyl, methoxycarbonyl, ethoxycarbonyl, phthaloyl, p-toluenesulfonyl, o-nitrobenzenesulfonyl, p-nitrobenzenesulfonyl, formyl, acetyl, trifluoroacetyl, propionyl, pivaloyl, phenyl, benzoyl, triphenylmethyl, benzyl, 2,4-dimethoxybenzyl and p-methoxybenzyl, wherein, $R^2$ (e.g. $C_{1-6}$alkyl) is optionally substituted with one or more groups independently selected from halogen, hydroxyl, amino, nitro, cyano, carboxyl and —$CONH_2$; or, $R^2$ and $R_a$, together with the atoms to which they are separately linked, form a cyclic group selected from:

$R^1$ is selected from:

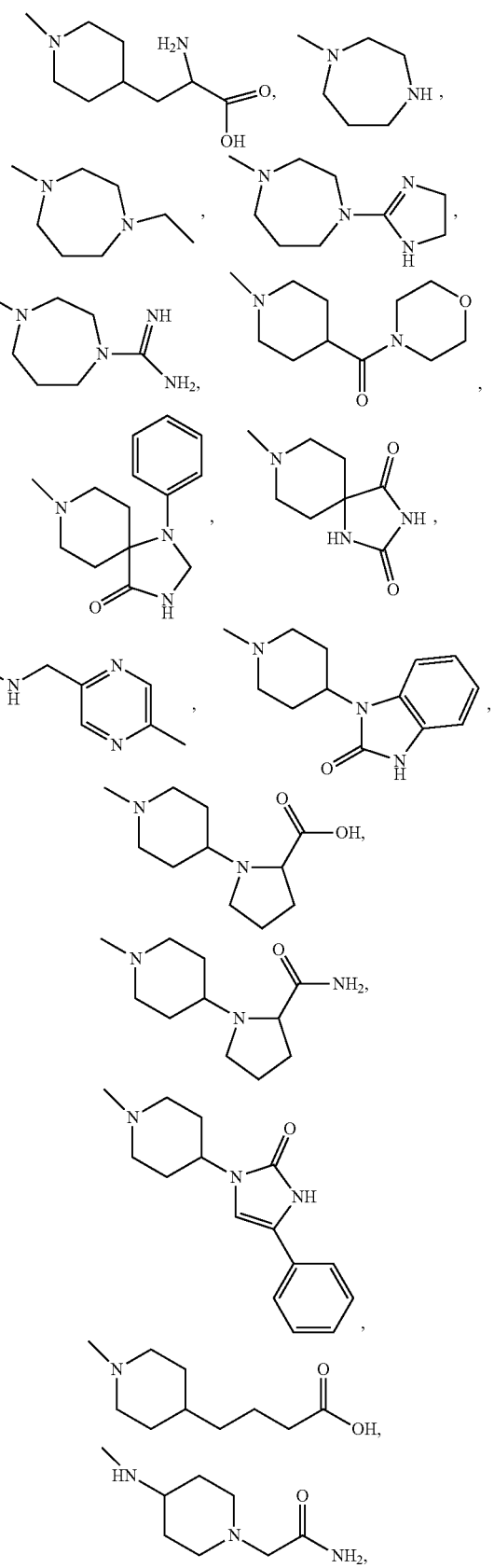

-continued

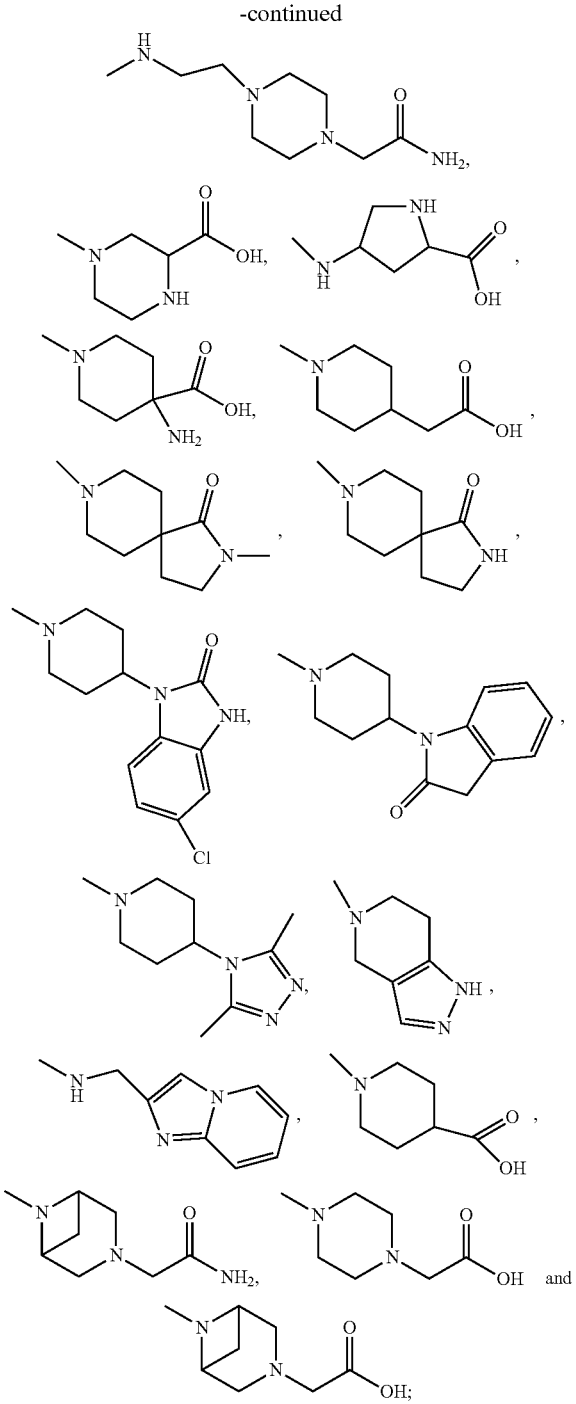

and, at least one group of $R_a$, $R_b$, $R_c$, $R_d$ and $R^1$ is further substituted with one or more W groups;

wherein, the W group is selected from: $C_{1-10}$alkyl substituted with 1-10 hydroxyl or amino, monosaccharide, polysaccharide composed of 2-20, preferably 2-10, particularly preferably 2-5 same or different monosaccharides, $R^3O$ $((CH_2)_qO)_m(CH_2)_i$—, —$(C(R^4)_2)_iCON(R^5)_2$, —$(C(R^4)_2)_iNP(=O)(OR^5)_2$, —$(C(R^4)_2)_iSO_2N(R^5)_2$, —$(C(R^4)_2)_iCO_2R^5$, —$(C(R^4)_2)_iP(=O)(OR^5)_2$, —$(C(R^4)_2)_iOP(=O)(OR^5)_2$ and —$(C(R^4)_2)_iS(=O)_2OR^5$;

$R^3$ is selected from H and $C_{1-4}$alkyl;

if present, each $R^4$ is independently selected from H, halogen, $C_{1-6}$alkyl, $C_{1-6}$haloalkyl, $C_{3-10}$cycloalkyl, 3-10-membered heterocyclic group, $C_{6-10}$aryl and 5-14-membered heteroaryl;

if present, each $R^5$ is independently selected from H, $C_{1-6}$alkyl, $C_{1-6}$haloalkyl, $C_{3-10}$cycloalkyl, 3-10-membered heterocyclic group, $C_{6-10}$aryl and 5-14-membered heteroaryl;

if present, each i is independently an integer selected from 0-6, preferably 1-5, particularly preferably 1-2;

q is an integer selected from 1-5, preferably 1-3, particularly preferably 2;

m is an integer selected from 0-100, preferably 0-50, particularly preferably 0-20.

In some preferred embodiments, the invention provides a compound, or a stereoisomer, a crystalline polymorph, a solvate, a metabolite, a prodrug or a pharmaceutically acceptable salt or ester thereof, wherein the compound has a structure of Formula (I):

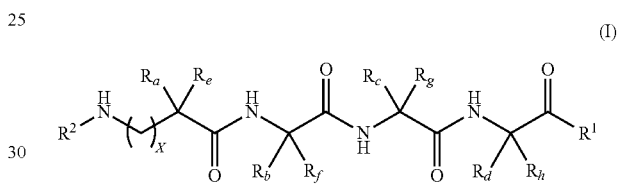

(I)

wherein,

X is an integer selected from 0-6;

$R_a$, $R_b$, $R_c$ and $R_d$ each are independently selected from the following substituents: H, $CH_3$—, $CH_3CH_2$—, $CH_3CH_2CH_2$—, $(CH_3)_2CH$—, $CH_3(CH_2)_2CH_2$—, $(CH_3)_2CHCH_2$—, $(CH_3)_2CHCH_2CH_2$—, $CH_3CH_2CH(CH_3)$—, $(CH_3)_3C$—, $(CH_3)_3CCH_2$—, $CH_3SCH_2CH_2$—, $HOCH_2$—, $CH_3CH(OH)$—, $H_2NC(O)CH_2$—, $H_2NC(O)CH_2CH_2$—, $HSCH_2$—, $HOOCCH_2$—, $HOOCCH_2CH_2$—, $H_2NCH_2$—, $H_2NCH_2CH_2$—, $H_2N(CH_2)_2CH_2$—, $H_2N(CH_2)_3CH_2$—, $H_2N(CH_2)_4CH_2$—, $H_2N(CH_2)_5CH_2$—, $H_2NC(=NH)CH_2$—, $H_2NC(=NH)NHCH_2$—, $H_2NC(=NH)NHCH_2CH_2$—, $H_2NC(=NH)NH(CH_2)_2CH_2$—, $H_2NC(=NH)NH(CH_2)_3CH_2$—,

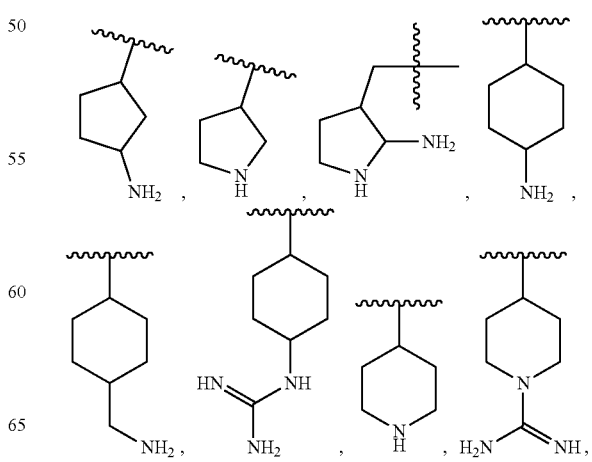

-continued

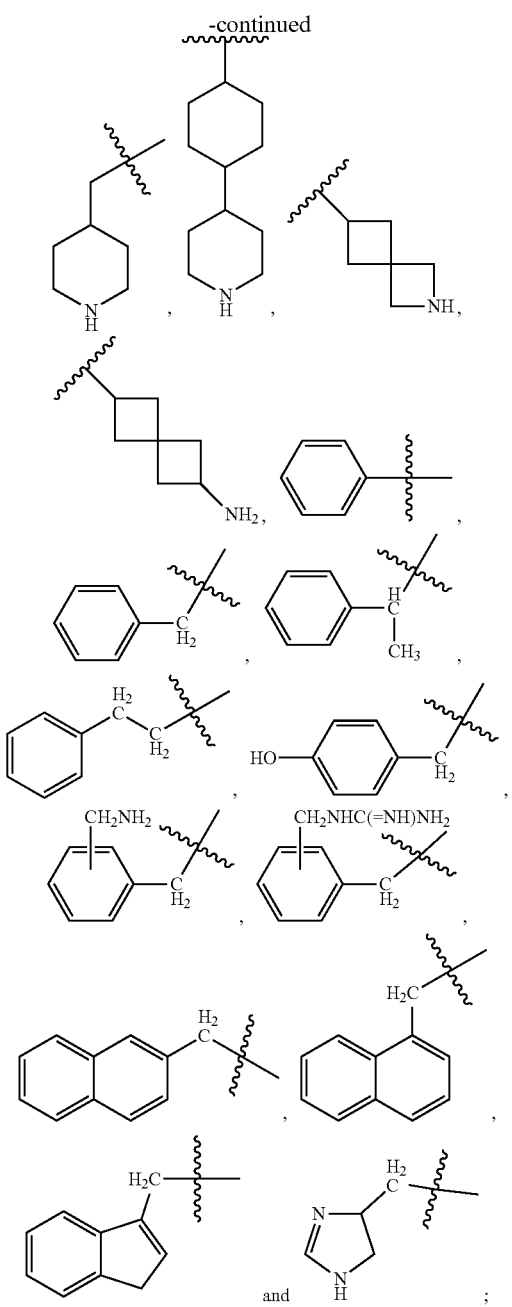

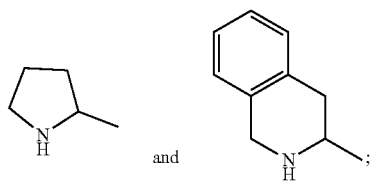

and $R^1$ is selected from:

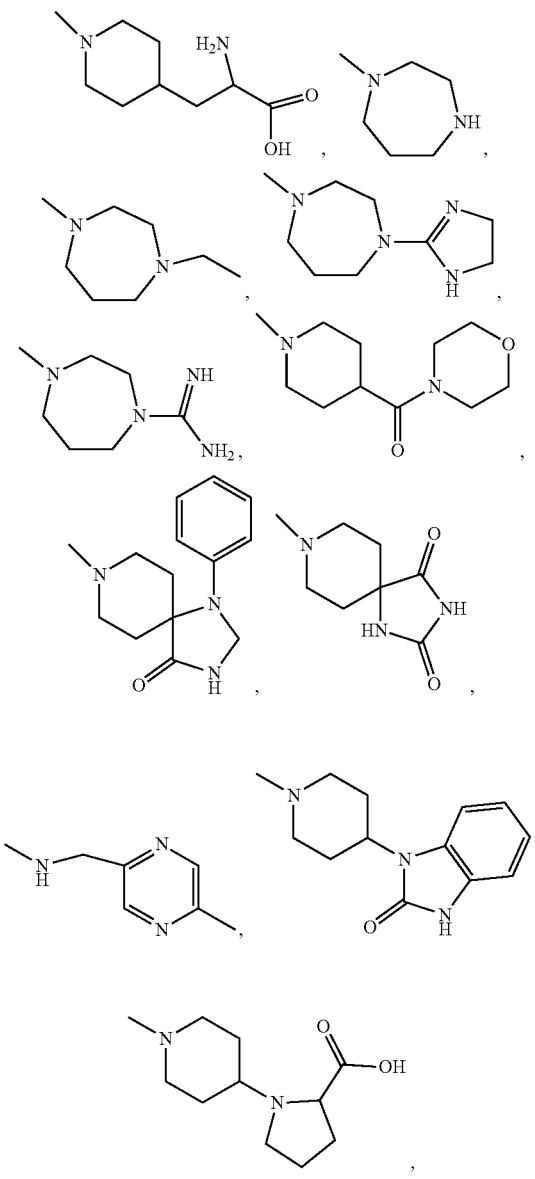

each of the substituents is optionally substituted with one or more groups independently selected from H, halogen, hydroxyl, amino, nitro, cyano, $C_{1-6}$alkyl, $C_{1-6}$haloalkyl, —$CONH_2$, $C_{3-10}$cycloalkyl, 3-10-membered heterocyclic group, $C_{6-14}$aryl and 5-14-membered heteroaryl;

$R_e$, $R_f$, $R_g$ and $R_h$ each are independently selected from H and $C_{1-4}$alkyl;

$R^2$ is selected from H, $C_{1-6}$alkyl, tert-butyloxycarbonyl, benzyloxycarbonyl, 9-fluorenylmethoxycarbonyl, allyloxycarbonyl, trimethylsilylethoxycarbonyl, methoxycarbonyl, ethoxycarbonyl, phthaloyl, p-toluenesulfonyl, o-nitrobenzenesulfonyl, p-nitrobenzenesulfonyl, formyl, acetyl, trifluoroacetyl, propionyl, pivaloyl, phenyl, benzoyl, triphenylmethyl, benzyl, 2,4-dimethoxybenzyl and p-methoxybenzyl; or, $R^2$ and $R_a$, together with the atoms to which they are separately linked, form a cyclic group selected from:

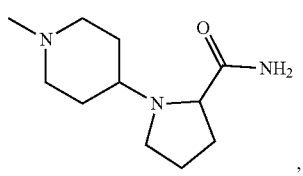

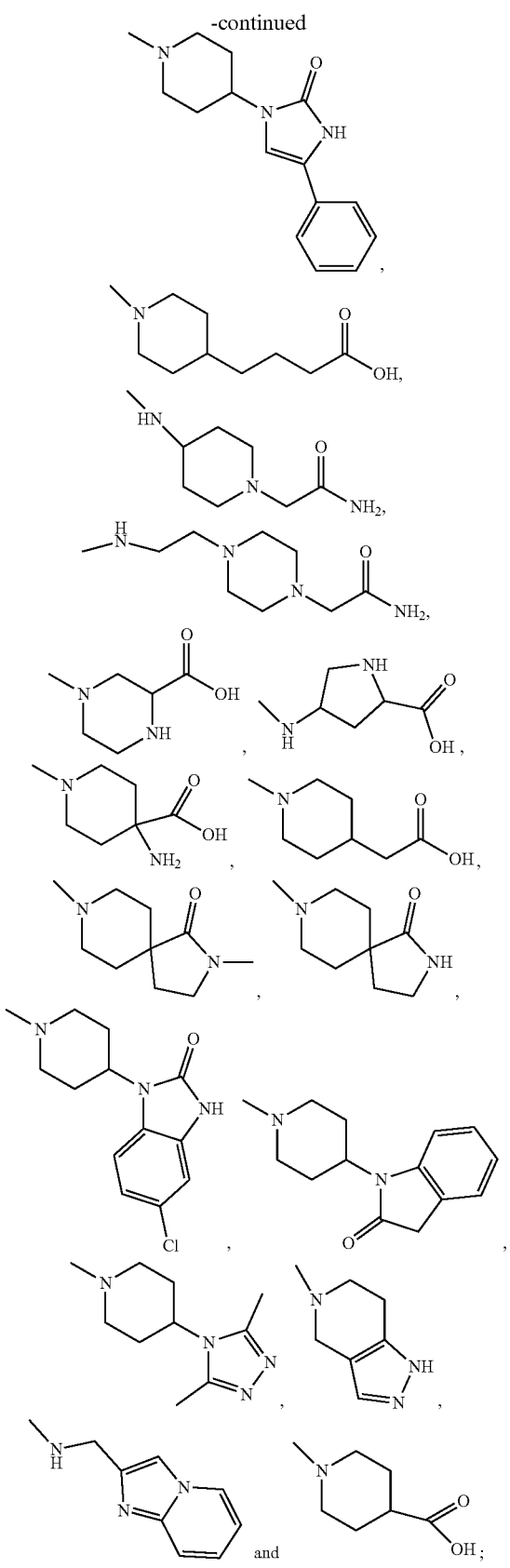

at least one group of $R_a$, $R_b$, $R_c$, $R_d$ and $R^1$ is further substituted with one or more W groups;

wherein, the W group is selected from: $C_{1-10}$alkyl substituted with 1-10 hydroxyl or amino, monosaccharide, polysaccharide composed of 2-20, preferably 2-10, particularly preferably 2-5 same or different monosaccharides, $R^3O((CH_2)_qO)_m(CH_2)_i$—, —$(C(R^4)_2)_iCON(R^5)_2$, —$(C(R^4)_2)_iNP(=O)(OR^5)_2$, —$(C(R^4)_2)_iSO_2N(R^5)_2$, —$(C(R^4)_2)_iCO_2R^5$, —$(C(R^4)_2)_iP(=O)(OR^5)_2$, —$(C(R^4)_2)_iOP(=O)(OR^5)_2$ and —$(C(R^4)_2)_iS(=O)_2OR^5$;

$R^3$ is selected from H and $C_{1-4}$alkyl;

if present, each $R^4$ is independently selected from H, halogen, $C_{1-6}$alkyl, $C_{1-6}$haloalkyl, $C_{3-10}$cycloalkyl, 3-10-membered heterocyclic group, $C_{6-10}$aryl and 5-14-membered heteroaryl;

if present, each $R^5$ is independently selected from H, $C_{1-6}$alkyl, $C_{1-6}$haloalkyl, $C_{3-10}$cycloalkyl, 3-10-membered heterocyclic group, $C_{6-10}$aryl and 5-14-membered heteroaryl;

i is an integer selected from 0-6, preferably 1-5, particularly preferably 1-2;

q is an integer selected from 1-5, preferably 1-3, particularly preferably 2; and m is an integer selected from 0-100, preferably 0-50, particularly preferably 0-20.

In some preferred embodiments, X is 0, 1, 2, 3, 4 or 5.

In some more preferred embodiments, X is 0 or 1.

In some particularly preferred embodiments, X is 0.

In some preferred embodiments, $R_a$ is selected from $CH_3$—, $(CH_3)_3C$—, $(CH_3)_3CCH_2$—,

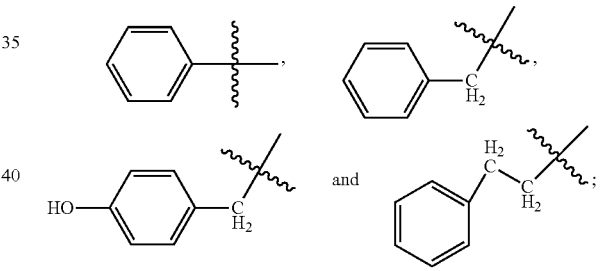

wherein, when $R_a$ is

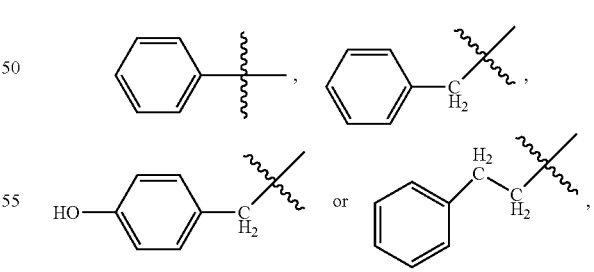

the benzene ring in $R_a$ is optionally substituted with one or more groups independently selected from H, halogen, hydroxyl, amino, nitro, cyano, $C_{1-6}$alkyl, $C_{1-6}$haloalkyl and —$CONH_2$; when $R_a$ is $CH_3$—, $(CH_3)_3C$— or $(CH_3)_3CCH_2$—, $R_a$ is optionally substituted with one or more groups independently selected from $C_{3-10}$cycloalkyl, 3-10-membered heterocyclic group, $C_{6-14}$aryl and 5-14-membered heteroaryl.

In some more preferred embodiments, $R_a$ is

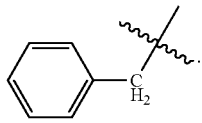 [SMILES: *Cc1ccccc1]

In some preferred embodiments, $R_b$ is selected from $CH_3$—,

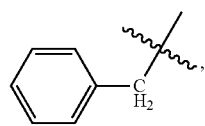 , 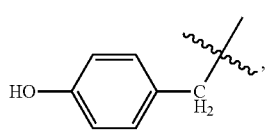 ,

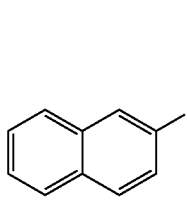 and 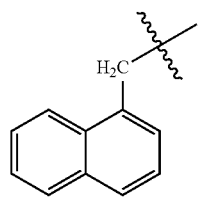

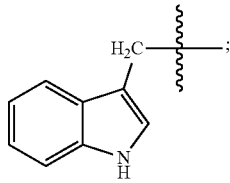 ;

wherein, when $R_b$ is $CH_3$—, $R_b$ is optionally substituted with one or more groups independently selected from $C_{3-10}$cycloalkyl, 3-10-membered heterocyclic group, $C_{6-14}$aryl and 5-14-membered heteroaryl; when $R_b$ is

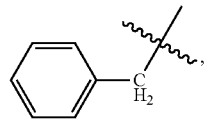 , 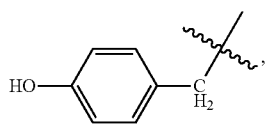 ,

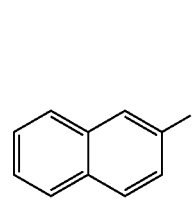 , 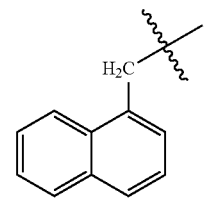 or

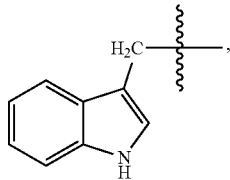 , $R_b$ is optionally substituted with one or more groups independently selected from H, halogen, nitro, cyano, $C_{1-6}$alkyl, $C_{1-6}$haloalkyl and —$CONH_2$.

In some more preferred embodiments, $R_b$ is

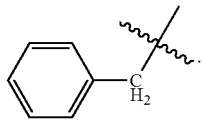 [SMILES: *Cc1ccccc1]

In some preferred embodiments, $R_c$ is selected from $CH_3$—, $(CH_3)_2CH$—, $(CH_3)_2CHCH_2$—, $CH_3(CH_2)_2CH_2$—, $(CH_3)_2CHCH_2CH_2$—, $CH_3SCH_2CH_2$— and

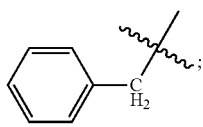 ;

wherein, when $R_c$ is $CH_3$—, $R_c$ is optionally substituted with one or more groups independently selected from $C_{3-10}$cycloalkyl, 3-10-membered heterocyclic group, $C_{6-14}$aryl and 5-14-membered heteroaryl.

In some more preferred embodiments, $R_c$ is $(CH_3)_2CHCH_2$—.

In some preferred embodiments, $R_d$ is selected from the following substituents: $H_2NCH_2$—, $H_2NCH_2CH_2$—, $H_2N(CH_2)_2CH_2$—, $H_2N(CH_2)_3CH_2$—, $H_2N(CH_2)_4CH_2$—, $H_2N(CH_2)_5CH_2$—, $H_2NC(=NH)CH_2$—, $H_2NC(=NH)NHCH_2$—, $H_2NC(=NH)NHCH_2CH_2$—, $H_2NC(=NH)NH(CH_2)_2CH_2$—, $H_2NC(=NH)NH(CH_2)_3CH_2$—,

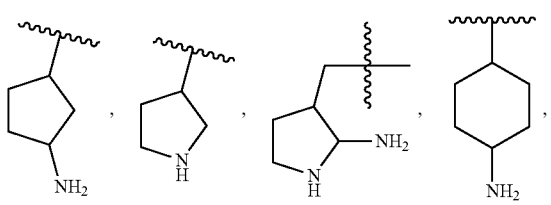

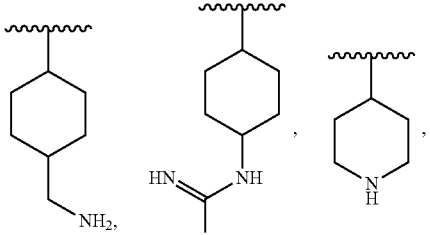

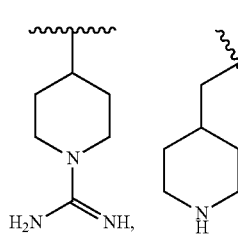 , 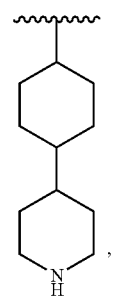

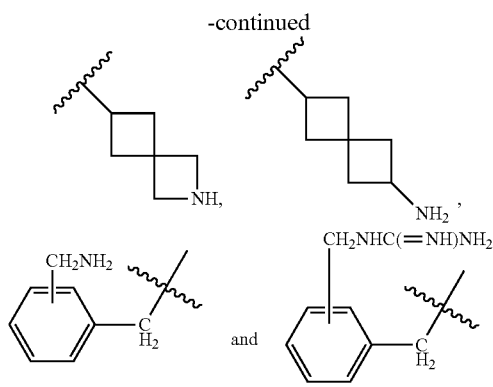

each of the substituents is optionally substituted with one or more groups independently selected from H and $C_{1-4}$alkyl.

In some more preferred embodiments, $R_d$ is $H_2N(CH_2)_3CH_2-$.

In some preferred embodiments, the $R_d$ may be further substituted with one or more W groups.

In some preferred embodiments, the $R_d$ may be further substituted with multiple W groups.

In some more preferred embodiments, the group formed by the substitution of the $R_d$ with multiple W groups is selected from: $(W)_2-NCH_2-$, $(W)_2-NCH_2CH_2-$, $(W)_2-N(CH_2)_2CH_2-$, $(W)_2-N(CH_2)_3CH_2-$, $(W)_2-N(CH_2)_4CH_2-$, $(W)_2-N(CH_2)_5CH_2-$, $(W)_2-NC(=NH)CH_2-$, $(W)_2-NC(=NH)NHCH_2-$, $(W)_2-NC(=NH)NHCH_2CH_2-$ and $(W)_2-NC(=NH)NH(CH_2)_2CH_2-$. In some particularly preferred embodiments, the group formed by the substitution of the $R_d$ with multiple W groups is $(W)_2-N(CH_2)_3CH_2-$.

In some preferred embodiments, W is selected from $-(CH_2)_nOH$, $HOCH_2(CHOH)_nCH_2-$, $(HOCH_2)_2CH-$, $(HOCH_2)_3C-$, $-(CH_2)_nNH_2$, $-(C(R^4)_2)_iCON(R^5)_2$, $-(C(R^4)_2)_iCO_2R^5$, $C_{3-6}$monosaccharide, polysaccharide composed of 2-20 (preferably 2-10, particularly preferably 2-5) same or different $C_{3-6}$monosaccharide and $R^3O(CH_2CHO)H_2CH_2-$, wherein, if present, n is independently an integer selected from 1-8 (preferably selected from 1-5, particularly preferably selected from 1-3);

m is an integer selected from 0-50, preferably, m is 1, 2, 3, 4, 5, 6, 7, 8, 9, 10, 11, 12, 13, 14, 15, 20, 25 or 30;

if present, each i is independently 0, 1, 2, 3, 4 or 5, preferably, i is 2;

$R^3$ is selected from H, methyl, ethyl, n-propyl, isopropyl, n-butyl, isobutyl or tert-butyl, preferably, $R^3$ is methyl;

if present, each $R^4$ is independently selected from H, halogen and $C_{1-4}$alkyl, preferably, $R^4$ is H;

if present, each $R^5$ is independently selected from H and $C_{1-4}$alkyl, preferably, $R^5$ is H.

In some more preferred embodiments, W is selected from $-(CH_2)_nOH$, $HOCH_2(CHOH)_nCH_2-$, $(HOCH_2)_2CH-$, $(HOCH_2)_3C-$, $-(CH_2)_nNH_2$, $C_{3-6}$monosaccharide, polysaccharide composed of 2-20, preferably 2-10, particularly preferably 2-5 same or different $C_{3-6}$monosaccharide, and $R^3O(CH_2CH_2O)_mCH_2CH_2-$, wherein n is an integer selected from 1-8, preferably selected from 1-5, particularly preferably selected from 1-3. In some preferred embodiments, $R^3$ is selected from H, methyl, ethyl, n-propyl, isopropyl, n-butyl, isobutyl or tert-butyl. In some particularly preferred embodiments, $R^3$ is methyl. In some preferred embodiments, m is an integer selected from 0-50. In some particularly preferred embodiments, m is 1, 2, 3, 4, 5, 6, 7, 8, 9, 10, 11, 12, 13, 14, 15, 20, 25 or 30.

In some more preferred embodiments, W is $-CH_2OH$, $-(CH_2)_2H$, $HOCH_2CHOHCH_2-$, $(HOCH_2)_2CH-$, $-CH_2NH_2$, $-(CH_2)_2NH_2$, $-(CH_2)_3NH_2$, $CH_3O(CH_2CH_2O)CH_2CH_2-$, $CH_3O(CH_2CH_2O)_2CH_2CH_2-$, $CH_3O(CH_2CH_2O)_6CH_2CH_2-$, $CH_3O(CH_2CH_2O)_{11}CH_2CH_2-$, $-CH_2COOH$ or $-CH_2C(O)NH_2$.

In some particularly preferred embodiments, W is $-CH_2OH$, $-(CH_2)_2OH$, $HOCH_2CH(OH)CH_2-$, $(HOCH_2)_2CH-$, $-CH_2NH_2$, $-(CH_2)_2NH_2$, $-(CH_2)_3NH_2$, $CH_3O(CH_2CH_2O)CH_2CH_2-$, $CH_3O(CH_2CH_2O)_2CH_2CH_2-$, $CH_3O(CH_2CH_2O)_6CH_2CH_2-$ or $CH_3O(CH_2CH_2O)_{11}CH_2CH_2-$.

In other particularly preferred embodiments, W is $CH_3O(CH_2CH_2O)CH_2CH_2-$ or $-CH_2COOH$.

In some preferred embodiments, the $R_d$ may be further substituted with one W group.

In some more preferred embodiments, the group formed by the substitution of the $R_d$ with one W group is selected from: $W-NHCH_2-$, $W-NHCH_2CH_2-$, $W-NH(CH_2)_2CH_2-$, $W-NH(CH_2)_3CH_2-$, $W-NH(CH_2)_4CH_2-$, $W-NH(CH_2)_5CH_2-$, $W-NHC(=NH)CH_2-$, $W-NHC(=NH)NHCH_2-$, $W-NHC(=NH)NHCH_2CH_2-$, $W-NHC(=NH)NH(CH_2)_2CH_2-$, $W-NHC(=NH)NH(CH_2)_3CH_2-$,

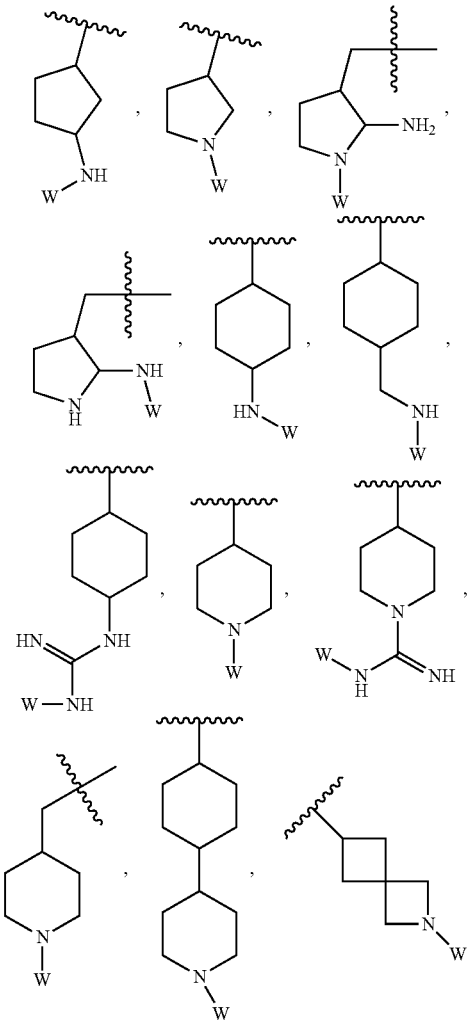

-continued

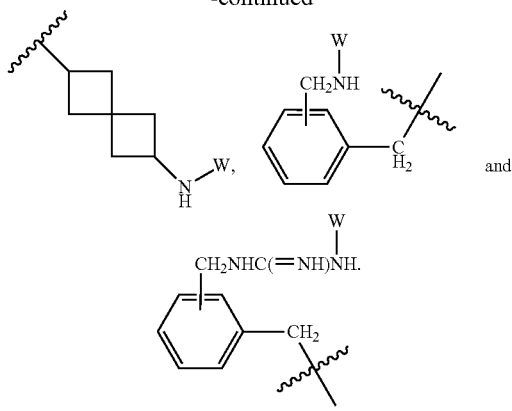

In some particularly preferred embodiments, the group formed by the substitution of the $R_d$ with one W group is W—NH(CH$_2$)$_3$CH$_2$—.

In some preferred embodiments, W is selected from —(CH$_2$)$_n$OH, HOCH$_2$(CHOH)$_n$CH$_2$—, (HOCH$_2$)$_2$CH—, (HOCH$_2$)$_3$C—, —(CH$_2$)$_n$NH$_2$, —(C(R$^4$)$_2$)$_i$CON(R$^5$)$_2$, —(C(R$^4$)$_2$)$_i$CO$_2$R$^5$, C$_{3-6}$monosaccharide, polysaccharide composed of 2-20 (preferably 2-10, particularly preferably 2-5) same or different C$_{3-6}$monosaccharide, and R$^3$O(CH$_2$CH$_2$O)$_m$CH$_2$CH$_2$—, wherein, if present, n is independently an integer selected from 1-8 (preferably 1-5, particularly preferably 1-3);

m is an integer selected from 0-50, preferably, m is 1, 2, 3, 4, 5, 6, 7, 8, 9, 10, 11, 12, 13, 14, 15, 20, 25 or 30;

if present, i is independently 0, 1, 2, 3, 4 or 5, preferably, i is 2;

R$^3$ is selected from H, methyl, ethyl, n-propyl, isopropyl, n-butyl, isobutyl or tert-butyl, preferably, R$^3$ is methyl;

if present, each R$^4$ is independently selected from H, halogen and C$_{1-4}$alkyl, preferably, R$^4$ is H;

if present, each R$^5$ is independently selected from H and C$_{1-4}$alkyl; preferably, R$^5$ is H.

In some more preferred embodiments, W is selected from —(CH$_2$)$_n$OH, HOCH$_2$(CHOH)$_n$CH$_2$—, (HOCH$_2$)$_2$CH—, (HOCH$_2$)$_3$C—, —(CH$_2$)$_n$NH$_2$, C$_{3-6}$monosaccharide, polysaccharide composed of 2-20, preferably 2-10, particularly preferably 2-5 same or different C$_{3-6}$monosaccharide, and R$^3$O(CH$_2$CH$_2$O)$_m$CH$_2$CH$_2$—, wherein n is an integer selected from 1-8, preferably 1-5, particularly preferably 1-3. In some preferred embodiments, R$^3$ is selected from H, methyl, ethyl, n-propyl, isopropyl, n-butyl, isobutyl or tert-butyl. In some particularly preferred embodiments, R$^3$ is methyl. In some preferred embodiments, m is an integer selected from 0-50. In some particularly preferred embodiments, m is 1, 2, 3, 4, 5, 6, 7, 8, 9, 10, 11, 12, 13, 14, 15, 20, 25 or 30.

In some more preferred embodiments, W is —CH$_2$OH, —(CH$_2$)$_2$OH, HOCH$_2$CH(OH)CH$_2$—, (HOCH$_2$)$_2$CH—, —CH$_2$NH$_2$, —(CH$_2$)$_2$NH$_2$, —(CH$_2$)$_3$NH$_2$, CH$_3$O(CH$_2$CH$_2$O)CH$_2$CH$_2$—, CH$_3$O(CH$_2$CH$_2$O)$_2$CH$_2$CH$_2$—, CH$_3$O(CH$_2$CH$_2$O)$_6$CH$_2$CH$_2$—, CH$_3$O(CH$_2$CH$_2$O)$_{11}$CH$_2$CH$_2$—, —CH$_2$COOH or —CH$_2$C(O)NH$_2$.

In some particularly preferred embodiments, W is —CH$_2$OH, —(CH$_2$)$_2$OH, HOCH$_2$(CHOH)CH$_2$—, (HOCH$_2$)$_2$CH—, —CH$_2$NH$_2$, —(CH$_2$)$_2$NH$_2$, —(CH$_2$)$_3$NH$_2$, CH$_3$O(CH$_2$CH$_2$O)CH$_2$CH$_2$—, CH$_3$O(CH$_2$CH$_2$O)$_2$CH$_2$CH$_2$—, CH$_3$O(CH$_2$CH$_2$O)$_6$CH$_2$CH$_2$— or CH$_3$O(CH$_2$CH$_2$O)$_{11}$CH$_2$CH$_2$—.

In some preferred embodiments, R$_e$, R$_f$, R$_g$ and R$_h$ each are independently selected from H, methyl, ethyl, n-propyl, isopropyl, n-butyl, isobutyl and tert-butyl.

In some more preferred embodiments, R$_e$, R$_f$, R$_g$ and R$_h$ is independently H or methyl.

In some preferred embodiments, R$^2$ is selected from H, C$_{1-6}$alkyl, wherein C$_{1-6}$alkyl is optionally substituted with one or more groups independently selected from hydroxyl, amino and carboxyl.

In some more preferred embodiments, R$^2$ is selected from H, NH$_2$CH$_2$CH$_2$—, NH$_2$(CH$_2$)$_2$CH$_2$— and HOOCCH$_2$—.

In some particularly preferred embodiments, R$^2$ is H.

In some preferred embodiments, R$^1$ is selected from:

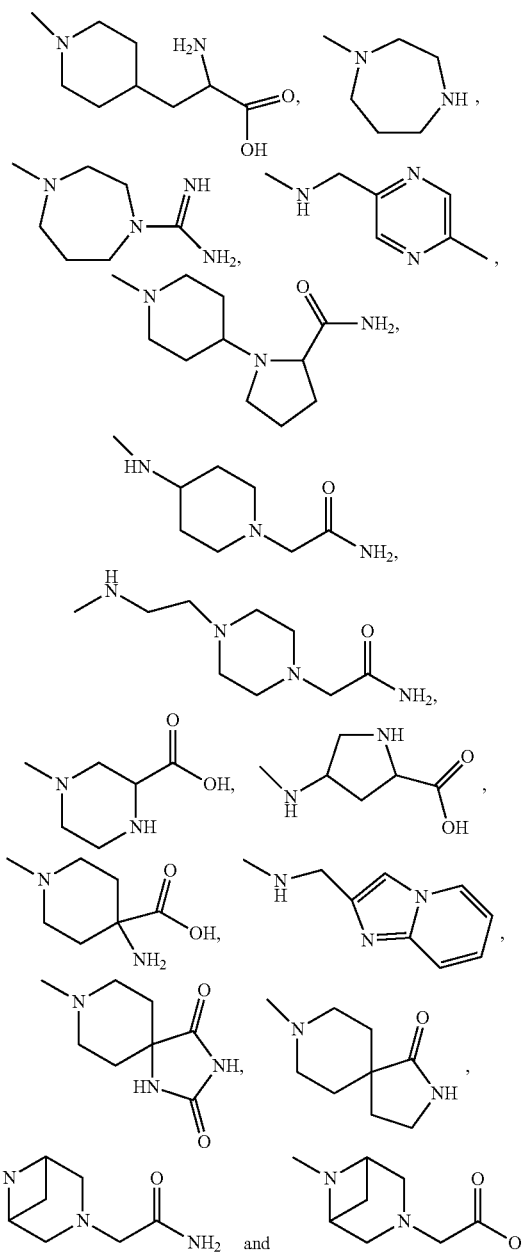

In some more preferred embodiments, R$^1$ is selected from:

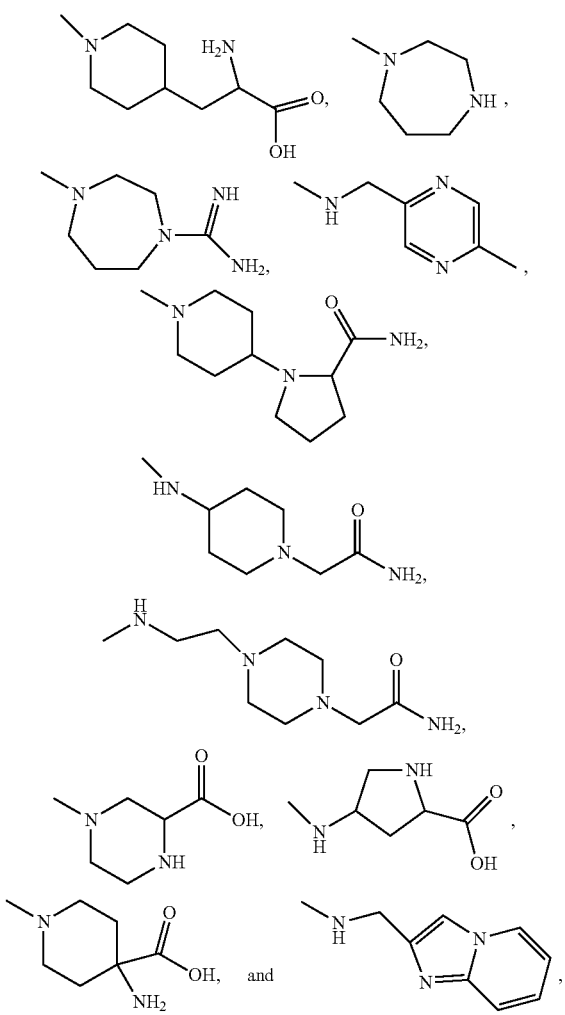

In some particularly preferred embodiments, $R^1$ is

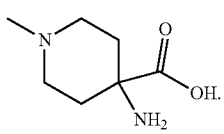

In some preferred embodiments, the $R^1$ may be further substituted with one or more W groups.

In some preferred embodiments, the $R^1$ may be further substituted with one W group.

In some more preferred embodiments, the group formed by the substitution of the $R^1$ with one W group is selected from

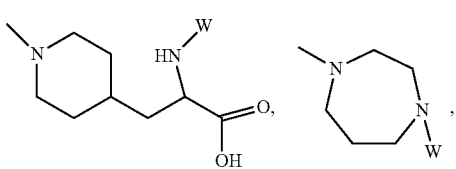

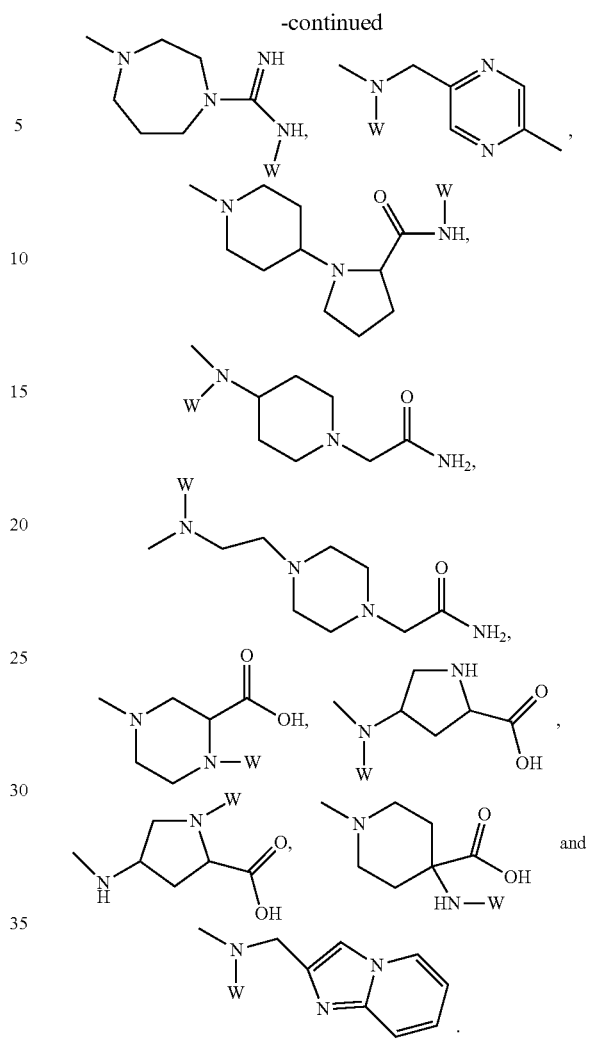

In some particularly preferred embodiments, the group formed by the substitution of the $R^1$ with one W group is

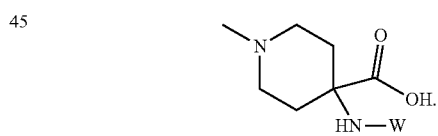

In some preferred embodiments, W is selected from —$(CH_2)_n$OH, $HOCH_2(CH(OH))_n CH_2$—, $(HOCH_2)_2 CH$—, $(HOCH_2)_3 C$—, —$(CH_2)_n NH_2$, —$(C(R^4)_2)_i CON(R^5)_2$, —$(C(R^4)_2)_i CO_2 R^5$, $C_{3-6}$monosaccharide, polysaccharide composed of 2-20 (preferably 2-10, particularly preferably 2-5) same or different $C_{3-6}$monosaccharide, and $R^3 O(CH_2 CH_2 O)_m CH_2 CH_2$—, wherein, if present, n is independently is an integer selected from 1-8, preferably 1-5, particularly preferably 1-3;

m is an integer selected from 0 to 50. In some particularly preferred embodiments, m is 1, 2, 3, 4, 5, 6, 7, 8, 9, 10, 11, 12, 13, 14, 15, 20, 25 or 30;

if present, i is independently 0, 1, 2, 3, 4 or 5, preferably, i is 2;

$R^3$ is selected from H, methyl, ethyl, n-propyl, isopropyl, n-butyl, isobutyl or tert-butyl, preferably, $R^3$ is methyl;

if present, each $R^4$ is independently selected from H, halogen and $C_{1-4}$alkyl, preferably, $R^4$ is H;

if present, each $R^5$ is independently selected from H and $C_{1-4}$alkyl, preferably, $R^5$ is H.

In some more preferred embodiments, W is selected from —$(CH_2)_nOH$, $HOCH_2(CHOH)_nCH_2$—, $(HOCH_2)_2CH$—, $(HOCH_2)_3C$—, —$(CH_2)_nNH_2$, $C_{3-6}$monosaccharide, polysaccharide composed of 2-20, preferably 2-10, particularly preferably 2-5 same or different $C_{3-6}$monosaccharide, and $R^3O(CH_2CH_2O)_mCH_2CH_2$—, wherein n is an integer selected from 1 to 8, preferably 1-5, particularly preferably 1-3. In some preferred embodiments, $R^3$ is selected from H, methyl, ethyl, n-propyl, isopropyl, n-butyl, isobutyl or tert-butyl. In some particularly preferred embodiments, $R^3$ is methyl. In some preferred embodiments, m is an integer selected from 0 to 50. In some particularly preferred embodiments, m is 1, 2, 3, 4, 5, 6, 7, 8, 9, 10, 11, 12, 13, 14, 15, 20, 25 or 30.

In some more preferred embodiments, W is —$CH_2OH$, —$(CH_2)_2OH$, $HOCH_2CH(OH)CH_2$—, $(HOCH_2)_2CH$—, —$CH_2NH_2$, —$(CH_2)_2NH_2$, —$(CH_2)_3NH_2$, $CH_3O(CH_2CH_2O)CH_2CH_2$—, $CH_3O(CH_2CH_2O)_2CH_2CH_2$—, $CH_3O(CH_2CH_2O)_6CH_2CH_2$—, $CH_3O(CH_2CH_2O)_{11}CH_2CH_2$—, —$CH_2COOH$ or —$CH_2C(O)NH_2$.

In some particularly preferred embodiments, W is —$CH_2OH$, —$(CH_2)_2OH$, $HOCH_2(CHOH)CH_2$—, $(HOCH_2)_2CH$—, —$CH_2NH_2$, —$(CH_2)_2NH_2$, —$(CH_2)_3NH_2$, $CH_3O(CH_2CH_2O)CH_2CH_2$—, $CH_3O(CH_2CH_2O)_2CH_2CH_2$—, $CH_3O(CH_2CH_2O)_6CH_2CH_2$— or $CH_3O(CH_2CH_2O)_{11}CH_2CH_2$—.

In other particularly preferred embodiments, W is $CH_3O(CH_2CH_2O)CH_2CH_2$—, $CH_3O(CH_2CH_2O)_2CH_2CH_2$—, $CH_3O(CH_2CH_2O)_6CH_2CH_2$— or $CH_3O(CH_2CH_2O)_{11}CH_2CH_2$—.

In the preferred embodiments, the compound according to the invention has the structure of Formula (I)-1:

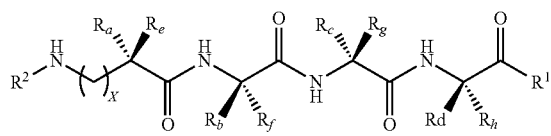

(I)-1 wherein, the groups have the same meanings as described above.

In some preferred embodiments, the invention provides a compound, or a stereoisomer, a crystalline polymorph, a solvate, a metabolite, a prodrug or a pharmaceutically acceptable salt or ester thereof, wherein the compound has a structure of Formula (II):

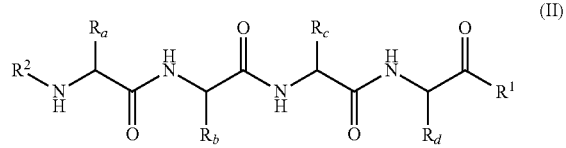

(II)

wherein $R_a$, $R_b$ and $R_c$ each are independently selected from the following substituents: H, $CH_3$—, $CH_3CH_2$—, $CH_3CH_2CH_2$—, $(CH_3)_2CH$—, $CH_3(CH_2)_2CH_2$—, $(CH_3)_2CHCH_2$—, $(CH_3)_2CHCH_2CH_2$—, $CH_3CH_2CH(CH_3)$—, $(CH_3)_3C$—, $(CH_3)_3CCH_2$—, $CH_3SCH_2CH_2$—,

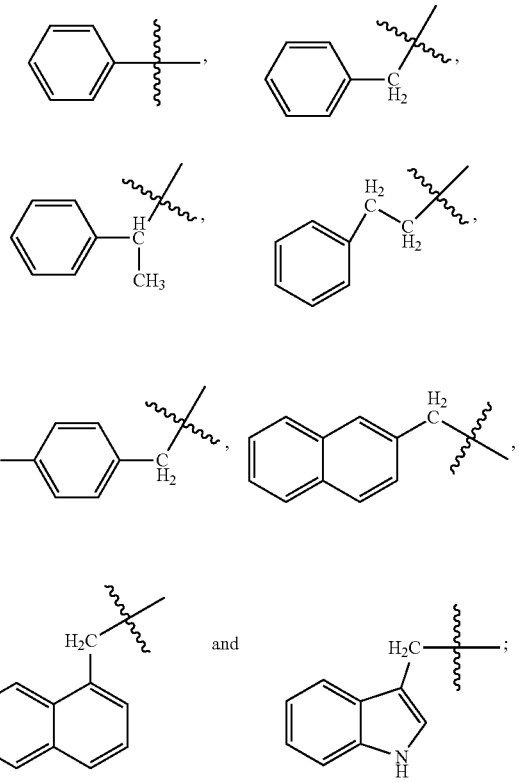

each of the substituents is optionally substituted with one or more groups selected from H, halogen, hydroxyl, amino, nitro, cyano, $C_{1-6}$alkyl, $C_{1-4}$haloalkyl, —$CONH_2$, $C_{3-10}$cycloalkyl, 3-10-membered heterocyclic group, $C_{6-14}$aryl and 5-14-membered heteroaryl;

$R_d$ is selected from the following substituents: $H_2NCH_2$—, $H_2NCH_2CH_2$—, $H_2N(CH_2)_2CH_2$—, $H_2N(CH_2)_3CH_2$—, $H_2N(CH_2)_4CH_2$—, $H_2N(CH_2)_5CH_2$—, $H_2NC(=NH)CH_2$—, $H_2NC(=NH)NHCH_2$—, $H_2NC(=NH)NHCH_2CH_2$—, $H_2NC(=NH)NH(CH_2)_2CH_2$—, $H_2NC(=NH)NH(CH_2)_3CH_2$—,

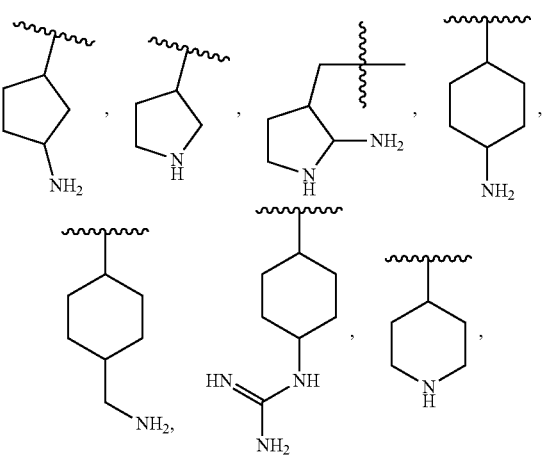

-continued

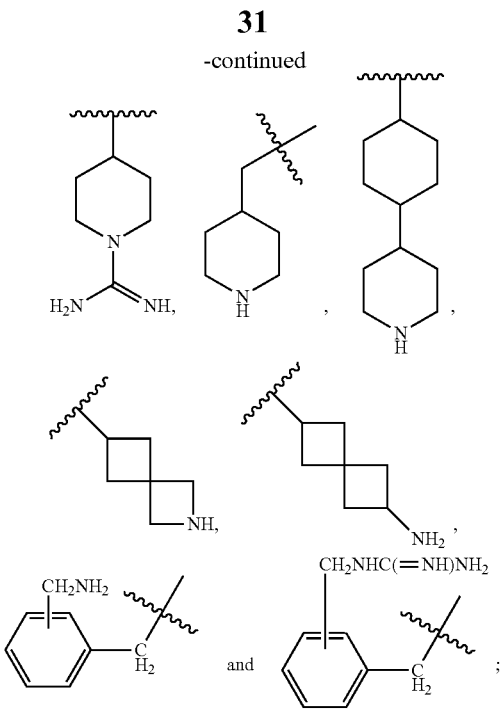

each of the substituents is optionally substituted with one or more H or $C_{1-4}$alkyl;

$R^2$ is selected from H, $NH_2CH_2CH_2$—, $NH_2(CH_2)_2CH_2$— and $HOOCCH_2$—;

$R^1$ may be selected from:

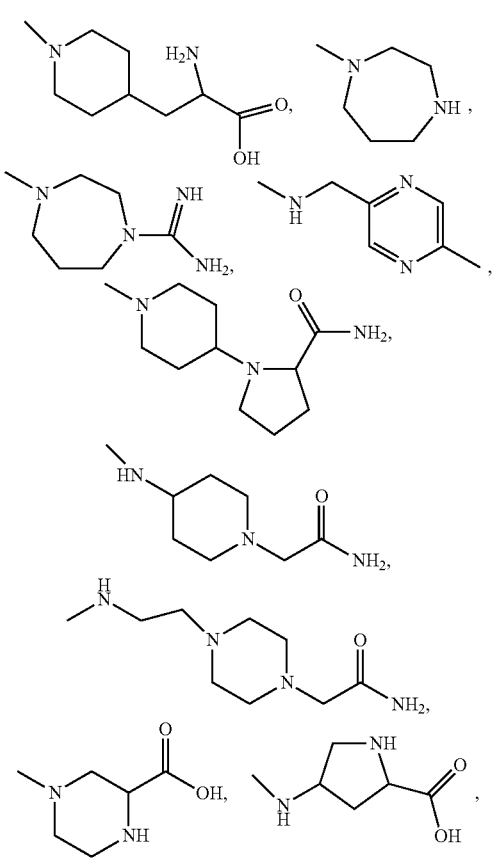

-continued

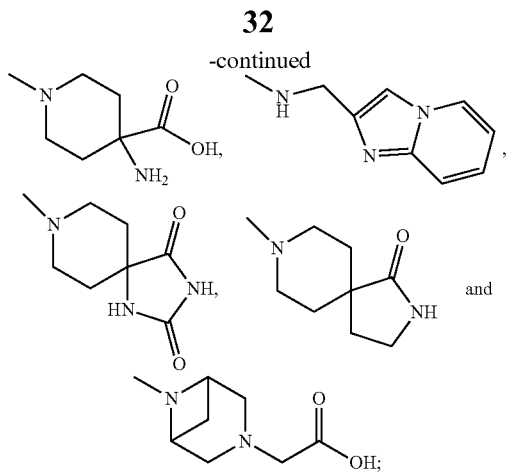

at least one group of $R_d$ and $R^1$ is substituted with one or more W groups;

wherein, the W group is selected from: —$(C(R^4)_2)_iCON(R^5)_2$, —$(C(R^4)_2)_iCO_2R^5$, —$(CH_2)_nOH$, $HOCH_2(CHOH)_nCH_2$—, $(HOCH_2)_2CH$—, $(HOCH_2)_3C$—, —$(CH_2)_nNH_2$, $C_{3-6}$monosaccharide, polysaccharide composed of 2-20 (preferably 2-10, particularly preferably 2-5) same or different $C_{3-6}$monosaccharide, and $R^3O(CH_2CH_2O)_mCH_2CH_2$;

$R^3$ is selected from H and $C_{1-4}$alkyl;

if present, each $R^4$ is independently selected from H, halogen, $C_{1-6}$alkyl, $C_{1-6}$haloalkyl, $C_{3-10}$cycloalkyl, 3-10-membered heterocyclic group, $C_{6-10}$aryl and 5-14-membered heteroaryl; preferably, if present, each $R^4$ is independently selected from H, halogen and $C_{1-4}$alkyl; more preferably, $R^4$ is H;

if present, each $R^5$ is independently selected from H, $C_{1-6}$alkyl, $C_{1-6}$haloalkyl, $C_{3-10}$cycloalkyl, 3-10-membered heterocyclic group, $C_{6-10}$aryl and 5-14-membered heteroaryl; preferably, if present, each $R^5$ is independently selected from H, halogen and $C_{1-4}$alkyl; more preferably, $R^5$ is H;

if present, each i is independently an integer selected from 0-6, preferably 1-5, particularly preferably 1-2;

if present, n is independently an integer selected from 1-8, preferably 1-5, particularly preferably 1-3; and, m is an integer selected from 0-100, preferably 0-50, particularly preferably 0-20.

In some preferred embodiments, the invention provides a compound, or a stereoisomer, a crystalline polymorph, a solvate, a metabolite, a prodrug or a pharmaceutically acceptable salt or ester thereof, wherein the compound has a structure of Formula (II):

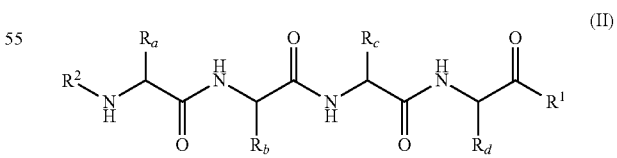

wherein $R_a$, $R_b$ and $R_c$ each are independently selected from the following substituents: H, $CH_3$—, $CH_3CH_2$—, $CH_3CH_2CH_2$—, $(CH_3)_2CH$—, $CH_3(CH_2)_2CH_2$—, $(CH_3)_2CHCH_2$—, $(CH_3)_2CHCH_2CH_2$—, $CH_3CH_2CH(CH_3)$—, $(CH_3)_3C$—, $(CH_3)_3CCH_2$—, $CH_3SCH_2CH_2$—,

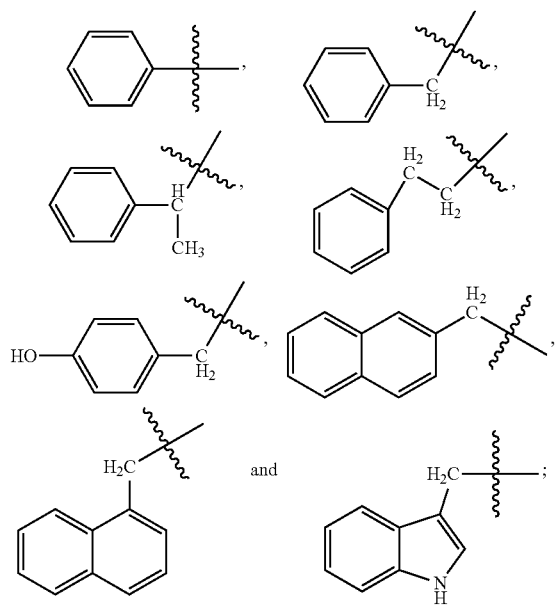

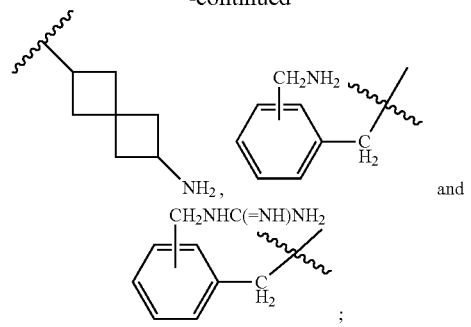

each of the substituents is optionally substituted with one or more groups selected from H, halogen, hydroxyl, amino, nitro, cyano, $C_{1-6}$alkyl, $C_{1-4}$haloalkyl, —$CONH_2$, $C_{3-10}$cycloalkyl, 3-10-membered heterocyclic group, $C_{6-14}$aryl and 5-14-membered heteroaryl;

$R_d$ is selected from the following substituents: $H_2NCH_2$—, $H_2NCH_2CH_2$—, $H_2N(CH_2)_2CH_2$—, $H_2N(CH_2)_3CH_2$—, $H_2N(CH_2)_4CH_2$—, $H_2N(CH_2)_5CH_2$—, $H_2NC(=NH)CH_2$—, $H_2NC(=NH)NHCH_2$—, $H_2NC(=NH)NHCH_2CH_2$—, $H_2N(CH_2)NH(CH_2)_2CH_2$—, $H_2NC(=NH)NH(CH_2)_3CH_2$—,

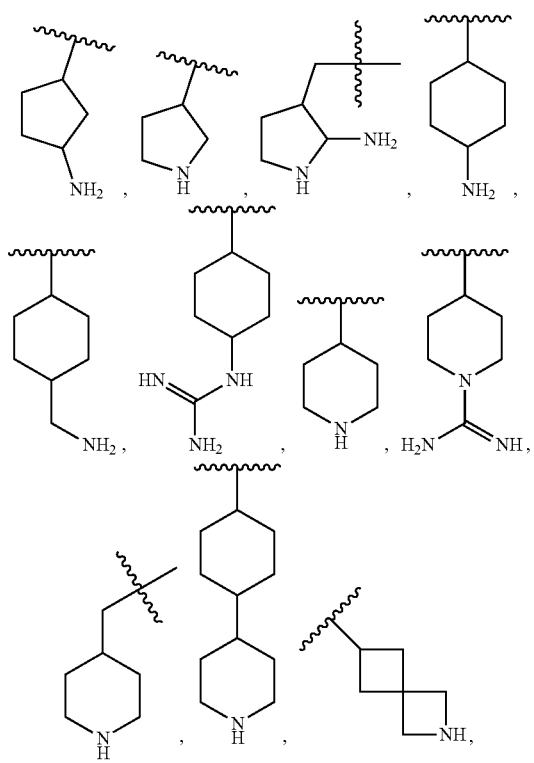

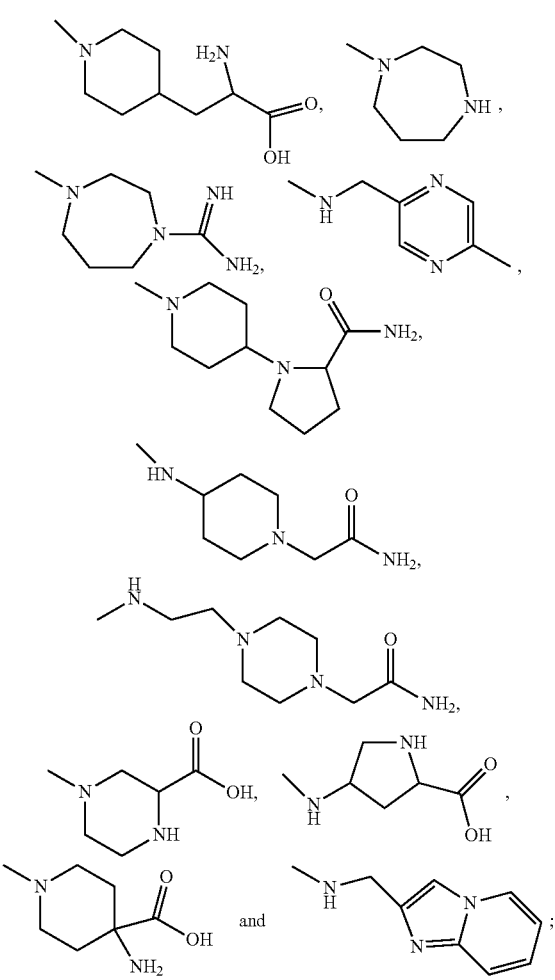

each of the substituents is optionally substituted with one or more H or $C_{1-4}$alkyl;

$R^2$ is H;

$R^1$ is selected from:

at least one group of $R_d$ and $R^1$ is substituted with one or more W groups;

wherein, the W group is selected from: —$(CH_2)_nOH$, $HOCH_2(CHOH)_nCH_2$—, $(HOCH_2)_2CH$—, $(HOCH_2)_3C$—, —$(CH_2)_nNH_2$, $C_{3-6}$monosaccharide, polysaccharide composed of 2-20, preferably 2-10, particularly preferably 2-5 same or different $C_{3-6}$monosaccharide, and $R^3O(CH_2CH_2O)_mCH_2CH_2$;

$R^3$ is selected from H and $C_{1-4}$alkyl;

n is an integer selected from 1-8, preferably 1-5, particularly preferably 1-3; and, m is an integer selected from 0-100, preferably 0-50, particularly preferably 0-20.

In some preferred embodiments, the compound according to the invention has a structure of Formula (II)-1:

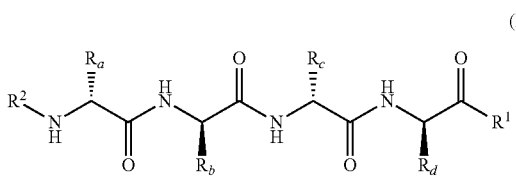

(II)-1 wherein, $R_d$ and/or $R^1$ is substituted with one or more W groups, $R_a$, $R_b$, $R_c$, $R_d$, $R^1$, $R^2$ and the W group have the same meanings as defined above.

In some preferred embodiments, $R_d$ is substituted with one W group.

In some preferred embodiments, the group formed by the substitution of $R_d$ with one W group is as described above.

In some preferred embodiments, $R_d$ is substituted with two W groups.

In some preferred embodiments, the group formed by the substitution of $R_d$ with two W groups is as described above.

In some preferred embodiments, $R^1$ is substituted with one W group.

In some preferred embodiments, the group formed by the substitution of $R^1$ with one W group is as described above.

In the preferred embodiments, the invention provides a compound, or a stereoisomer, a crystalline polymorph, a solvate, a metabolite, a prodrug or a pharmaceutically acceptable salt or ester thereof, wherein the compound has a structure of Formula (III):

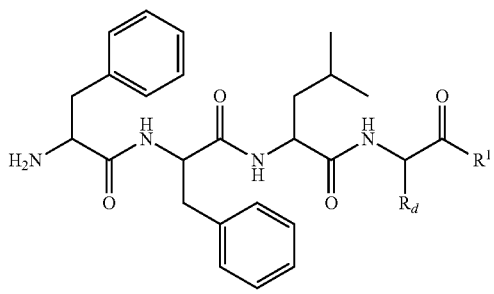

(III)

wherein, $R_d$ and/or $R^1$ is substituted with one or more W, $R_d$, $R^1$ and the W group have the same meanings as defined above.

In some preferred embodiments, $R_d$ is substituted with one W group.

In some preferred embodiments, the group formed by the substitution of $R_d$ with one W group is as described above.

In some preferred embodiments, $R_d$ is substituted with two W groups.

In some preferred embodiments, the group formed by the substitution of $R_d$ with two W groups is as described above.

In some preferred embodiments, $R^1$ is substituted with one W group.

In some preferred embodiments, the group formed by the substitution of $R^1$ with one W group is as described above.

In some preferred embodiments, the compound according to the invention has a structure of Formula (III)-1:

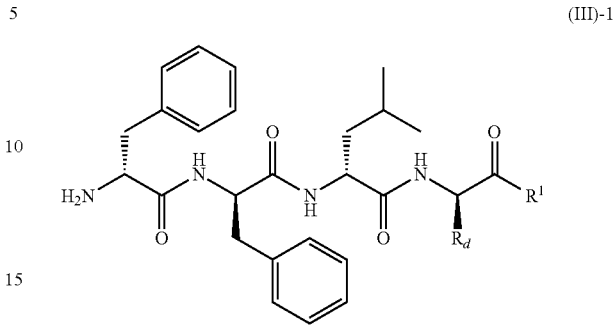

(III)-1 wherein, $R_d$ and/or $R^1$ is substituted with one or more W, $R_d$, $R^1$ and the W group have the same meanings as defined above.

In some preferred embodiments, $R_d$ is substituted with one W group.

In some preferred embodiments, the group formed by the substitution of $R_d$ with one W group is as described above.

In some preferred embodiments, $R_d$ is substituted with two W groups.

In some preferred embodiments, the group formed by the substitution of $R_d$ with two W groups is as described above.

In some preferred embodiments, $R^1$ is substituted with one W group.

In some preferred embodiments, the group formed by the substitution of $R^1$ with one W group is as described above.

In some preferred embodiments, the invention provides a compound, or a stereoisomer, a crystalline polymorph, a solvate, a metabolite, a prodrug or a pharmaceutically acceptable salt or ester thereof, the compound has a structure of Formula (IV):

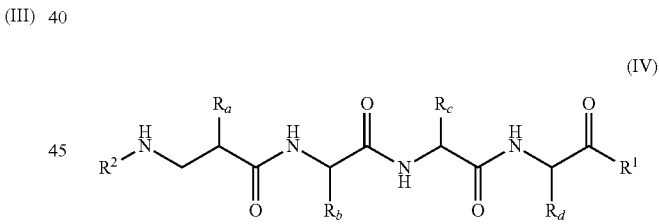

(IV)

wherein, $R_d$ and/or $R^1$ is substituted with one or more W, $R_a$, $R_b$, $R_c$, $R_d$, $R^1$, $R^2$ and the W group have the same meanings as defined above.

In some preferred embodiments, $R_d$ is substituted with one W group.

In some preferred embodiments, the group formed by the substitution of $R_d$ with one W group is as described above.

In some preferred embodiments, $R_d$ is substituted with two W groups.

In some preferred embodiments, the group formed by the substitution of $R_d$ with two W groups is as described above.

In some preferred embodiments, $R^1$ is substituted with one W group.

In some preferred embodiments, the group formed by the substitution of $R^1$ with one W group is as described above.

In some preferred embodiments, the compound according to the invention has a structure of Formula (IV)-1:

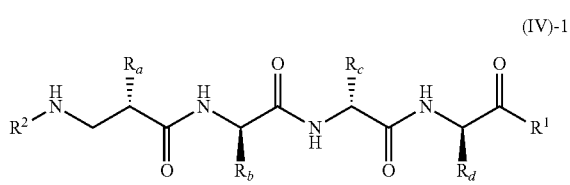

(IV)-1 wherein, $R_d$ and/or $R^1$ is substituted with one or more W, $R_a$, $R_b$, $R_c$, $R_d$, $R^1$, $R^2$ and the W group have the same meanings as defined above.

In some preferred embodiments, $R_d$ is substituted with one W group.

In some preferred embodiments, the group formed by the substitution of $R_d$ with one W group is as described above.

In some preferred embodiments, $R_d$ is substituted with two W groups.

In some preferred embodiments, the group formed by the substitution of $R_d$ with two W groups is as described above.

In some preferred embodiments, $R^1$ is substituted with one W group.

In some preferred embodiments, the group formed by the substitution of $R^1$ with one W group is as described above.

In some preferred embodiments, the invention provides a compound of Formula (I), (I)-1, (II), (II)-1, (III), (III)-1, (IV) or (IV)-1, or a stereoisomer, a crystalline polymorph, a solvate, a metabolite thereof, a prodrug or a pharmaceutically acceptable salt or ester thereof, wherein $R_d$ is selected from the following substituents: $H_2NCH_2$—, $H_2NCH_2CH_2$—, $H_2N(CH_2)_2CH_2$—, $H_2N(CH_2)_3CH_2$—, $H_2N(CH_2)_4CH_2$—, $H_2N(CH_2)_5CH_2$—, $H_2NC(=NH)CH_2$—, $H_2NC(=NH)NHCH_2$—, $H_2NC(=NH)NHCH_2CH_2$—, $H_2NC(=NH)NH(CH_2)_2CH_2$— and $H_2NC(=NH)NH(CH_2)_3CH_2$—; and, $R_d$ is substituted with one or more W groups, wherein the W group has the same meanings as defined above.

In the preferred embodiments, the invention provides a compound of Formula (I), (I)-1, (II), (II)-1, (III), (III)-1, (IV) or (IV)-1, or a stereoisomer, a crystalline polymorph, a solvate, a metabolite thereof, a prodrug or a pharmaceutically acceptable salt or ester thereof, wherein $R_d$ is selected from the following substituents: $H_2NCH_2$—, $H_2NCH_2CH_2$—, $H_2N(CH_2)_2CH_2$—, $H_2N(CH_2)_3CH_2$—, $H_2N(CH_2)_4CH_2$— and $H_2N(CH_2)_5CH_2$—; and $R_d$ is substituted with one or more W groups, wherein the W group has the same meanings as defined above.

In the preferred embodiments, the invention provides a compound of Formula (I), (I)-1, (II), (II)-1, (III), (III)-1, (IV) or (IV)-1, or a stereoisomer, a crystalline polymorph, a solvate, a metabolite thereof, a prodrug or a pharmaceutically acceptable salt or ester thereof, wherein the group formed by the substitution of $R_d$ with a W group is W—NH(CH_2)_3CH_2$—; and, the W group has the same meanings as defined above.

In some preferred embodiments, the group formed by the substitution of $R_d$ with a W group is W—NH(CH_2)_3CH_2$—, wherein W is selected from —$CH_2OH$, —$(CH_2)_2OH$, $HOCH_2CH(OH)CH_2$—, $(HOCH_2)_2CH$—, —$CH_2NH_2$, —$(CH_2)_2NH_2$, —$(CH_2)_3NH_2$, $CH_3O(CH_2CH_2O)CH_2CH_2$—, $CH_3O(CH_2CH_2O)_2CH_2CH_2$—, $CH_3O(CH_2CH_2O)_6CH_2CH_2$—, $CH_3O(CH_2CH_2O)_{11}CH_2CH_2$—, —$CH_2COOH$ and —$CH_2C(O)NH_2$.

In some preferred embodiments, the group formed by the substitution of $R_d$ with a W group is W—NH(CH_2)_3CH_2$—, wherein W is selected from —$CH_2OH$, —$(CH_2)_2OH$, $HOCH_2(CHOH)CH_2$—, $(HOCH_2)_2CH$—, —$CH_2NH_2$, —$(CH_2)_2NH_2$, —$(CH_2)_3NH_2$, $CH_3O(CH_2CH_2O)CH_2CH_2$—, $CH_3O(CH_2CH_2O)_2CH_2CH_2$—, $CH_3O(CH_2CH_2O)_6CH_2CH_2$— and $CH_3O(CH_2CH_2O)_{11}CH_2CH_2$—.

In the preferred embodiments, the invention provides a compound of Formula (I), (I)-1, (II), (II)-1, (III), (III)-1, (IV) or (IV)-1, or a stereoisomer, a crystalline polymorph, a solvate, a metabolite thereof, a prodrug or a pharmaceutically acceptable salt or ester thereof, wherein, $R^1$ is selected from:

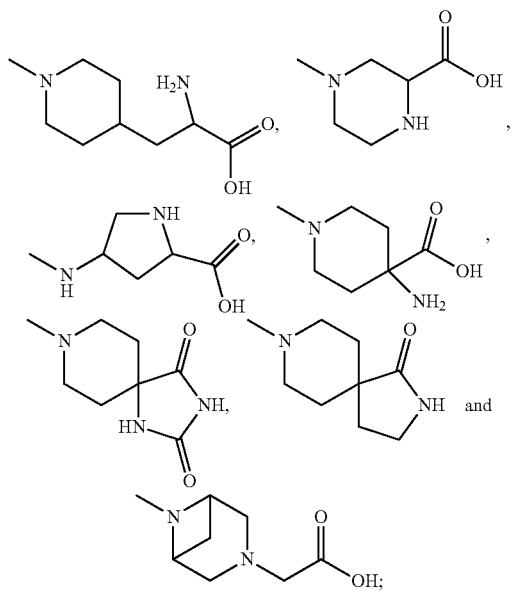

and, $R^1$ is substituted with one or more W groups, and the W group has the same meanings as defined above.

In the preferred embodiments, the invention provides a compound of Formula (I), (I)-1, (II), (II)-1, (III), (III)-1, (IV) or (IV)-1, or a stereoisomer, a crystalline polymorph, a solvate, a metabolite thereof, a prodrug or a pharmaceutically acceptable salt or ester thereof, wherein, $R^1$ is selected from:

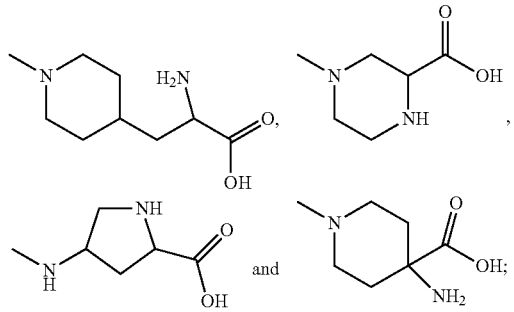

$R^1$ is substituted with one or more W groups, and the W group has the same meanings as defined above.

In the preferred embodiments, the invention provides a compound of Formula (I), (I)-1, (II), (II)-1, (III), (III)-1, (IV) or (IV)-1, or a stereoisomer, a crystalline polymorph, a solvate, a metabolite thereof, a prodrug or a pharmaceutically acceptable salt or ester thereof, wherein the group formed by the substitution of R¹ with a W group is

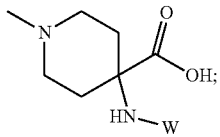

and, the W group has the same meanings as defined above.

In some preferred embodiments, the group formed by the substitution of R¹ with a W group is

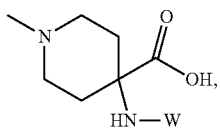

wherein the W group is selected from —CH₂OH, —(CH₂)₂OH, HOCH₂CH(OH)CH₂—, (HOCH₂)₂CH—, —CH₂NH₂, —(CH₂)₂NH₂, —(CH₂)₃NH₂, CH₃O(CH₂CH₂O)CH₂CH₂—, CH₃O(CH₂CH₂O)₂CH₂CH₂—, CH₃O(CH₂CH₂O)₆CH₂CH₂—, CH₃O(CH₂CH₂O)₁₁CH₂CH₂—, —CH₂COOH and —CH₂C(O)NH₂.

In some preferred embodiments, the group formed by the substitution of R¹ with a W group is

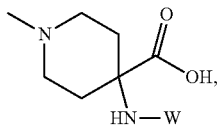

wherein the W group is selected from —CH₂OH, —(CH₂)₂OH, HOCH₂(CHOH)CH₂—, (HOCH₂)₂CH—, —CH₂NH₂, —(CH₂)₂NH₂, —(CH₂)₃NH₂, CH₃O(CH₂CH₂O)CH₂CH₂—, CH₃O(CH₂CH₂O)₂CH₂CH₂—, CH₃O(CH₂CH₂O)₆CH₂CH₂— and CH₃O(CH₂CH₂O)₁₁CH₂CH₂—.

In some preferred embodiments, the group formed by the substitution of R¹ with a W group is

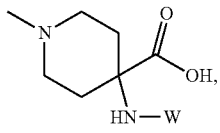

wherein the W group is selected from CH₃O(CH₂CH₂O)CH₂CH₂—, CH₃O(CH₂CH₂O)₂CH₂CH₂—, CH₃O(CH₂CH₂O)₆CH₂CH₂— and CH₃O(CH₂CH₂O)₁₁CH₂CH₂—.

The invention covers the compounds obtained by the combination of each options.

In the preferred embodiments, the invention provides a compound or a pharmaceutically acceptable salt or ester, a stereoisomer, a crystalline polymorph, a solvate, a metabolite, or a prodrug thereof, wherein the compound is selected from:

4-amino-1-((R)-2-((R)-2-((R)-2-((R)-2-amino-3-phenylpropanamido)-3-phenylpropanamido)-4-methylpentanamido)-6-(((R)-2,3-dihydroxypropyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-(((S)-2,3-dihydroxypropyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((2-aminoethyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((3-aminopropyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((2-(2-methoxyethoxy)ethyl)amino)hexanoyl)piperidin-4-carboxylic acid;

4-amino-1-((R)-28-((R)-2-((R)-2-((R)-2-amino-3-phenylpropanamido)-3-phenylpropanamido)-4-methylpentanamido)-2,5,8,11,14,17,20-heptaoxa-23-azanonacosan-29-oyl)piperidin-4-carboxylic acid;

4-amino-1-((R)-43-((R)-2-((R)-2-((R)-2-amino-3-phenylpropanamido)-3-phenylpropanamido)-4-methylpentanamido)-2,5,8,11,14,17,20,23,26,29,32,35-dodeoxa-38-azatetratetracontan-4 4-oyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((1,3-dihydroxypropan-2-yl)amino)hexanoyl)piperidin-4-carboxylic acid;

1-((R)-6-amino-2-((R)-2-((R)-2-amino-3-phenylpropanamido)-3-phenylpropanamido)-4-methylpentanamido)hexanoyl)-4-((3-aminopropyl)amino)piperidin-4-carboxylic acid;

1-((R)-6-amino-2-((R)-2-((R)-2-amino-3-phenylpropanamido)-3-phenylpropanamido)-4-methylpentanamido) hexanoyl)-4-(((R)-2,3-dihydroxypropyl)amino)piperidin-4-carboxylic acid;

1-((R)-6-amino-2-((R)-2-((R)-2-amino-3-phenylpropanamido)-3-phenylpropanamido)-4-methylpentanamido)hexanoyl)-4-((2-aminoethyl)amino)piperidin-4-carboxylic acid;

1-((R)-6-amino-2-((R)-2-((R)-2-amino-3-phenylpropanamido)-3-phenylpropanamido)-4-methylpentanamido) hexanoyl)-4-((2-(2-methoxyethoxy)ethyl)amino)piperidin-4-carboxylic acid;

4-(2,5,8,11,14,17,20-heptaoxadocosan-22-ylamino)-1-((R)-6-amino-2-((R)-2-((R)-2-((R)-2-amino-3-phenylpropanamido)-3-phenylpropanamido)-4-methylpentanamido)hexanoyl)piperidin-4-carboxylic acid;

4-(2,5,8,11,14,17,20,23,26,29,32,35-dodecaoxaheptatriacontan-37-ylamino)-1-((R)-6-amino-2-((R)-2-((R)-2-((R)-2-amino-3-phenylpropanamido)-3-phenylpropanamido)-4-methylpentanamido)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-(di(2-(2-methoxyethoxy)ethyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-(di(carboxymethyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((carboxymethyl)amino)hexanoyl)piperidin-4-carboxylic acid;

4-amino-1-((R)-2-((R)-2-((R)-2-((R)-2-(2-aminoethylamino)-3-phenylpropionyl)-3-phenylpropionyl)-4-methylpentanamido)-6-aminohexanoyl)piperidin-4-carboxylic acid;

1-((R)-2-((R)-2-((R)-2-((R)-2-(3-aminopropylamino)-3-phenylpropionyl)-3-phenylpropionyl)-4-methylpentanamido)-6-aminohexanoyl)-4-aminopiperidin-4-carboxylic acid;

4-amino-1-((3R,6R,9R,12R)-12-(4-aminobutyl)-3,6-dibenzyl-1-carboxyl-9-isobutyl-4,7,10-trioxo-2,5,8,11-tetraaza tridecan-13-oyl)piperidin-4-carboxylic acid;

4-amino-1-((R)-6-amino-2-((R)-2-((R)-2-((S)-3-amino-2-benzylpropanamido)-3-phenylpropanamido)-4-methylpentanamido)hexanoyl)piperidin-4-carboxylic acid;

4-amino-1-((R)-6-amino-2-((R)-2-((R)-2-((R)-3-amino-2-benzylpropanamido)-3-phenylpropanamido)-4-methylpentanamido)hexanoyl)piperidin-4-carboxylic acid;

8-((R)-2-((R)-2-((R)-2-((R)-2-amino-3-phenylpropanamido)-3-phenylpropanamido)-4-methylpentanamido)-6-(2-(methoxyethoxy)ethylamino)hexanoyl)-2,8-diazaspiro[4.5]decan-3-one;

8-((R)-2-((R)-2-((R)-2-((R)-2-amino-3-phenylpropanamido)-3-phenylpropanamido)-4-methylpentanamido)-6-(2-(methoxyethoxy)ethylamino)hexanoyl)-1,3,8-triazaspiro[4.5]decane-2,4-dione;

2-(6-((R)-2-((R)-2-((R)-2-((R)-2-amino-3-phenylpropanamido)-3-phenylpropanamido)-4-methylpentanamido)-6-((2-(2-methoxyethoxy)ethyl)amino)hexanoyl)-3,6-diazabicyclo[3.1.1]heptan-3-yl)acetic acid; and 4-amino-1-((R)-6-(((2-amino-2-oxoethyl)amino)-2-((R)-2-((R)-2-((R)-2-amino-3-phenylpropanamido)-3-phenylpropanamido)-4-methylpentanamido)hexanoyl)piperidin-4-carboxylic acid.

Preparation Method

In another aspect, the invention provides a method for preparing the compound of Formula (I) of the invention, which is selected from the following methods:

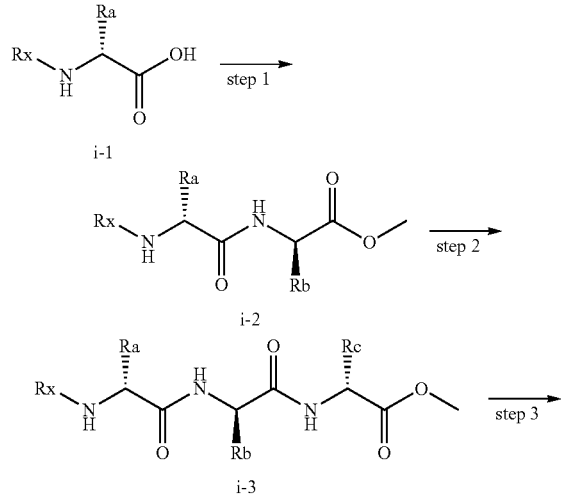

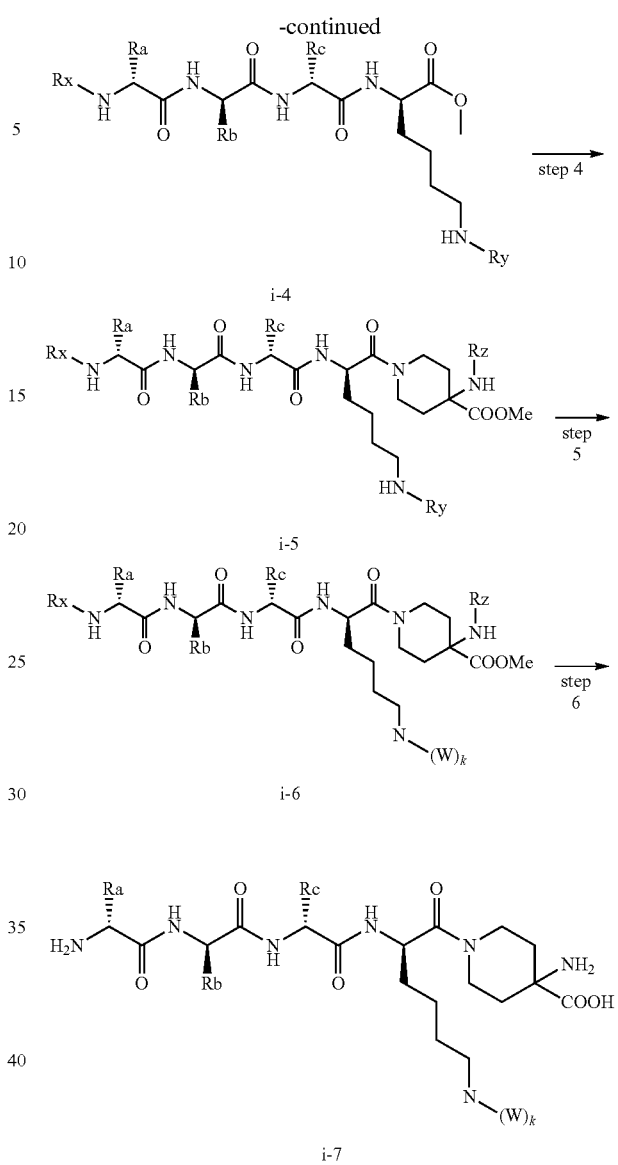

Step 1: a compound of general formula i-1 and an α-amino ester are subjected to condensation reaction thereby obtaining a compound of general formula i-2;

Step 2: the compound of general formula i-2 is subjected to hydrolysis reaction and condensation reaction thereby obtaining a compound of general formula i-3;

Step 3: the compound of general formula i-3 is subjected to hydrolysis reaction and condensation reaction thereby obtaining a compound of general formula i-4;

Step 4: the compound of general formula i-4 is subjected to hydrolysis reaction and condensation reaction thereby obtaining a compound of general formula i-5;

Step 5: the protecting group Ry is selectively removed from the compound of general formula i-5 and the W group is introduced thereby obtaining a compound of general formula i-6; and Step 6: the compound of general formula i-6 is subjected to hydrolysis reaction and deprotection reaction thereby obtaining a compound of general formula i-7;

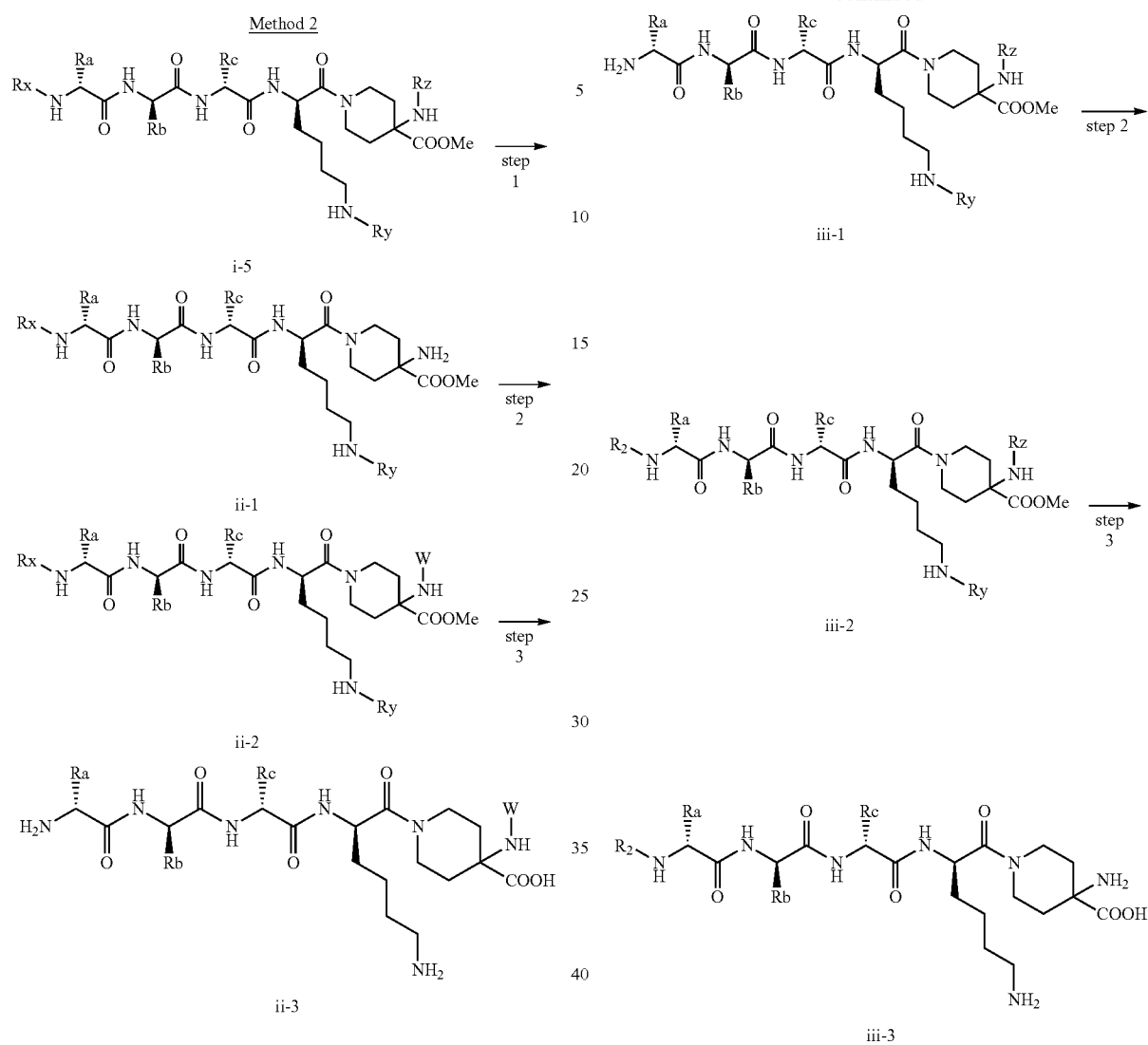

Step 1: the protecting group Rz is selectively removed from the compound of general formula i-5 thereby obtaining a compound of general formula ii-1;

Step 2: the W group is introduced into the compound of general formula ii-1 thereby obtaining a compound of general formula ii-2; and Step 3: the compound of general formula ii-2 is subjected to hydrolysis reaction and deprotection reaction thereby obtaining a compound of general formula ii-3;

Step 1: the protecting group Rx is selectively removed from a compound of general formula i-5 thereby obtaining a compound of general formula iii-1;

Step 2: the $R_2$ group is introduced into the compound of general formula iii-1 thereby obtaining a compound of general formula iii-2; and Step 3: the compound of general formula iii-2 is subjected to hydrolysis reaction and deprotection reaction thereby obtaining a compound of general formula iii-3;

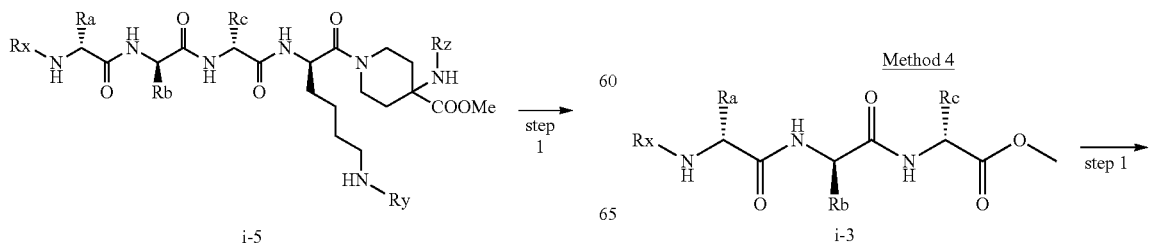

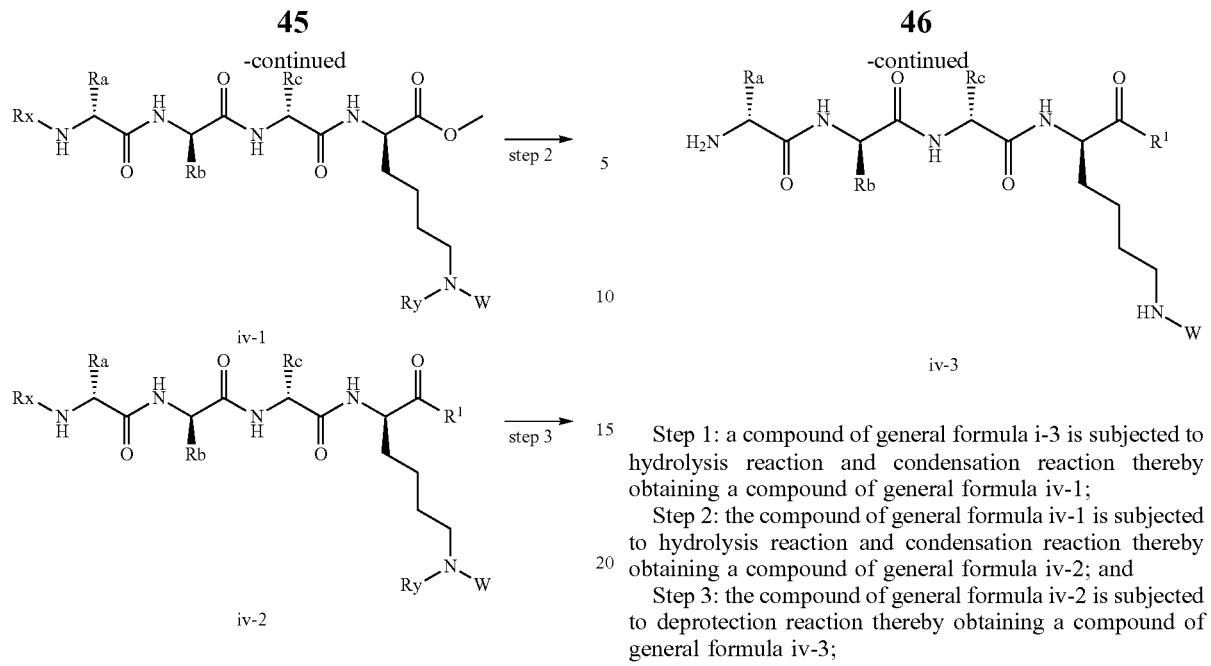

Step 1: a compound of general formula i-3 is subjected to hydrolysis reaction and condensation reaction thereby obtaining a compound of general formula iv-1;

Step 2: the compound of general formula iv-1 is subjected to hydrolysis reaction and condensation reaction thereby obtaining a compound of general formula iv-2; and Step 3: the compound of general formula iv-2 is subjected to deprotection reaction thereby obtaining a compound of general formula iv-3;

Method 5

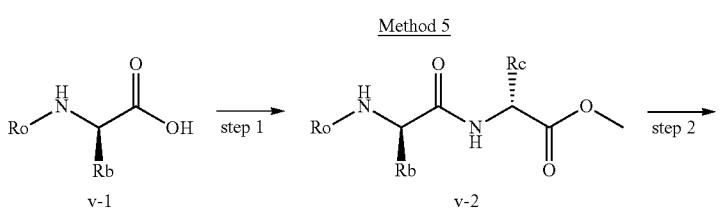

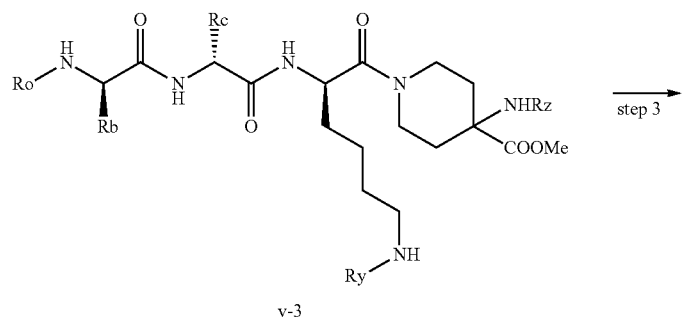

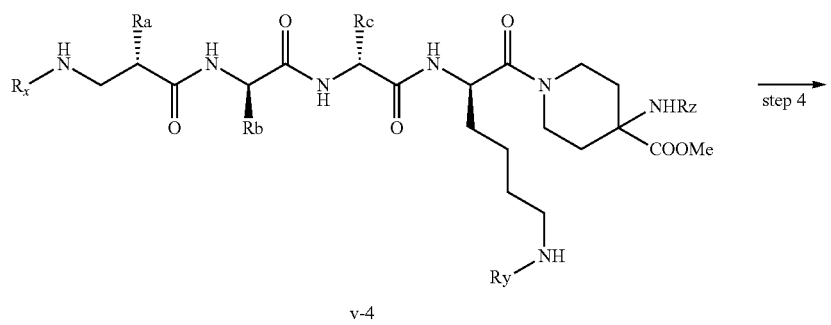

-continued

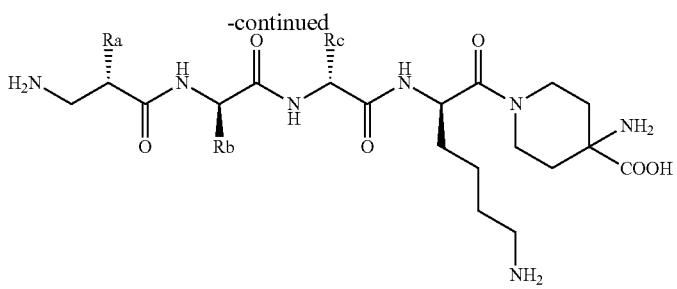

v-5

Step 1: a compound of general formula v-1 is subjected to condensation reaction thereby obtaining a compound of general formula v-2;

Step 2: the compound of general formula v-2 is subjected to hydrolysis reaction and condensation reaction thereby obtaining a compound of general formula v-3;

Step 3: the compound of general formula v-3 is subjected to selective removal of the protecting group Ro and condensation reaction thereby obtaining a compound of general formula v-4; and Step 4: the compound of general formula v-4 is subjected to hydrolysis reaction and deprotection reaction thereby obtaining a compound of general formula v-5;

wherein, Rx, Ry, Rz, and Ro are amino-protecting groups, and are not completely the same, which include, but are not limited to alkoxycarbonyl, acyl and alkyl; for example, tert-butyloxycarbonyl, benzyloxycarbonyl, benzyl, fluorenylmethoxycarbonyl,

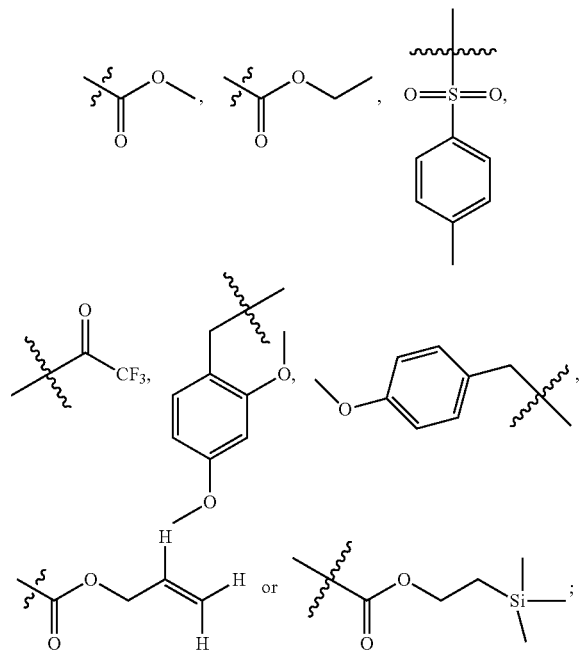

k is 1 or 2; the other groups have the same meanings as defined above.

In some preferred embodiments, one or two W groups can be introduced by adjusting the molar ratio of the substrates in Step 5 of Method 1.

In some preferred embodiments, the condensation reaction is conducted as follows: a substrate is dissolved in a solvent (including, but not limited to dichloromethane, tetrahydrofuran, N,N-dimethyllformamide, N-methylpyrrolidinone, dimethyl sulfoxide, either alone or in combination), a condensation agent (including, but not limited to: HATU, HBTU, EDCl, PyBOP, CDI, HOBT), an adjuvant (including, but not limited to copper dichloride, copper dichloride dihydrate, other hydrates of copper dichloride) and a base (including, but not limited to an organic base and an inorganic base, preferably N,N-diisopropylethylamine, N-methylmorpholine, 4-dimethylaminopyridine) are added at a suitable temperature (−30° C.-30° C.); and the resultant mixture is reacted with a corresponding α-amino ester for a suitable period of time, thereby affording a high optical pure target.

In some preferred embodiments, the hydrolysis reaction is conducted as follows: a substrate is dissolved in a solvent (including, but not limited to tetrahydrofuran, methanol, ethanol, water, acetone, ethyl ether, methyl tert-butyl ether, either alone or in combination), and reacted with a base (including, but not limited to an organic base or an inorganic base, preferably lithium hydroxide, sodium hydroxide, potassium hydroxide) at a suitable temperature (−30° C.-30° C.), thereby affording the corresponding hydrolysis product.

In some preferred embodiments, the W group can be introduced by reductive amination of a substrate and a corresponding aldehyde, acetal, or hemiacetal (the reducing agent includes, but are not limited to sodium borohydride, potassium borohydride, borane, sodium cyanoborohydride, sodium triacetoxyborohydride, etc.); or can be introduced by alkylation reaction of a corresponding halide or an active ester of a corresponding alcohol (including, but not limited to p-toluenesulfonate, methanesulfonate, trifluoromethanesulfonate, etc.), particularly preferably by reductive amination of a substrate and a corresponding aldehyde, acetal, or hemiacetal.

In some preferred embodiments, the deprotection reaction is performed in the presence of a deprotecting agent at room temperature or under heating. The preferred deprotecting agent includes hydrogen, an acid agent such as trifluoroacetic acid, hydrochloric acid, or sulphuric acid, or a base agent such as sodium hydroxide, potassium hydroxide, lithium hydroxide, and piperidine. By referencing to the textbooks in the art, for example, Greene's Protective Groups in Organic Synthesis (4th Edition), etc., a person skilled in the art can choose and carry out proper operations to selectively or completely remove one or more protecting groups.

A Pharmaceutical Composition and a Therapeutic Method

In another aspect, the invention provides a pharmaceutical composition, comprising a prophylactically or therapeutically effective amount of the compound, or the stereoisomer, the crystalline polymorph, the solvate, the metabolite, the prodrug or the pharmaceutically acceptable salt or ester thereof according to the invention, and one or more pharmaceutically acceptable carriers. In another embodiment, the pharmaceutical composition may further comprise one or more additional therapeutic agents, such as therapeutic agents for preventing or treating a disease associated with κ-opioid receptor.

In the invention, the term "a pharmaceutically acceptable carrier" refers to a diluent, adjuvant, excipient or vehicle, together with which a therapeutic agent is administered. The carrier is suitable for contacting the tissue of human and/or other animal in a reasonable range as medically judged, without excessive toxicity, irritation, allergic reaction or other problems or complications within a reasonable benefit/risk ratio.

The pharmaceutically acceptable carrier, which can be used in the pharmaceutical composition of the invention, include, but are not limited to sterile liquids such as water and oil, including those derived from petroleum, animal and vegetable or synthetic oil, such as peanut oil, soybean oil, mineral oil, and sesame oil. When the pharmaceutical composition is administered intravenously, water is an exemplary carrier. Physiological saline, an aqueous solution of glucose or glycerin can also be used as a liquid carrier, particularly for injection. Suitable pharmaceutical excipients include starch, glucose, lactose, sucrose, gelatin, maltose, chalk, silica gel, sodium stearate, glyceryl monostearate, talc, sodium chloride, skimmed milk powder, glycerin, propylene glycol, water, ethanol and the like. The composition may also comprise a small amount of wetting agent, an emulsifying agent or a pH buffering agent, if necessary. An oral formulation may comprise a standard carrier such as pharmaceutical-grade mannitol, lactose, starch, magnesium stearate, sodium saccharin, cellulose, and magnesium carbonate. Examples of suitable pharmaceutically acceptable carriers are those as described in Remington's Pharmaceutical Sciences (1990).

The pharmaceutical compositions of the invention can act systemically and/or topically. For this purpose, they can be administered in a suitable route, for example by injection, intravenous, intraarterial, subcutaneous, intraperitoneal, intramuscular or transdermal administration; or be administered orally, buccally, nasally, transmucosally, topically, in the form of an ophthalmic preparation or by inhalation.

For these administration routes, the pharmaceutical composition of the invention may be administered in a suitable dosage form.

The dosage form includes, but is not limited to, a tablet, a capsule, a troche, a hard sugar agent, a powder, a spray, a cream, an ointment, a suppository, a gel, a paste, a lotion, an ointment, an aqueous suspension, an injectable solution, an elixir, and a syrup.

The term "an effective amount" as used herein refers to an amount that alleviates one or more symptoms of a disease to be treated to some extent.

The administration regimen can be adjusted so as to provide the optimal response as desired. For example, a single bolus can be administered, several individual doses can be administered with time, or a dose can be proportionally decreased or increased as indicated according to the urgent need for treatment. It should be noted that the dose may be varied depending on the type and severity of the condition to be alleviated, and may include a single dose or multiple doses. It should be further understood that for any particular individual, the particular administration regimen should be adjusted with time depending on the individual's needs and the professional judgment made by the person who administers the composition or supervises the administration of the composition.

The administered amount of the compound of the invention would depend on the individual to be treated, the severity of the disease or condition, the rate of administration, the treatment of the compound, and the judgment made by a physician. In general, the effective dose is from about 0.0001 to about 50 mg per kg body weight per day, for example from about 0.01 to about 10 mg/kg/day (administered once or for several times). For a 70 kg person, it will be about 0.007 mg/day to about 3500 mg/day, for example from about 0.7 mg/day to about 700 mg/day. In some cases, a dose, which is not higher than the lower limit of the above-mentioned range, may be sufficient, however, in other cases, a larger dose may be used when no adverse side effects are caused, provided that the larger dose is first divided into several smaller doses for administration within a day.

The content or amount of the compound of the invention in a pharmaceutical composition may be about 0.01 mg to about 1000 mg, suitably 0.1-500 mg, preferably 0.5-300 mg, more preferably 1-150 mg, particularly preferably 1-50 mg, e.g. 1.5 mg, 2 mg, 4 mg, 10 mg, 25 mg, etc.

Unless otherwise specified, the term "treating" as used herein refers to reversing, alleviating, or inhibiting a disease or condition to which such a term is applied, or the progression of one or more symptoms of such a disease or condition, or preventing such a disease or condition or one or more symptoms of such a disease or condition.

As used herein, the term "individual" includes a human or non-human animal. Exemplary human individuals include a human (referred to as a patient) having a disease (e.g. a disease as described herein) or a normal individual. The "non-human animal" in the invention includes all the vertebrates, such as non-mammals (e.g. birds, amphibians, and reptiles), and mammals, such as non-human primates, livestock and/or domesticated animals (e.g. sheep, dogs, cats, cows, pigs, etc.).

In another embodiment, the pharmaceutical composition of the invention further comprises one or more additional therapeutic agents or prophylactic agents, including, but not limited to other opioid receptor agonists (e.g. morphine, fentanyl, oxymorphone or oxycodone), antidepressants, anticonvulsants, tranquilizers, antihistamines, ion channel blockers, non-steroidal anti-inflammatory drugs and diuretics, etc.

In another aspect, the invention provides use of the compound, or the stereoisomer, the crystalline polymorph, the solvate, the metabolite, the prodrug or the pharmaceutically acceptable salt or ester thereof according to the invention, or the pharmaceutical composition according to the invention in manufacture of a medicament for prevention or treatment of a disease associated with κ-opioid receptor.

In another aspect, the invention provides the compound of the invention or a pharmaceutical composition comprising the compound, for prevention or treatment of a disease associated with κ-opioid receptor.

In another aspect, the invention provides a method for preventing or treating a disease associated with κ-opioid receptor, comprising administering to an individual in need thereof an effective amount of the compound of the invention or a pharmaceutical composition comprising the compound.

In the invention, the disease associated with κ-opioid receptor is selected from pain, inflammation, itching, edema, hyponatremia, hypopotassaemia, intestinal obstruction, cough and glaucoma. the pain includes neuropathic pain, somatic pain, visceral pain, skin pain, arthritis pain, nephrolith pain, hysterotrismus, dysmenorrhea, endometriosis, post-surgical pain, pain after medical treatment, eye pain, otitis pain, cancer pain and pain associated with gastrointestinal dysfunction.

In another aspect, the invention provides use of the compound, or the stereoisomer, the crystalline polymorph, the solvate, the metabolite, the prodrug or the pharmaceutically acceptable salt or ester thereof according to the invention, or the pharmaceutical composition according to the invention in manufacture of an agent for enhancing the level or activity of κ-opioid receptor in a cell.

In some preferred embodiments, the cell is a cell line or a cell from a subject.

In some preferred embodiments, the compound, or the stereoisomer, the crystalline polymorph, the solvate, the metabolite, the prodrug or the pharmaceutically acceptable salt or ester thereof, or the pharmaceutical composition according to the invention is used in an in vivo method.

In some preferred embodiments, the compound, or the stereoisomer, the crystalline polymorph, the solvate, the metabolite, the prodrug or the pharmaceutically acceptable salt or ester thereof, or the pharmaceutical composition according to the invention is used in an in vitro method.

In another aspect, the invention provides the compound, or the stereoisomer, the crystalline polymorph, the solvate, the metabolite, the prodrug or the pharmaceutically acceptable salt or ester thereof according to the invention, or the pharmaceutical composition according to the invention, for use in enhancing the level or activity of κ-opioid receptor in a cell.

In some preferred embodiments, the cell is a cell line or a cell from a subject.

In some preferred embodiments, the compound, or the stereoisomer, the crystalline polymorph, the solvate, the metabolite, the prodrug or the pharmaceutically acceptable salt or ester thereof, or the pharmaceutical composition of the invention for use is used in an in vivo method.

In some preferred embodiments, the compound, or the stereoisomer, the crystalline polymorph, the solvate, the metabolite, the prodrug or the pharmaceutically acceptable salt or ester thereof, or the pharmaceutical composition of the invention for use is used in an in vitro method.

In another aspect, the invention provides a method for enhancing the level or activity of κ-opioid receptor in a cell, comprising administering to the cell an effective amount of The compound, or the stereoisomer, the crystalline polymorph, the solvate, the metabolite, the prodrug or the pharmaceutically acceptable salt or ester thereof according to the invention, or the pharmaceutical composition according to the invention.

In some preferred embodiments, the cell is a cell line or a cell from a subject.

In some preferred embodiments, the method is performed in vivo.

In some preferred embodiments, the method is performed in vitro.

Beneficial Technical Effects

The compound of the invention has a lesser ability of penetrating across the blood-brain barrier, and a lower capacity of entering the brain. In some preferred embodiments, the compound of the invention has a reduced toxicity to the central nervous system at a concentration effective to the peripheral analgesia, and has reduced toxic side effects to the central nervous system.

When the compound of the invention is administered to an individual in need thereof at a prophylactically or therapeutically effective concentration, it shows a low or no ability of penetrating across the blood-brain barrier. κ-opioid receptors (also referred to hereafter as κ receptors) are distributed in the peripheral tissues (including skin and body tissues) and viscera of human or other mammals. It is also found that κ receptors are also present in the brain. Activation of κ receptors in the peripheral tissues can lead to the inhibition of pain and inflammatory response, while activation of κ receptors in the brain can not only lead to a sedative effect, but also lead to severe dysphoria and hallucination. In some embodiments, when administered in an effective amount, the compound of the invention substantially shows no penetration across the blood-brain barrier, and thus minimizing to the largest extent or even completely eliminating the sedative and hallucinogenic, the side effects of which many other κ agonists having a certain ability of penetrating across the blood-brain barrier have.

It is surprisingly found that when administered at a dose of about 1 mg/kg, the compound of the invention can reach a high concentration in the peripheral plasma, and meanwhile has a very low concentration in the brain.

The compound of the invention has a higher $ED_{50}$ for the sedative effect than for the analgesic effect.

EXAMPLE

The invention is further described in the following examples, but these examples are not provided for the purpose of limiting the scope of the invention.

The abbreviations in the invention have the following meanings:

| Abbreviation | Meanings |
| --- | --- |
| AllocCl | Allyl chloroformate |
| DIEA | N,N-diisopropylethylamine |
| HBTU | O-benzotriazole-N,N,N',N'-tetramethyluronium hexafluorophosphate |
| HOBt | 1-hydroxybenzotriazole |

Example 1. 4-amino-1-((R)-2-((R)-2-((R)-2-((R)-2-amino-3-phenylpropanamido)-3-phenylpropanamido)-4-methylpentanamido)-6-(((R)-2,3-dihydroxypropyl)amino)hexanoyl)piperidin-4-carboxylic acid (Compound 1)

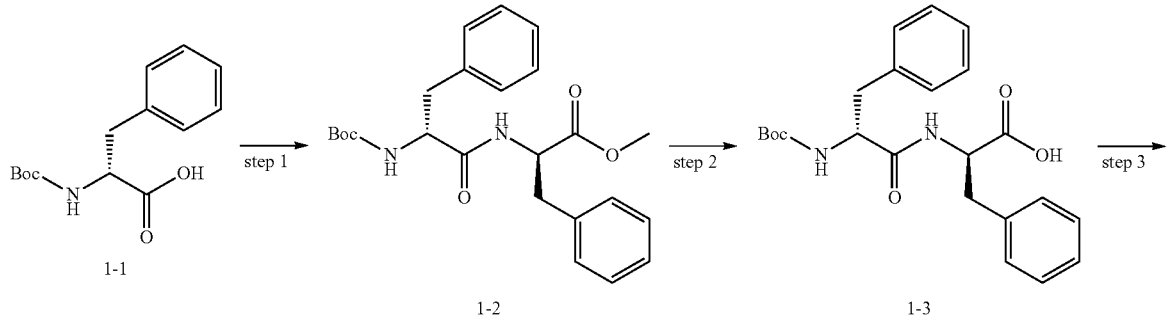

-continued
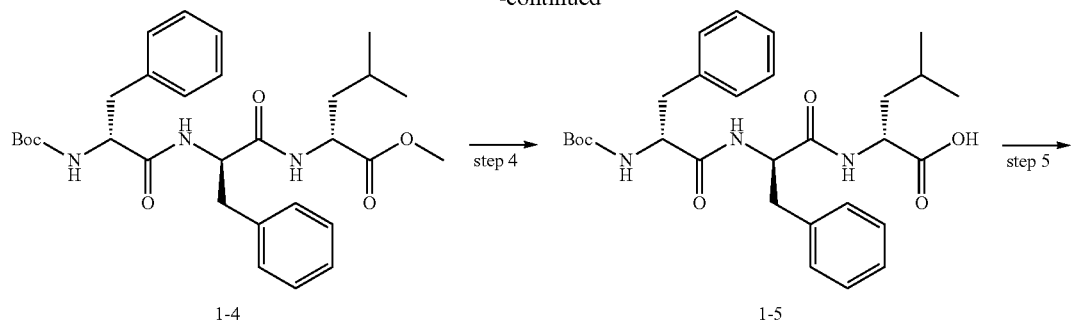
1-4 → step 4 → 1-5 → step 5
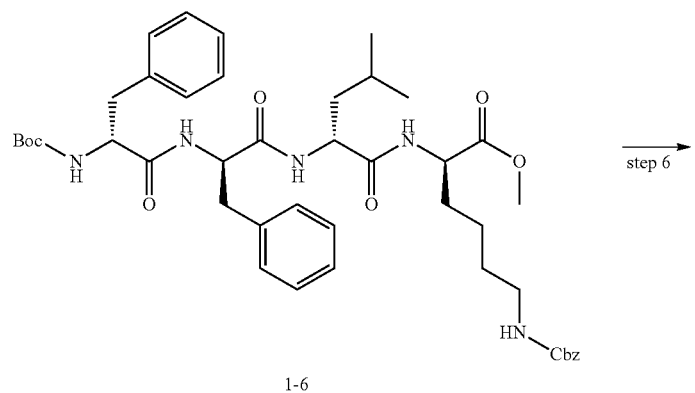
1-6 → step 6
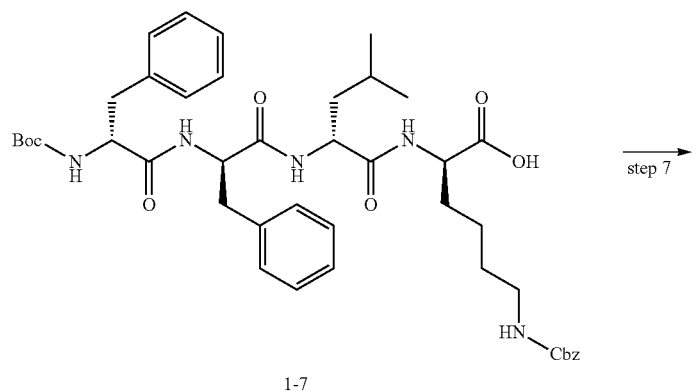
1-7 → step 7
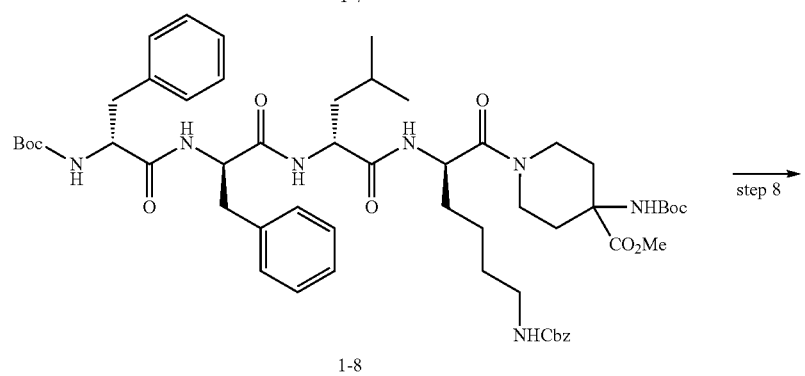
1-8 → step 8

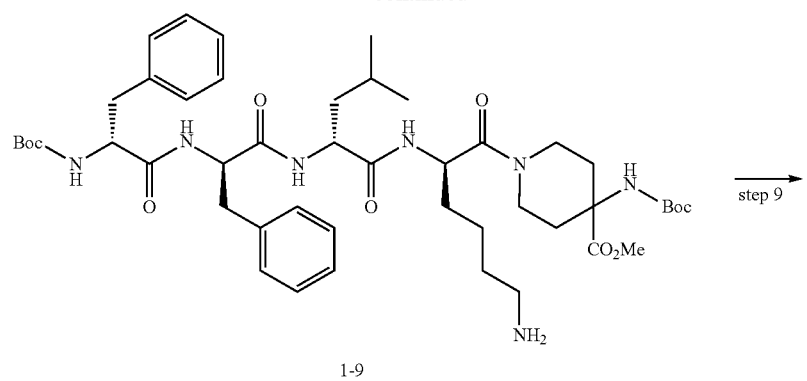
1-9
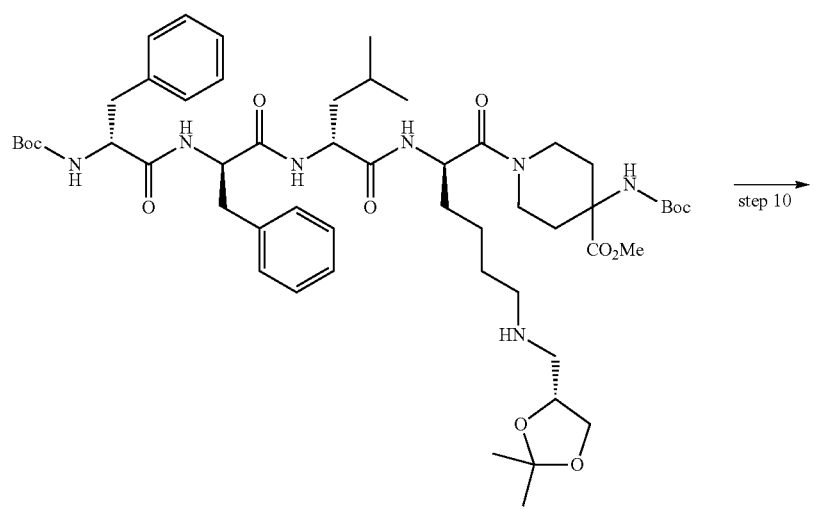
1-10
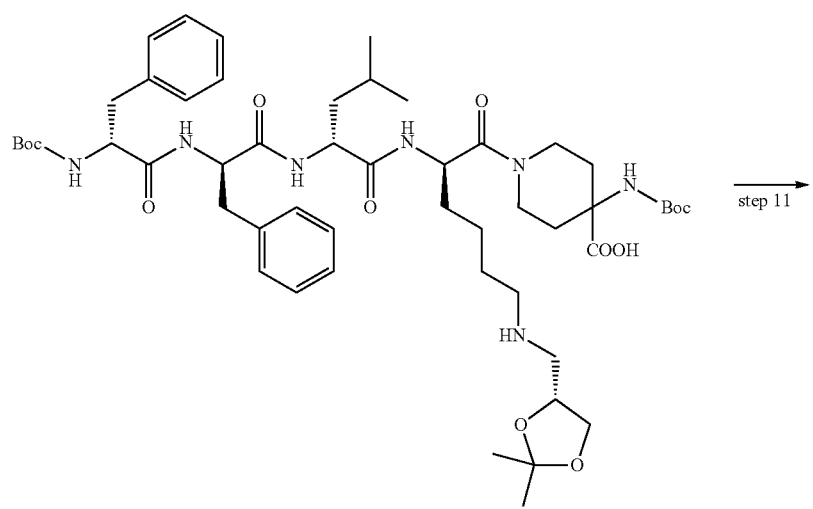
1-11

-continued

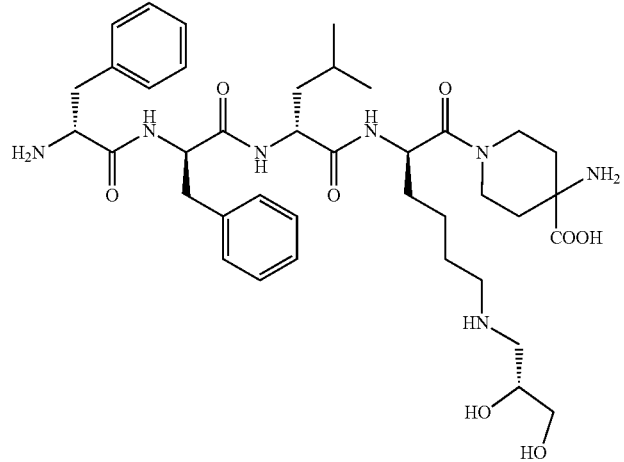 [SMILES: CC(C)C[C@@H](NC(=O)[C@@H](Cc1ccccc1)NC(=O)[C@H](N)Cc1ccccc1)C(=O)N[C@H](CCCCNC[C@H](O)CO)C(=O)N1CCC(N)(C(=O)O)CC1]

1

Step 1: Synthesis of methyl (R)-2-((R)-2-((tert-butoxycarbonyl)amino)-3-phenylpropanamido)-3-phenylpropanoate (1-2)

(R)-2-((tert-butoxycarbonyl)amino)-3-phenylpropionic acid (1-1) (20.00 g, 75.38 mmol), (R)-2-amino-3-phenylmethyl propionate (17.07 g, 79.15 mmol), N,N-diisopropylethylamine (31.18 g, 241.23 mmol) and copper chloride dihydrate (14.14 g, 82.92 mmol) were dissolved in tetrahydrofuran (200 mL). Under the protection of nitrogen, the resultant mixture was cooled to about 0° C., to which HOBt (12.22 g, 90.46 mmol) was added, followed by an addition of HBTU (34.31 g, 90.46 mmol). The reaction was carried out at room temperature overnight. The title compound (a crude product, 21.55 g) was obtained after workup, and used directly in the next step.
ESI-MS (m/z): 427 (M+H)$^+$.

Step 2: Synthesis of (R)-2-((R)-2-((tert-butoxycarbonyl)amino)-3-phenylpropanamido)-3-phenylpropionic acid (1-3)

Compound (1-2) (21.50 g, 50.4 mmol) was dissolved in tetrahydrofuran (300 mL) and water (60 mL), and the resultant mixture was cooled to about 0° C., to which lithium hydroxide monohydrate (4.65 g, 111 mmol) was added. The reaction was carried out at 0° C. for 2 h. The reactant was adjusted to pH=3 with hydrochloric acid. The title compound (a crude product, 27 g) was obtained after workup, and used directly in the next step.
ESI-MS (m/z): 413 (M+H)$^+$.

Step 3: Synthesis of methyl (R)-2-((R)-2-((R)-2-tert-butyloxycarbonylamino-3-phenylpropanamido)-3-phenylpropanamido)-4-methylvalerate (1-4)

Compound (1-3) (27.0 g, 50.4 mmol) and methyl (R)-2-amino-4-methylvalerate hydrochloride (9.62 g, 52.92 mmol) were dissolved in tetrahydrofuran (270 mL), and the resultant mixture was cooled to 0° C. Under the protection of nitrogen, N,N-diisopropylethylamine (20.85 g, 161.3 mmol), copper chloride dihydrate (9.45 g, 55.5 mmol) and HOBt (8.17 g, 60.5 mmol) were added, HBTU (22.9 g, 60.5 mmol) was added at last. The reaction was carried out overnight. Title compound (a crude product, 21.7 g) was obtained after workup, and used directly in the next step.
ESI-MS (m/z): 540 (M+H)$^+$.

Step 4: Synthesis of (R)-2-((R)-2-((R)-2-tert-butyloxycarbonylamino-3-phenylpropanamido)-3-phenylpropanamido)-4-methylvaleric acid (1-5)

Compound (1-4) (21.7 g, 40.21 mmol) was dissolved in tetrahydrofuran (310 mL) and water (62 mL). The resultant mixture was cooled to 0° C., to which lithium hydroxide monohydrate (3.7 g, 88.46 mmol) was added. The reaction was carried out at 0° C. for 1.5 h. The reactant was adjusted to pH=3 with hydrochloric acid. The title compound (a crude product, 22.32 g) was obtained after workup, and used directly in the next step.
ESI-MS (m/z): 526(M+H)$^+$.

Step 5: Synthesis of methyl (R)-2-((R)-2-((R)-2-((R)-2-tert-butyloxycarbonylamino-3-phenylpropanamido)-3-phenylpropanamido)-4-methylpentanamido)-6-benzyloxycarbonylamino hexanoate (1-6)

(R)-2-amino-6-benzyloxycarbonylaminomethyl hexanoate (10.75 g, 32.56 mmol) was dissolved in tetrahydrofuran (50 mL), and added with N,N-diisopropylethylamine (12.8 g, 99.2 mmol). The resultant mixture was stirred at room temperature for 30 min, and then Compound (1-5) (16.3 g, 31 mmol), HOBt (5.0 g, 37.2 mmol), copper chloride dihydrate (5.8 g, 34.1 mmol) and HBTU (14.1 g, 37.2 mmol) were added. Under the protection of nitrogen, the resultant reaction mixture was reacted at 0° C. overnight. Water (500 mL), dichloromethane (500 mL) and diatomite were added, and stirred for 5 min. The title compound (a crude product, 17 g) was obtained after workup, and used directly in the next step.
ESI-MS (m/z): 802 (M+H)$^+$.

Step 6: Synthesis of (R)-2-((R)-2-((R)-2-((R)-2-tert-butyloxycarbonylamino-3-phenylpropanamido)-3-phenylpropanamido)-4-methylpentanamido)-6-benzyloxycarbonylaminohexanoic acid (1-7)

Compound (1-6) (9.84 g, 12.28 mmol) was dissolved in a mixed solvent of tetrahydrofuran:water=5:1 (120 mL), and lithium hydroxide monohydrate (1.14 g, 27 mmol) was added at 0° C. The resultant reaction mixture was reacted at room temperature overnight. The reactant was adjusted to pH=3 with hydrochloric acid. The title compound (8 g) was obtained after workup.

ESI-MS (m/z): 788 (M+H)$^+$.

Step 7: Synthesis of methyl 1-((R)-2-((R)-2-((R)-2-((R)-2-tert-butyloxycarbonylamino-3-phenylpropanamido)-3-phenylpropanamido)-4-methylpentanamido)-6-benzyloxycarbonylaminohexanoyl)-4-tert-butyloxycarbonylaminopiperidin-4-carboxylate (1-8)

Compound (1-7) (740 mg, 0.94 mmol) and methyl 4-tert-butoxycarbonylaminopiperidin-4-carboxylate (299 mg, 0.493 mmol) were dissolved in dichloromethane, and the resultant mixture was cooled to 0° C. Under the protection of nitrogen, N,N-diisopropylethylamine (485 mg, 3.76 mmol), copper chloride dihydrate (176 mg, 1.03 mmol) and HOBt (152 mg, 1.13 mmol) were added, HBTU (427 mg, 1.13 mmol) was added at last. The resultant reaction mixture was reacted overnight. Water (20 mL), dichloromethane (20 mL) and diatomite were added, and stirred for 5 min. The title compound (719 mg) was obtained after workup.

ESI-MS (m/z): 1029 (M+H)$^+$.

Step 8: Synthesis of methyl 1-((R)-2-((R)-2-((R)-2-((R)-2-tert-butyloxycarbonylamino-3-phenylpropanamido)-3-phenylpropanamido)-4-methylpentanamido)-6-aminohexanoyl)-4-tert-butyloxycarbonylaminopiperidin-4-carboxylate (1-9)

Compound (1-8) (1.5 g, 1.46 mmol) was dissolved in methanol (15 mL), and added with 10% Pd/C (150 mg). The reaction bottle was connected to a hydrogen balloon, the reaction was carried out at room temperature for 5 h. The title compound (1.38 g) was obtained after workup.

ESI-MS (m/z): 895 (M+H)$^+$.

Step 9: Synthesis of methyl 1-((R)-2-((R)-2-((R)-2-((R)-2-tert-butyloxycarbonylamino-3-phenylpropanamido)-3-phenylpropanamido)-4-methylpentanamido)-6-((R)-2,2-dimethyl-1,3-dioxolan-4-methylamino)hexanoyl)-4-tert-butyloxycarbonylaminopiperidin-4-carboxylate (1-10)

Compound (1-9) (250 mg, 0.28 mmol) was dissolved in dichloromethane (10 mL), and (S)-2,2-dimethyl-1,3-dioxolane-4-carboxaldehyde (47.3 mg, 0.36 mmol) was added. The resultant mixture was stirred for 5 min. Sodium triacetoxyborohydride (100 mg, 0.47 mmol) was then added. The resultant reaction mixture was reacted for 5 min, and then water was added to quench the reaction. The title compound (a crude product, 302 mg) was obtained after workup, and used directly in the next step.

ESI-MS (m/z): 1009 (M+H)$^+$.

Step 10: Synthesis of 1-((R)-2-((R)-2-((R)-2-((R)-2-tert-butyloxycarbonylamino-3-phenylpropanamido)-3-phenylpropanamido)-4-methylpentanamido)-6-((R)-2,2-dimethyl-1,3-dioxolan-4-methylamino)hexanoyl)-4-tert-butyloxycarbonylaminopiperidin-4-carboxylic acid (1-11)

Compound (1-10) (302 mg, 0.28 mmol) was dissolved in tetrahydrofuran (5 mL) and water (1 mL), and lithium hydroxide monohydrate (54 mg, 1.12 mmol) was added. The resultant mixture was kept at 14° C. and reacted for 72 h, and was adjusted to pH=3 with hydrochloric acid. The title compound (94 mg) was obtained after workup.

ESI-MS (m/z): 995 (M+H)$^+$.

Step 11: Synthesis of 4-amino-1-((R)-2-((R)-2-((R)-2-((R)-2-amino-3-phenylpropanamido)-3-phenylpropanamido)-4-methylpentanamido)-6-(((R)-2,3-dihydroxypropyl)amino)hexanoyl)piperidin-4-carboxylic acid (Compound 1)

Compound (1-11) (94 mg, 0.095 mmol) was dissolved in 1,4-dioxane (10 mL), and a solution of 4M HCl/1,4-dioxane (10 mL) was added. The resultant reaction mixture was reacted for 2 h, and the reaction temperature was kept at 20° C. The hydrochloride of the title compound (60 mg) was obtained after workup.

$^1$H NMR (400 MHz, D$_2$O) δ 7.29-7.13 (m, 10H), 4.70-4.55 (m, 1H), 4.21-4.14 (m, 2H), 3.89-3.88 (m, 2H), 3.72-3.48 (m, 10H), 3.09-2.90 (m, 6H), 2.27-2.13 (m, 2H), 1.67-1.63 (m, 2H), 1.45-1.32 (m, 7H), 1.15-1.05 (m, 2H), 0.86-0.76 (m, 6H); ESI-MS (m/z): 755.5 (M+H)$^+$.

Example 2. 4-amino-1-((R)-2-((R)-2-((R)-2-((R)-2-amino-3-phenylpropanamido)-3-phenylpropanamido)-4-methylpentanamido)-6-(((S)-2,3-dihydroxypropyl)amino)hexanoyl)piperidin-4-carboxylic acid (Compound 2)

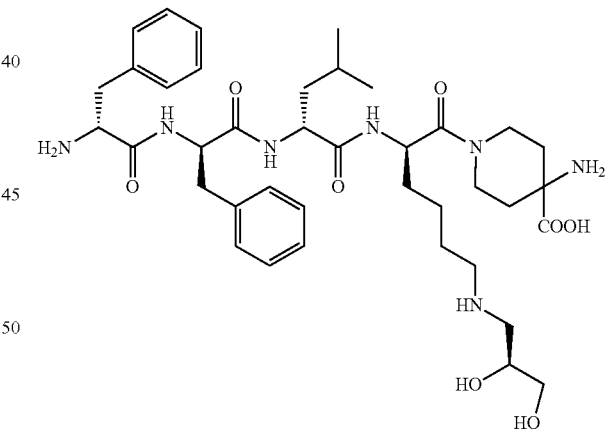

In accordance with the preparation method in Example 1, the hydrochloride of the title compound (39 mg) is synthesized, wherein, (R)-2,2-dimethyl-1,3-dioxolane-4-carboxaldehyde was used in Step 9.

$^1$H NMR (400 MHz, D$_2$O) δ 7.30-7.09 (m, 10H), 4.70-4.53 (m, 1H), 4.19-4.12 (m, 2H), 3.87-3.85 (m, 2H), 3.70-3.44 (m, 10H), 3.07-3.04 (m, 2H), 2.99-2.88 (m, 4H), 2.24-2.12 (m, 2H), 1.74-1.59 (m, 6H), 1.43-1.25 (m, 3H), 1.14-1.04 (m, 2H), 0.85-0.75 (m, 6H); ESI-MS (m/z): 755.5 (M+H)$^+$.

Example 3. 4-amino-1-((R)-2-((R)-2-((R)-2-((R)-2-amino-3-phenylpropanamido)-3-phenylpropanamido)-4-methylpentanamido)-6-((2-aminoethyl)amino)hexanoyl)piperidin-4-carboxylic acid (Compound 3)

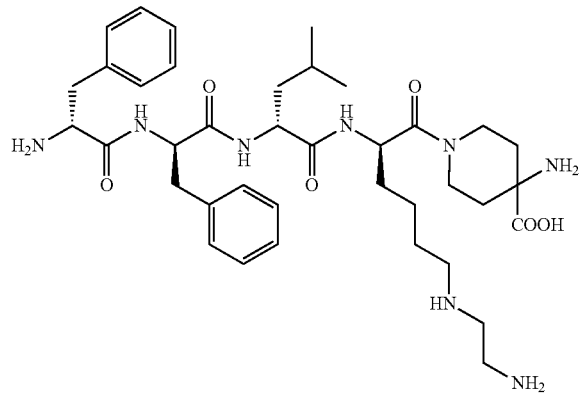 [SMILES: CC(C)C[C@@H](NC(=O)[C@@H](Cc1ccccc1)NC(=O)[C@H](N)Cc1ccccc1)C(=O)N[C@H](CCCCNCCN)C(=O)N1CCC(N)(C(=O)O)CC1]

In accordance with the preparation method in Example 1, the title compound (25 mg) is synthesized, wherein, tert-butyl (2-oxoethyl)aminocarboxylate was used in Step 9.

$^1$H NMR (400 MHz, D$_2$O) δ 7.45-7.12 (m, 10H), 4.74-4.57 (m, 2H), 4.35-4.14 (m, 2H), 3.96-3.30 (m, 10H), 3.25-2.90 (m, 6H), 2.25-2.22 (m, 2H), 2.04-1.62 (m, 6H), 1.64-1.31 (m, 5H), 1.01-0.76 (m, 6H); ESI-MS (m/z): 724.3 (M+H)$^+$.

Example 4. 4-amino-1-((R)-2-((R)-2-((R)-2-((R)-2-amino-3-phenylpropanamido)-3-phenylpropanamido)-4-methylpentanamido)-6-((3-aminopropyl)amino)hexanoyl)piperidin-4-carboxylic acid (Compound 4)

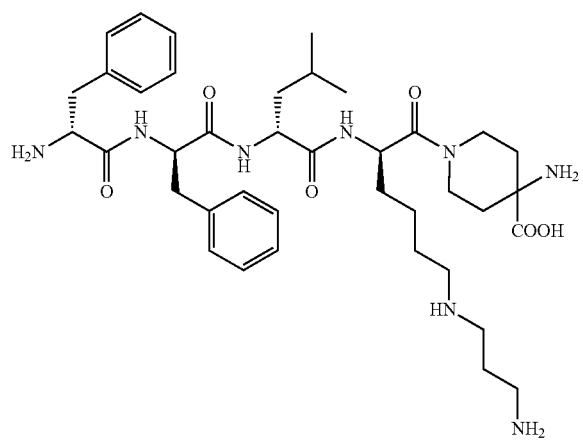 [SMILES: CC(C)C[C@@H](NC(=O)[C@@H](Cc1ccccc1)NC(=O)[C@H](N)Cc1ccccc1)C(=O)N[C@H](CCCCNCCCN)C(=O)N1CCC(N)(C(=O)O)CC1]

In accordance with the preparation method in Example 1, the hydrochloride of the title compound (60 mg) is synthesized, wherein, tert-butyl (3-oxopropyl)aminocarboxylate was used in Step 9.

$^1$H NMR (400 MHz, D$_2$O) δ 7.38-7.02 (m, 10H), 4.56-4.53 (m, 2H), 4.28-4.07 (m, 2H), 3.84-3.44 (m, 5H), 3.17-2.85 (m, 10H), 2.15-2.13 (m, 2H), 2.05-1.54 (m, 8H), 1.37-1.35 (m, 5H), 0.82-0.75 (m, 6H);

ESI-MS (m/z): 738.4 (M+H)$^+$.

Example 5. 4-amino-1-((R)-2-((R)-2-((R)-2-((R)-2-amino-3-phenylpropanamido)-3-phenylpropanamido)-4-methylpentanamido)-6-((2-(2-methoxyethoxy)ethyl)amino)hexanoyl)piperidin-4-carboxylic acid (Compound 5)

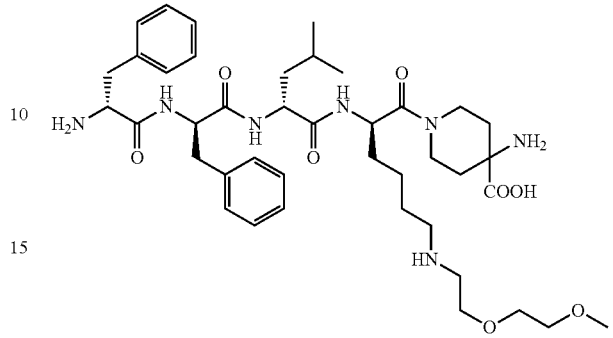

In accordance with the preparation method in Example 1, the hydrochloride of the title compound (45 mg) is synthesized, wherein, 1,1-dimethoxy-2-(2-methoxyethoxy)ethane was used in Step 9.

$^1$H NMR (400 MHz, D$_2$O) δ 7.38-7.05 (m, 10H), 4.63-4.51 (m, 2H), 4.27-4.06 (m, 2H), 3.88-3.42 (m, 10H), 3.19-3.02 (m, 4H), 2.93-2.91 (m, 4H), 1.94-1.53 (m, 6H), 1.37-1.35 (m, 5H), 0.92-0.69 (m, 6H)

ESI-MS (m/z): 783.1 (M+H)$^+$

Example 6. 4-amino-1-((R)-28-((R)-2-((R)-2-((R)-2-amino-3-phenylpropanamido)-3-phenylpropanamido)-4-methylpentanamido)-2,5,8,11,14,17,20-heptaoxa-23-azanonacosan-29-oyl)piperidin-4-carboxylic acid (Compound 6)

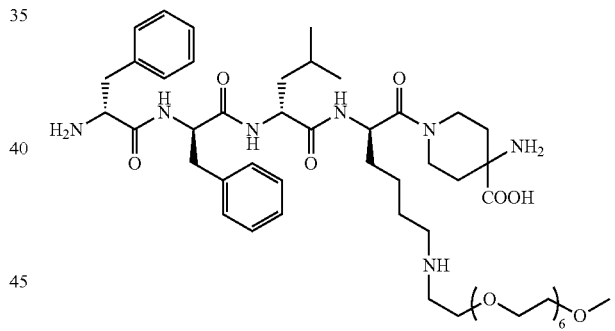

In accordance with the preparation method in Example 1, the hydrochloride of the title compound (23 mg) is synthesized, wherein, CHO—CH$_2$(OC$_2$H$_4$)$_6$OCH$_3$ (which was a corresponding aldehyde to heptaethylene glycol monomethyl ether, with a structure of

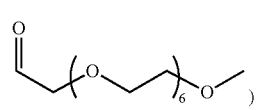

)

was used in Step 9.

$^1$H NMR (400 MHz, D$_2$O) δ 7.31-7.15 (m, 10H), 4.59-4.57 (m, 2H), 4.23-4.15 (m, 2H), 3.83-3.51 (m, 30H), 3.28 (s, 3H), 3.16-3.13 (m, 4H), 3.08-2.89 (m, 4H), 2.21-2.14 (m, 2H), 1.76-1.66 (m, 6H), 1.47-1.32 (m, 5H), 0.88-0.81 (m, 6H);

ESI-MS (m/z): 501.9 (M/2+H)$^+$.

Example 7. 4-amino-1-((R)-43-((R)-2-((R)-2-((R)-2-amino-3-phenylpropanamido)-3-phenylpropanamido)-4-methylpentanamido)-2,5,8,11,14,17,20,23,26,29,32,35-dodecaoxa-38-azatetratetracontan-44-oyl)piperidin-4-carboxylic acid (Compound 7)

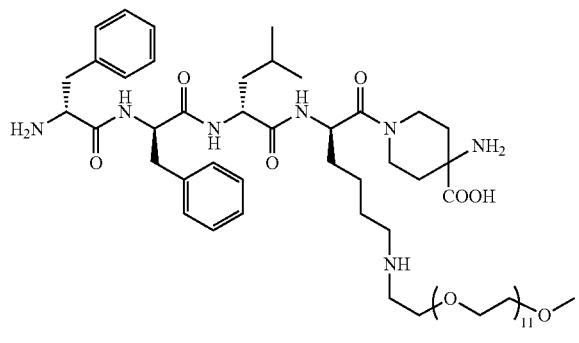

In accordance with the preparation method in Example 1, the hydrochloride of the title compound (19.4 mg) is synthesized, wherein, CHO—CH$_2$(OC$_2$H$_4$)$_{11}$OCH$_3$ (which was the corresponding aldehyde to dodecaethylene glycol monomethyl ether, with a structure of

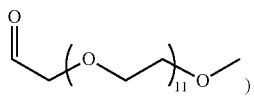

was used in Step 9.

$^1$H NMR (400 MHz, D$_2$O) δ 7.24-7.14 (m, 10H), 4.59-4.54 (m, 2H), 4.22-4.14 (m, 2H), 3.63-3.48 (m, 50H), 3.28 (s, 3H), 3.15-2.79 (m, 8H), 2.20-2.12 (m, 2H), 1.90-1.65 (m, 6H), 1.34-1.16 (m, 5H), 0.88-0.77 (m, 6H);

ESI-MS (m/z): 612.0 (M/2+H)$^+$.

Example 8. 4-amino-1-((R)-2-((R)-2-((R)-2-((R)-2-amino-3-phenylpropanamido)-3-phenylpropanamido)-4-methylpentanamido)-6-((1,3-dihydroxypropan-2-yl)amino)hexanoyl)piperidin-4-carboxylic acid (Compound 8)

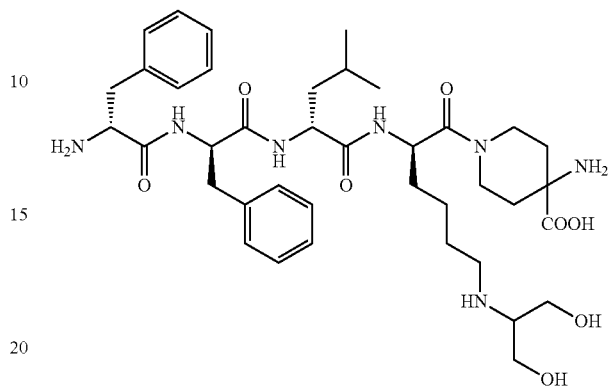

In accordance with the preparation method in Example 1, the hydrochloride of the title compound (85 mg) is synthesized, wherein, 2,2-dimethyl-1,3-dioxan-5-one was used in Step 9.

$^1$H NMR (400 MHz, D$_2$O) δ 7.37-7.03 (m, 10H), 4.54-4.51 (m, 2H), 4.27-4.07 (m, 2H), 3.87-3.43 (m, 8H), 3.15-2.81 (m, 6H), 2.27-2.03 (m, 2H), 1.90-1.53 (m, 6H), 1.37-1.35 (m, 5H), 0.92-0.70 (m, 6H);

ESI-MS (m/z): 755.1 (M+H)$^+$.

Example 9. 1-((R)-6-amino-2-((R)-2-((R)-2-((R)-2-amino-3-phenylpropanamido)-3-phenylpropanamido)-4-methylpentanamido)hexanoyl)-4-((3-aminopropyl)amino)piperidin-4-carboxylic acid (Compound 9)

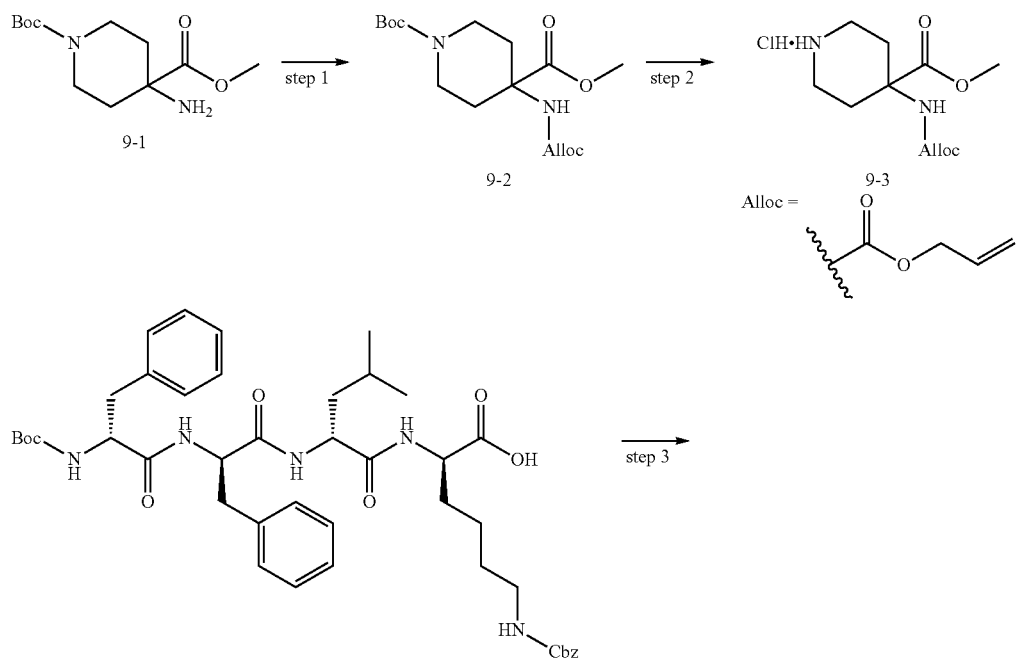

-continued
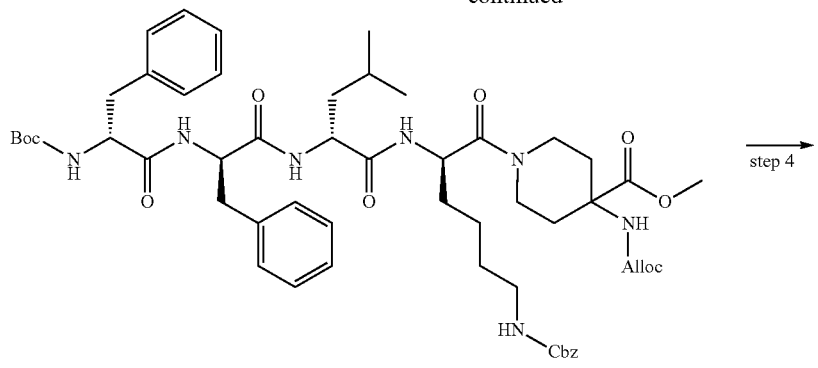
9-4
step 4
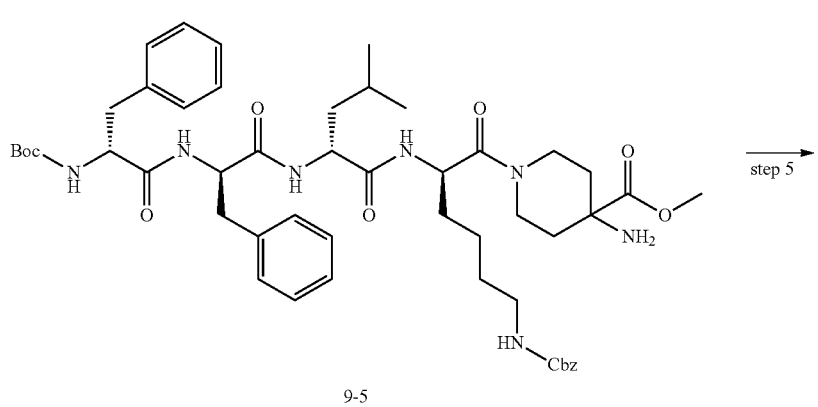
9-5
step 5
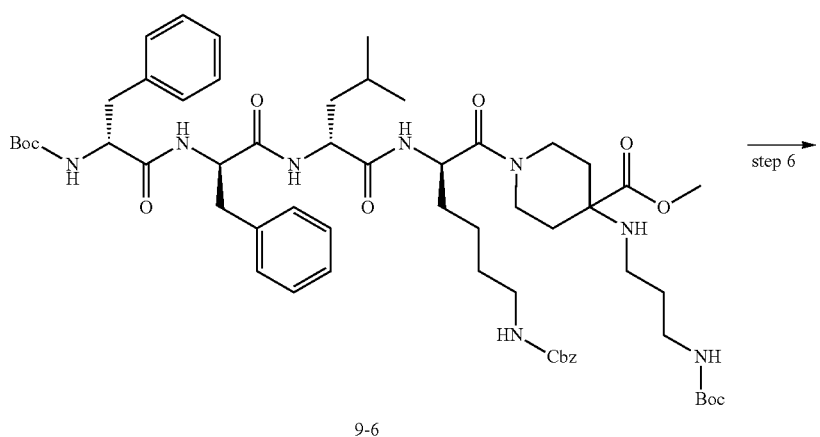
9-6
step 6
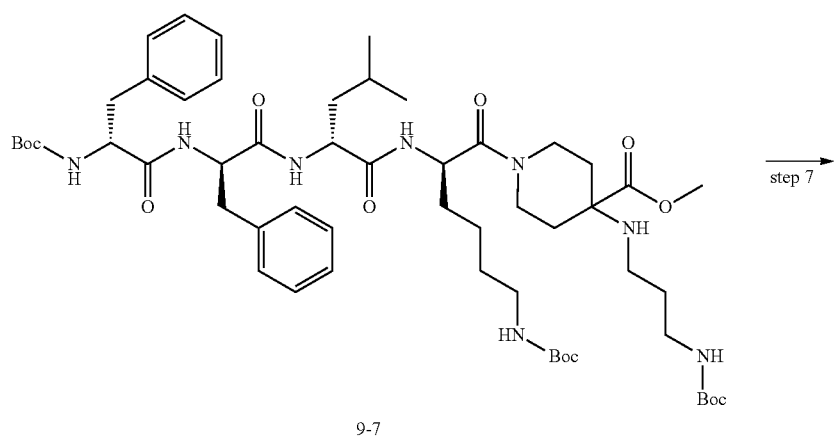
9-7
step 7

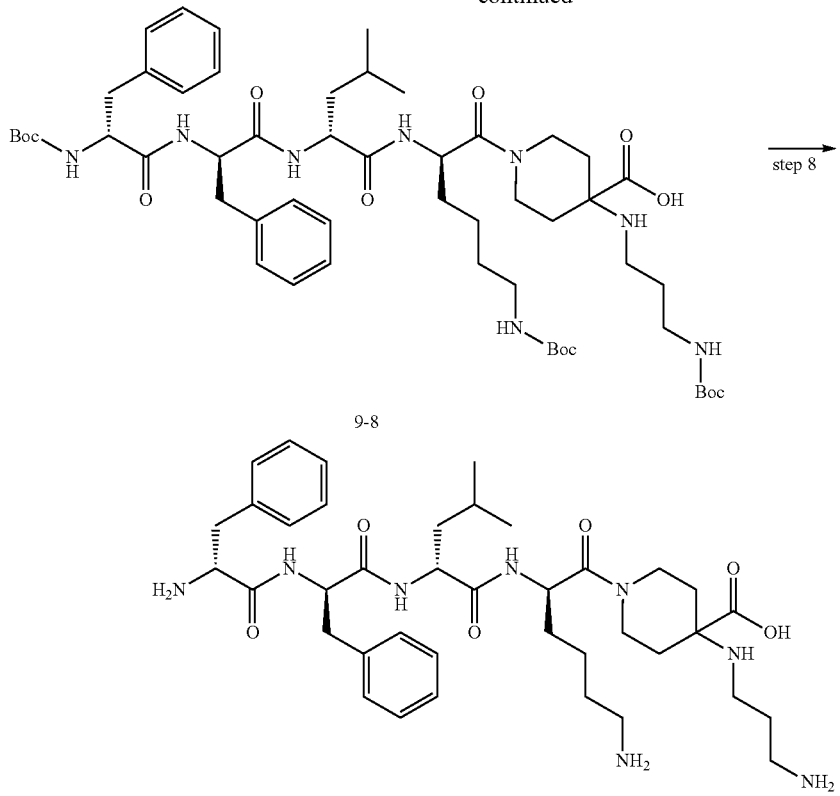

9

Step 1: Synthesis of methyl 1-tert-butyloxycarbonyl-4-(allyloxycarbonylamino)piperidin-4-carboxylate (9-2)

Methyl 1-tert-butyloxycarbonyl-4-aminopiperidin-4-carboxylate (9-1) (0.5 g, 1.94 mmol) and potassium carbonate (0.402 g, 2.91 mmol) were dissolved in a mixed solvent of tetrahydrofuran/water (4:1) (40 mL), AllocCl (0.28 g, 2.32 mol) was added in an ice-bath. Under the protection of nitrogen, the resultant reaction mixture was reacted at room temperature overnight. The title compound (0.8 g) was obtained after workup.
ESI-MS (m/z): 343.2 (M+H)$^+$.

Step 2: Synthesis of methyl 4-(Alloc-amino)piperidin-4-carboxylate (9-3)

Compound (9-2) (0.8 g, 2.27 mmol) was dissolved in dioxane (6 mL), and a solution of HCl/dioxane was added dropwise (3 mL, 12 mmol). The reaction was carried out at room temperature overnight. After the reaction solution was concentrated under reduced pressure, the hydrochloride of the title compound (0.56 g) was obtained.
ESI-MS (m/z): 243.1 (M+H)$^+$.

Step 3: Synthesis of methyl 4-(allyloxycarbonylamino)-1-((R)-2-((R)-2-((R)-2-((R)-2-tert-butyloxycarbonylamino-3-phenylpropanamido)-3-phenylpropanamido)-4-methylpentanamido)-6-benzyloxycarbonylaminohexanoyl)piperidin-4-carboxylate (9-4)

The hydrochloride of Compound (9-3) (0.56 g, 1.94 mmol) was dissolved in tetrahydrofuran (30 mL), and added with DIEA (1.05 g, 8.15 mmol). The resultant mixture was stirred at room temperature for 30 min. Compound 1-7 (1.61 g, 2.04 mmol), HOBt (0.315 g, 2.33 mmol), CuCl$_2$·2H$_2$O (0.363 g, 2.13 mmol), and HBTU (0.882 g, 2.33 mmol) were added. Under the protection of nitrogen, the resultant reaction mixture was reacted at 0° C. overnight. The title compound (1 g) was obtained after workup.
ESI-MS (m/z): 1012.5 (M+H)$^+$.

Step 4: Synthesis of methyl 4-amino-1-((R)-2-((R)-2-((R)-2-((R)-2-tert-butyloxycarbonylamino-3-phenylpropanamido)-3-phenylpropanamido)-4-methylpentanamido)-6-benzyloxycarbonylaminohexanoyl)piperidin-4-carboxylate (9-5)

Compound (9-4) (2.66 g, 2.6 mmol) was dissolved in dichloromethane (30 mL), and added with 1,3-dimethylbarbituric acid (0.406 g, 2.6 mmol) and Pd (PPh$_3$)$_4$ (0.065 g, 0.05 mmol). Under the protection of nitrogen, the resultant reaction mixture was reacted at room temperature for 3 h, and concentrated under reduced pressure. The resultant crude product was prepared by preparative HPLC to obtain the title compound (0.8 g).
ESI-MS (m/z): 928.5 (M+H)$^+$.

Step 5: Synthesis of methyl 4-(3-(tert-butyloxycarbonylamino)propylamino)-1-((R)-2-((R)-2-((R)-2-((R)-2-tert-butyloxycarbonylamino-3-phenylpropanamido)-3-phenylpropanamido)-4-methylpentanamido)-6-benzyloxycarbonylaminohexanoyl)piperidin-4-carboxylate (9-6)

Compound (9-5) (0.2 g, 0.22 mmol) was dissolved in methanol (4 mL), and added with tert-butyl (3-oxopropyl)

aminocarboxylate (0.038 g, 0.22 mmol), sodium cyanoborohydride (0.056 g, 0.88 mmol) and a little amount of glacial acetic acid. The resultant reaction mixture was reacted at room temperature overnight. The title compound (215 mg) was obtained after workup.

ESI-MS (m/z): 1085.6 (M+H)$^+$.

Step 6: Synthesis of methyl 4-(3-(tert-butyloxycarbonylamino)propylamino)-1-((R)-2-((R)-2-((R)-2-((R)-2-tert-butyloxycarbonylamino-3-phenylpropanamido)-3-phenylpropanamido)-4-methylpentanamido)-6-tert-butyloxycarbonylaminohexanoyl)piperidin-4-carboxylate (9-7)

Compound (9-6) (0.215 g, 0.2 mmol) was dissolved in methanol (5 mL), and added with Pd/C (0.02 g) and di-tert butyl dicarbonate (0.15 g, 0.7 mmol). The reaction bottle was connected to a hydrogen balloon, and the reaction was carried out at room temperature overnight. The title compound (118 mg) was obtained after workup.

ESI-MS (m/z): 1051.6 (M+H)$^+$.

Step 7: Synthesis of 4-(3-(tert-butyloxycarbonylamino)propylamino)-1-((R)-2-((R)-2-((R)-2-((R)-2-tert-butyloxycarbonylamino-3-phenylpropanamido)-3-phenylpropanamido)-4-methylpentanamido)-6-benzyloxycarbonylaminohexanoyl)piperidin-4-carboxylic acid (9-8)

Compound (9-7) (118 mg, 0.11 mmol) was dissolved in a mixed solvent of tetrahydrofuran/water (4:1) (3 mL), and LiOH (11 mg) was added. The reaction was carried out at room temperature for 48 h. The reaction mixture was diluted with water, and was adjusted to pH=3 with hydrochloric acid. The title compound (28 mg) was obtained after workup.

ESI-MS (m/z): 1037.6 (M+H)$^+$.

Step 8: Synthesis of 1-((R)-6-amino-2-((R)-2-((R)-2-((R)-2-amino-3-phenylpropanamido)-3-phenylpropanamido)-4-methylpentanamido)hexanoyl)-4-((3-aminopropyl)amino)piperidin-4-carboxylic acid (Compound 9)

Compound (9-8) (28 mg) was dissolved in 1,4-dioxane (4 mL), and HCl/1,4-dioxane (1 mL, 4 mmol) was added dropwise. The reaction was carried out at room temperature overnight. The hydrochloride of the title compound (8 mg) was obtained after workup.

$^1$H NMR (DMSO-d$_6$, 400 MHz) δ 7.29-7.12 (m, 10H), 4.56-4.52 (m, 1H), 4.22-4.12 (m, 3H), 3.58-3.47 (m, 21H), 3.19-2.86 (m, 12H), 2.30-2.20 (m, 2H), 2.02-1.06 (m, 14H), 0.86-0.78 (m, 6H);

ESI-MS (m/z): 369.2 (M/2+H)$^+$.

Example 10. 1-((R)-6-amino-2-((R)-2-((R)-2-((R)-2-amino-3-phenylpropanamido)-3-phenylpropanamido)-4-methylpentanamido)hexanoyl)-4-(((R)-2,3-dihydroxypropyl)amino)piperidin-4-carboxylic acid (Compound 10)

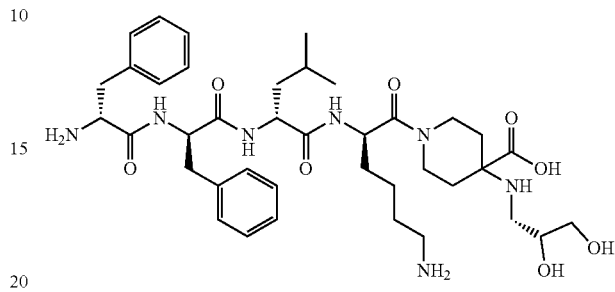

In accordance with the preparation method in Example 9, the hydrochloride of the title compound (29 mg) is synthesized, wherein, (S)-2,2-dimethyl-1,3-dioxolane-4-carboxaldehyde was used in Step 5.

$^1$H NMR (DMSO-d$_6$, 400 MHz) δ 7.30-7.12 (m, 10H), 4.60-4.52 (m, 2H), 4.24-3.83 (m, 6H), 3.67-3.45 (m, 5H), 3.10-2.86 (m, 9H), 2.28-2.20 (m, 2H), 1.88-1.28 (m, 12H), 0.86-0.79 (m, 6H);

ESI-MS (m/z): 754.4 (M+H)$^+$.

Example 11. 1-((R)-6-amino-2-((R)-2-((R)-2-amino-3-phenylpropanamido)-3-phenylpropanamido)-4-methylpentanamido)hexanoyl)-4-((2-aminoethyl)amino)piperidin-4-carboxylic acid (Compound 11)

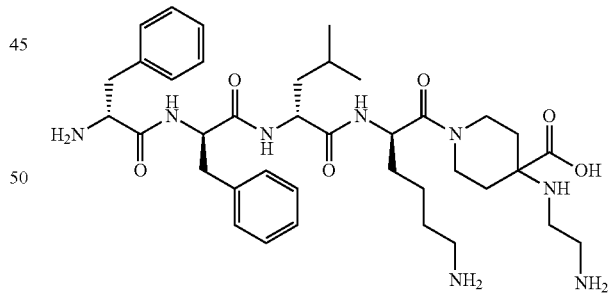

In accordance with the preparation method in Example 9, the hydrochloride of the title compound (31 mg) is synthesized, wherein, tert-butyl (2-oxoethyl)aminocarboxylate was used in Step 5.

$^1$H NMR (DMSO-d$_6$, 400 MHz) δ 7.38-7.14 (m, 10H), 4.59-4.54 (m, 2H), 4.22-4.12 (m, 3H), 3.99-3.55 (m, 4H), 3.30-2.88 (m, 12H), 2.29-2.19 (m, 2H), 1.69-1.59 (m, 6H), 1.46-1.32 (m, 5H), 0.88-0.81 (m, 6H);

ESI-MS (m/z): 723.4 (M+H)$^+$.

Example 12. 1-((R)-6-amino-2-((R)-2-((R)-2-((R)-2-amino-3-phenylpropanamido)-3-phenylpropanamido)-4-methylpentanamido)hexanoyl)-4-((2-(2-methoxyethoxy)ethyl)amino)piperidin-4-carboxylic acid (Compound 12)

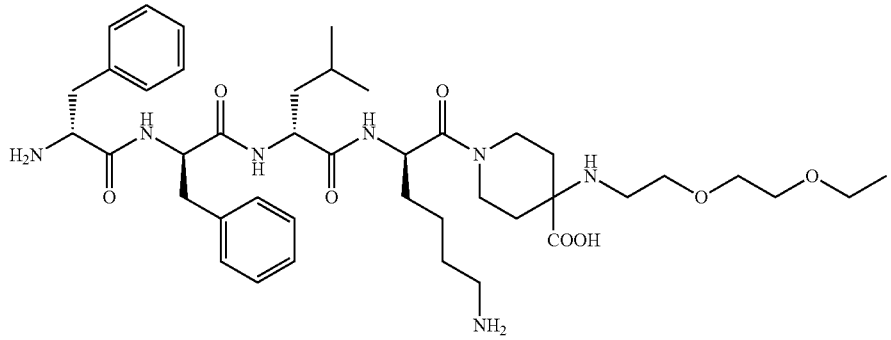 [SMILES: CCOCCOCCNC1(C(=O)O)CCN(C(=O)[C@@H](CCCCN)NC(=O)[C@@H](CC(C)C)NC(=O)[C@@H](Cc2ccccc2)NC(=O)[C@H](N)Cc2ccccc2)CC1]

In accordance with the preparation method in Example 9, the hydrochloride of the title compound (40 mg) is synthesized, wherein, 1,1-dimethoxy-2-(2-methoxyethoxy)ethane was used in Step 5.

$^1$H NMR (400 MHz, D$_2$O) δ 7.40-7.09 (m, 10H), 4.59-4.55 (m, 2H), 4.34-4.10 (m, 3H), 3.96-3.94 (m, 1H), 3.81-3.45 (m, 7H), 3.32 (s, 1H), 3.21-2.86 (m, 9H), 2.27-2.25 (m, 2H), 1.91-1.57 (m, 6H), 1.58-1.25 (m, 5H), 0.85-0.82 (m, 6H);

ESI-MS (m/z): 782.5 (M+H)$^+$.

Example 13. 4-(2,5,8,11,14,17,20-heptaoxadocosan-22-ylamino)-1-((R)-6-amino-2-((R)-2-((R)-2-((R)-2-amino-3-phenylpropanamido)-3-phenylpropanamido)-4-methylpentanamido)hexanoyl)piperidin-4-carboxylic acid (Compound 13)

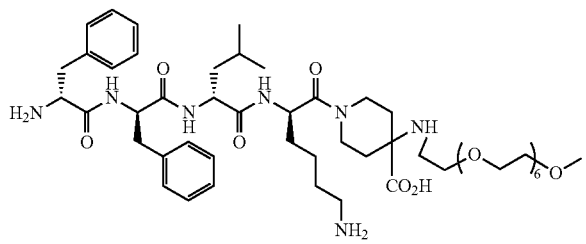

In accordance with the preparation method in Example 9, the hydrochloride of the title compound (2 mg) is synthesized, wherein, CHO—CH$_2$(OC$_2$H$_4$)$_6$OCH$_3$ (which was the corresponding aldehyde to heptaethylene glycol monomethyl ether, with a structure of

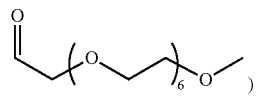

was used in Step 5.

$^1$H NMR (400 MHz, D$_2$O) δ 7.24-7.14 (m, 10H), 4.60-4.54 (m, 2H), 4.25-4.14 (m, 2H), 3.63-3.48 (m, 50H), 3.28 (s, 3H), 3.15-2.79 (m, 8H), 2.20-2.12 (m, 2H), 1.90-1.65 (m, 6H), 1.34-1.16 (m, 5H), 0.88-0.77 (m, 6H);

ESI-MS (m/z): 501.9 (M/2+H)$^+$.

Example 14. 4-(2,5,8,11,14,17,20,23,26,29,32,35-dodecaoxaheptatriacontan-37-ylamino)-1-((R)-6-amino-2-((R)-2-((R)-2-((R)-2-amino-3-phenylpropanamido)-3-phenylpropanamido)-4-methylpentanamido)hexanoyl)piperidin-4-carboxylic acid (Compound 14)

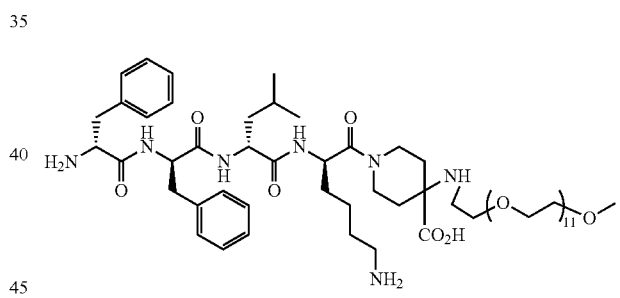

In accordance with the preparation method in Example 9, the hydrochloride of the title compound (4 mg) is synthesized, wherein, CHO—CH$_2$(OC$_2$H$_4$)$_{11}$OCH$_3$ (which was the corresponding aldehyde to dodecaethylene glycol monomethyl ether, with a structure of

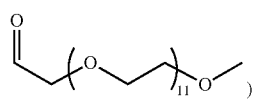

was used in Step 5.

$^1$H NMR (400 MHz, D$_2$O) δ 7.27-7.06 (m, 10H), 4.52-4.47 (m, 1H), 4.22-4.16 (m, 1H), 4.06-3.26 (m, 55H), 3.06-2.76 (m, 7H), 2.66-2.61 (m, 2H), 2.10-1.96 (m, 2H), 1.66-1.27 (m, 11H), 0.86-0.78 (m, 6H);

ESI-MS (m/z): 612.0 (M/2+H)$^+$.

Example 15: 4-amino-1-((R)-2-((R)-2-((R)-2-amino-3-phenylpropanamido)-3-phenylpropanamido)-4-methylpentanamido)-6-(di(2-(2-methoxyethoxy)ethyl)amino)hexanoyl)piperidin-4-carboxylic acid (Compound 15)

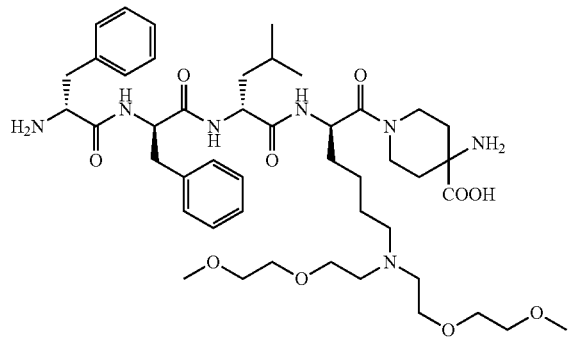 [SMILES: COCCOCCN(CCCC[C@@H](NC(=O)[C@@H](CC(C)C)NC(=O)[C@@H](Cc1ccccc1)NC(=O)[C@H](N)Cc1ccccc1)C(=O)N1CCC(N)(C(=O)O)CC1)CCOCCOC]

In accordance with the preparation method in Example 1, the trifluoroacetate of the title compound (45 mg) is synthesized, wherein, (2-methoxyethoxy) acetaldehyde dimethyl acetal was used in Step 9.

$^1$H NMR (400 MHz, DMSO-$d_6$) δ 8.84-8.09 (m, 8H), 7.33-7.20 (m, 10H), 4.75-4.63 (m, 2H), 4.40-4.32 (m, 1H), 4.02-3.97 (m, 1H), 3.83-3.62 (m, 7H), 3.56-3.54 (m, 5H), 3.45-3.35 (m, 7H), 3.24 (s, 6H), 3.14-3.06 (m, 5H), 2.94-2.89 (m, 1H), 2.82-2.77 (m, 1H), 2.09-1.95 (m, 2H), 1.74-1.44 (m, 9H), 1.30-1.26 (m, 2H), 0.92-0.86 (m, 6H);
ESI-MS (m/z): 884.5 (M+H)$^+$.

Example 16: 4-amino-1-((R)-2-((R)-2-((R)-2-amino-3-phenylpropanamido)-3-phenylpropanamido)-4-methylpentanamido)-6-(di(carboxymethyl)amino)hexanoyl)piperidin-4-carboxylic acid (Compound 16)

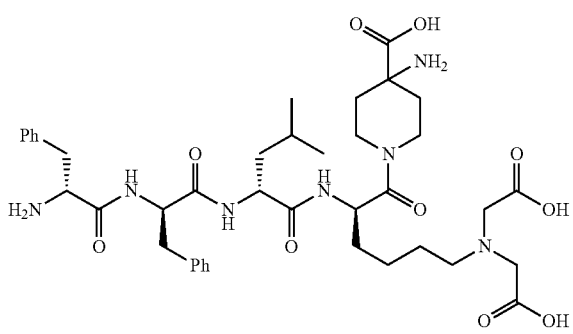 [SMILES: CC(C)C[C@@H](NC(=O)[C@@H](Cc1ccccc1)NC(=O)[C@H](N)Cc1ccccc1)C(=O)N[C@H](CCCCN(CC(=O)O)CC(=O)O)C(=O)N1CCC(N)(C(=O)O)CC1]

In accordance with the preparation method in Example 1, the trifluoroacetate of the title compound (5.0 mg) is synthesized, wherein, ethyl glyoxylate was used in Step 9.

$^1$H NMR (400 MHz, DMSO-$d_6$) δ 8.85-8.03 (m, 10H), 7.29-7.22 (m, 10H), 4.70-4.63 (m, 2H), 4.34-4.33 (m, 1H), 4.02-3.99 (m, 1H), 3.90-3.34 (m, 8H), 3.13-3.05 (m, 2H), 2.96-2.91 (m, 1H), 2.84-2.72 (m, 2H), 2.09-2.20 (m, 2H), 1.81-1.71 (m, 2H), 1.68-1.55 (m, 2H), 1.53-1.40 (m, 5H), 1.26-1.22 (m, 3H), 0.92-0.85 (m, 6H);
ESI-MS (m/z): 796.4 (M+H).

Example 17: 4-amino-1-((R)-2-((R)-2-((R)-2-amino-3-phenylpropanamido)-3-phenylpropanamido)-4-methylpentanamido)-6-((carboxymethyl)amino)hexanoyl)piperidin-4-carboxylic acid (Compound 17)

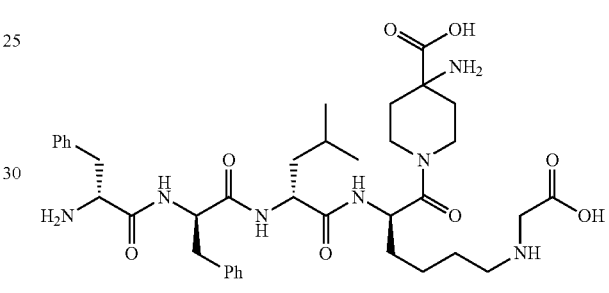

In accordance with the preparation method in Example 1, the trifluoroacetate of the title compound (5 mg) is synthesized, wherein, ethyl glyoxylate was used in Step 9.

$^1$H NMR (400 MHz, D$_2$O) δ 7.40-7.23 (m, 10H), 4.69-4.62 (m, 2H), 4.35-4.25 (m, 1H), 3.95-3.56 (m, 6H), 3.18 (d, J=8.0 Hz, 2H), 3.08-2.97 (m, 4H), 2.35-2.23 (m, 2H), 2.02-1.17 (m, 6H), 1.56-1.40 (m, 6H), 0.98-0.91 (m, 6H);
ESI-MS (m/z): 738.4 (M+H).

Example 18: 4-amino-1-((R)-2-((R)-2-((R)-2-(2-aminoethylamino)-3-phenylpropionyl)-3-phenylpropionyl)-4-methylpentanamido)-6-aminohexanoyl)piperidin-4-carboxylic acid (Compound 18)

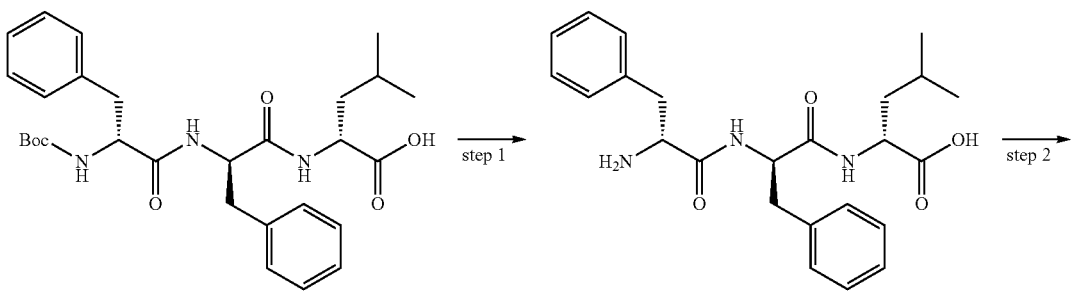

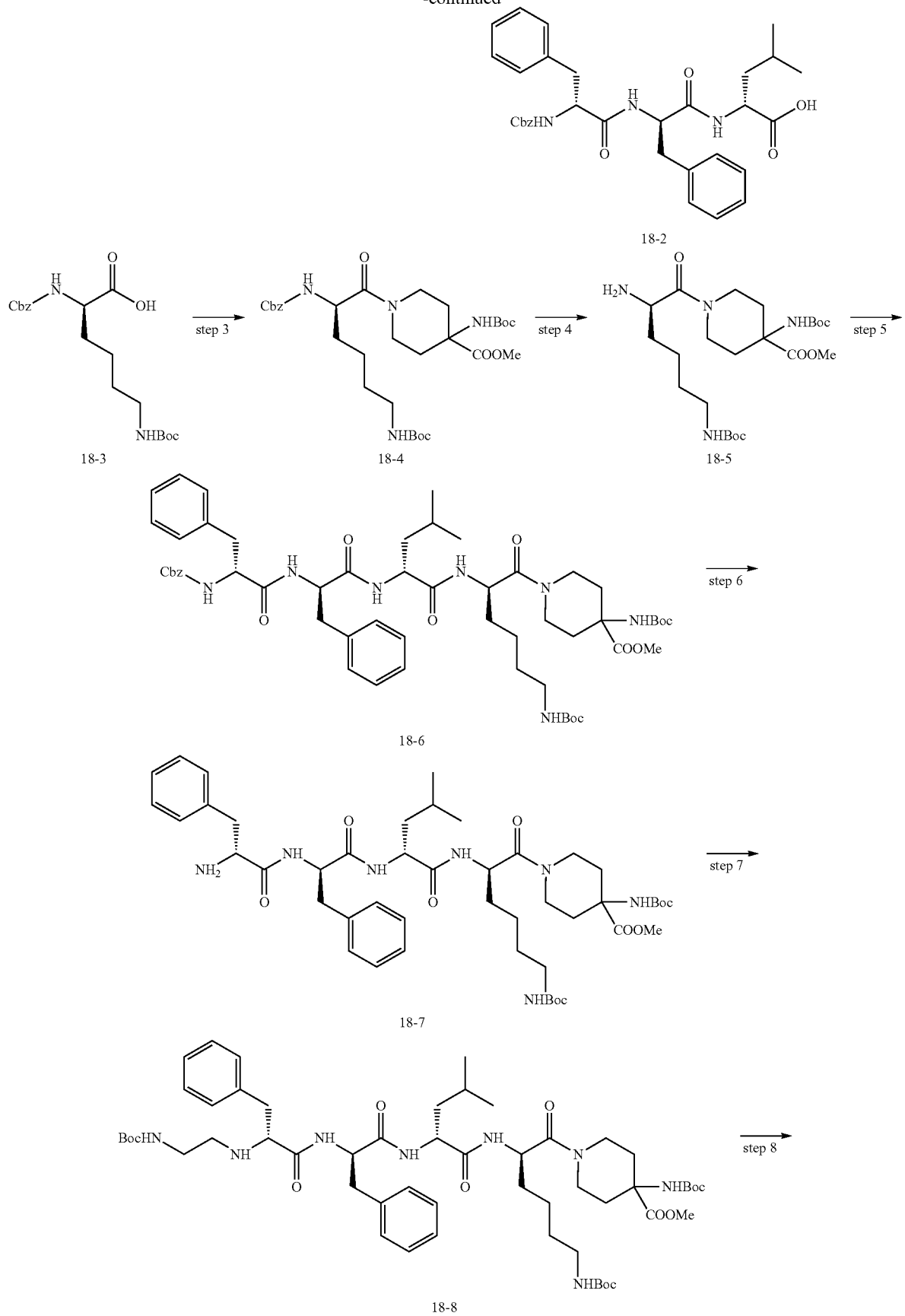

-continued

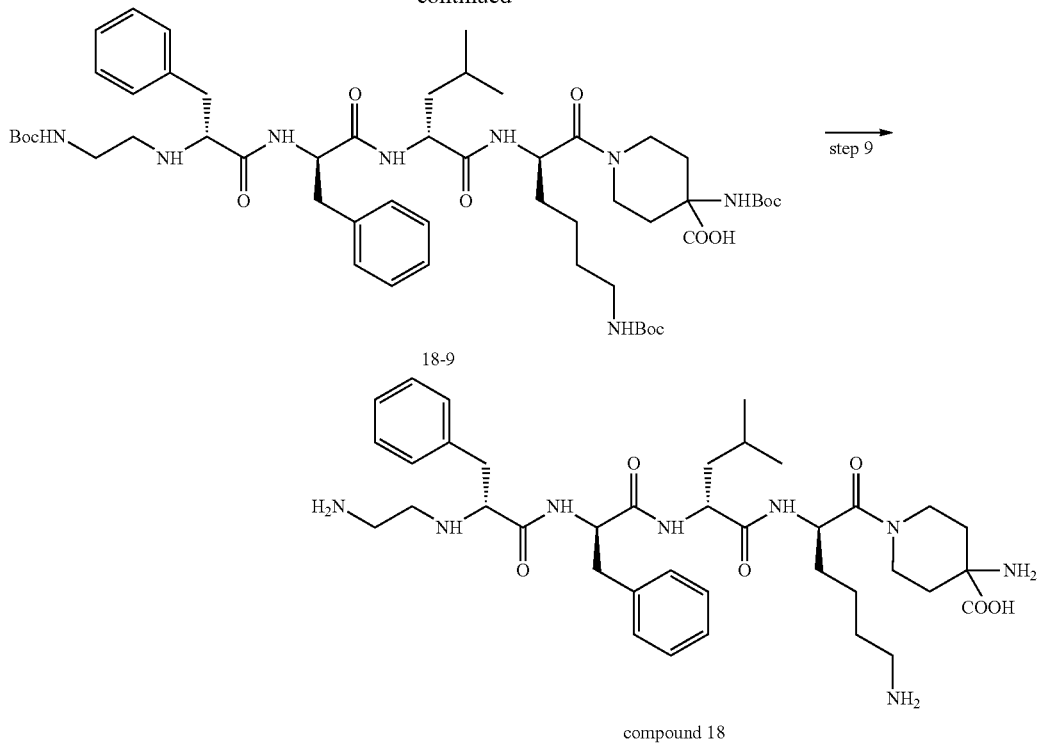

compound 18

Step 1: Synthesis of (R)-2-((R)-2-((R)-2-amino-3-phenylpropanamido)-3-phenylpropanamido)-4-methylvaleric acid (18-1)

Compound (1-5) (3 g, 5.7 mmol) was dissolved in 2M HCl/EA (30 mL), and reacted at room temperature for 4 h. The title compound (a crude product, 2.2 g) was obtained after workup, and was used directly in the next step.
ESI-MS (m/z): 427 (M+H)$^+$.

Step 2: Synthesis of (R)-2-((R)-2-((R)-2-(benzyloxycarbonylamino)-3-phenylpropanamido)-3-phenylpropanamido)-4-methylvaleric acid (18-2)

Compound (18-1) (2.755 g, 5.964 mmol) was dissolved in 1,4-dioxane (60 mL) and water (30 mL); and added sequentially with NaHCO$_3$ (1.0 g, 11.93 mmol) and N-(Benzyloxycarbonyloxy)succinimide (1.56 g, 6.26 mmol). The reaction was carried out at room temperature for 0.5 h. The resultant mixture was then cooled to 0° C., and adjusted to pH=3 with 1N HCl aqueous solution. The title compound (a crude product, 3.38 g) was obtained after workup, and was used directly in the next step.
ESI-MS (m/z): 560 (M+H)$^+$.

Step 3: Synthesis of methyl (R)-1-(2-(benzyloxycarbonylamino)-6-(tert-butyloxycarbonylamino)hexanoyl)-4-(tert-butyloxycarbonylamino)piperidin-4-carboxylate (18-4)

N-benzyloxycarbonyl-N'-tert-butyloxycarbonyl-D-lysine (4 g, 10.5 mmol) and methyl4-N—BOC-piperidin-4-carboxylate (3 g, 5.0 mmol) were dissolved in dichloromethane (10 mL), and the resultant mixture was cooled to 0° C. Under the protection of nitrogen, DIEA (5.43 g, 42 mmol), copper dichloride dehydrate (1.88 g, 11 mmol), HOBt (1.62 g, 12 mmol), and HBTU (4.55 g, 12 mmol) were separately added. The reaction was carried out for 16 h. The title compound (a crude product, 6.69 g) was obtained after workup, and was used directly in the next step.
ESI-MS (m/z): 621 (M+H)$^+$;

Step 4: Synthesis of methyl (R)-1-(2-amino-6-(tert-butyloxycarbonylamino)hexanoyl)-4-(tert-butyloxycarbonylamino)piperidin-4-carboxylate (18-5)

Compound 18-4 (1.30 g, 2.09 mmol) was dissolved in methanol (25 mL), and added with 10% Pd/C (130 mg), and the replacement with H$_2$ was performed. The reaction was carried out at room temperature for 4 h. Posttreatment was performed to obtain the title compound (1.38 g), which was used directly in the reaction in the next step.
ESI-MS (m/z): 487 (M+H)$^+$.

Step 5: Synthesis of methyl 1-((R)-2-((R)-2-((R)-2-((R)-2-benzyloxycarbonylamino-3-phenylpropionyl)-3-phenylpropionyl)-4-methylpentanamido)-6-tert-butyloxycarbonylaminohexanoyl)-4-tert-butyloxycarbonylaminopiperidin-4-carboxylate (18-6)

Compound 18-5 (700 mg, 1.25 mmol), and Compound 18-2 (609 mg, 1.25 mmol), were dissolved in dichloromethane (20 mL). The resultant mixture was cooled to −5° C., to which N-methylmorpholine (380 mg, 3.75 mmol), HOBt (253 mg, 1.88 mmol), and 1-(3-dimethylaminopropyl)-3-ethylcarbodiimide hydrochloride (360 mg, 1.88 mmol) were added. The resultant reaction mixture was reacted at 0° C. overnight. The title compound (a crude product, 1.20 g) was obtained after workup, and was used directly in the next step.
ESI-MS (m/z): 1028.5 (M+H)$^+$.

Step 6: Synthesis of methyl 1-((R)-2-((R)-2-((R)-2-((R)-2-amino-3-phenylpropionyl)-3-phenylpropionyl)-4-methylpentanamido)-6-tert-butyloxycarbonylaminohexanoyl)-4-tert-butyloxycarbonylaminopiperidin-4-carboxylate (18-7)

Compound 18-6 (1.42 g, 1.38 mmol) was dissolved in methanol (25 mL), 10% Pd/C (140 mg) was added, and the replacement with H$_2$ was performed. The reaction was carried out at room temperature for 4 h. After filtration through diatomite, washing with methanol, and drying by rotary evaporation, the title compound (1.13 g) was obtained.
ESI-MS (m/z): 894.5 (M+H)$^+$.

Step 7: Synthesis of methyl 1-((R)-2-((R)-2-((R)-2-((R)-2-((2-tert-butyloxycarbonylaminoethyl)amino)-3-phenylpropionyl)-3-phenylpropionyl)-4-methylpentanamido)-6-tert-butyloxycarbonylaminohexanoyl)-4-tert-butyl oxycarbonylaminopiperidin-4-carboxylate (18-8)

Compound 18-7 (200 mg, 0.22 mmol) was dissolved in dichloromethane (15 mL). Under the protection of nitrogen, the resultant solution was cooled to −5° C., to which N-tert-butyloxycarbonyl-2-aminoacetaldehyde (32 mg, 0.20 mmol) was added and stirred for 10 min, followed by an addition of sodium triacetoxyborohydride (94 mg, 0.44 mmol). The resultant reaction mixture was stirred at 0° C. overnight. The title compound (100 mg) was obtained after workup.
ESI-MS (m/z): 1037.5 (M+H)$^+$.

Step 8: Synthesis of 1-((R)-2-((R)-2-((R)-2-((R)-2-((2-tert-butyloxycarbonylaminoethyl)amino)-3-phenylpropionyl)-3-phenylpropionyl)-4-methylpentanamido)-6-tert-butyloxycarbonylaminohexanoyl)-4-tert-butyl oxycarbonylaminopiperidin-4-carboxylic acid (18-9)

Compound 18-8 (180 mg, 0.17 mmol) was dissolved in tetrahydrofuran (20 mL) and water (4 mL). Under the protection of nitrogen, the resultant solution was cooled to −5° C., to which lithium hydroxide (16 mg, 0.69 mmol) was added. The reaction was carried out at 0° C. for 72 h. the reaction solution was adjusted to pH=3 with 0.5 mol/L HCl. The title compound (a crude product, 160 mg) was obtained after workup, and was used directly in the next step.
ESI-MS (m/z): 1023.5 (M+H)$^+$.

Step 9: Synthesis of 4-amino-1-((R)-2-((R)-2-((R)-2-(2-aminoethylamino)-3-phenylpropionyl)-3-phenylpropionyl)-4-methylpentanamido)-6-aminohexanoyl)piperidin-4-carboxylic acid (Compound 18)

Compound 18-9 (160 mg, 0.19 mmol) was dissolved in 1,4-dioxane (20 mL), and 4M HCl/1,4-dioxane (20 mL) was added and reacted for 4 h, then the reaction mixture was subjected to the suction filtration. The filter cake was freeze-dried to obtain the product (a crude product, 120 mg). The trifluoroacetate of the title compound (43 mg) was obtained after workup.
$^1$H NMR (400 MHz, DMSO-d$_6$) δ 8.65 (s, 4H), 8.39-8.37 (m, 1H), 8.22 (d, J=8 Hz, 1H), 8.11 (d, J=8 Hz, 1H), 7.84 (s, 4H), 7.28-7.11 (m, 10H), 4.73-4.67 (m, 2H), 4.36-4.30 (m, 1H), 3.81-3.80 (m, 1H), 3.73-3.65 (m, 2H), 3.07-2.95 (m, 6H), 2.76-2.64 (m, 5H), 2.07-1.82 (m, 4H), 1.52-1.45 (m, 8H), 1.32-1.31 (m, 2H), 0.94-0.87 (m, 6H);
ESI-MS (m/z): 723.5 (M+H).

Example 19: 1-((R)-2-((R)-2-((R)-2-((R)-2-(3-aminopropylamino)-3-phenylpropionyl)-3-phenylpropionyl)-4-methylpentanamido)-6-aminohexanoyl)-4-aminopiperidin-4-carboxylic acid (Compound 19)

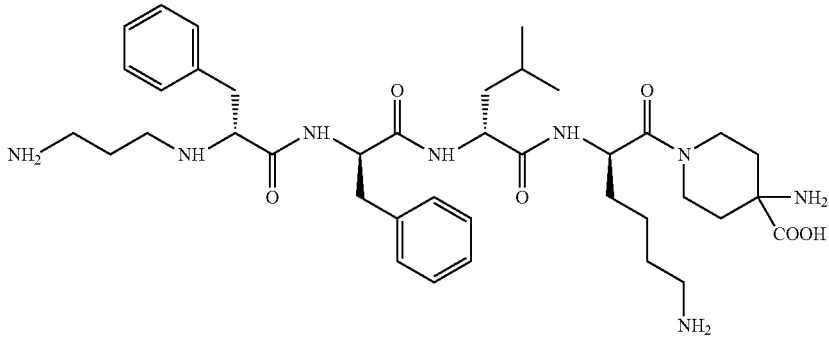 [SMILES: CC(C)C[C@@H](NC(=O)[C@@H](Cc1ccccc1)NC(=O)[C@@H](Cc1ccccc1)NCCCN)C(=O)N[C@H](CCCCN)C(=O)N1CCC(N)(C(=O)O)CC1]

In accordance with the preparation method in Example 18, the trifluoroacetate of the title compound (47 mg) is synthesized, wherein, (3-oxopropyl)aminocarbamate tert-butyl was used in Step 7.
$^1$H NMR (400 MHz, DMSO-d$_6$) δ 8.90-7.94 (m, 11H), 7.33-7.02 (m, 10H), 4.75-4.69 (m, 2H), 4.29-4.27 (m, 1H), 3.92-3.82 (m, 1H), 3.67-3.59 (m, 3H), 3.07-2.95 (m, 7H), 2.74-2.68 (m, 5H), 2.09-1.98 (m, 2H), 1.86-1.76 (m, 2H), 1.64-1.45 (m, 8H), 1.33-1.28 (m, 2H), 0.95-0.88 (m, 6H);
ESI-MS (m/z): 737.5 (M+H)$^+$.

Example 20: 4-amino-1-((R)-6-amino-2-((R)-2-((R)-2-((S)-3-amino-2-benzylpropanamido)-3-phenylpropanamido)-4-methylpentanamido)hexanoyl)piperidin-4-carboxylic acid (Compound 21)
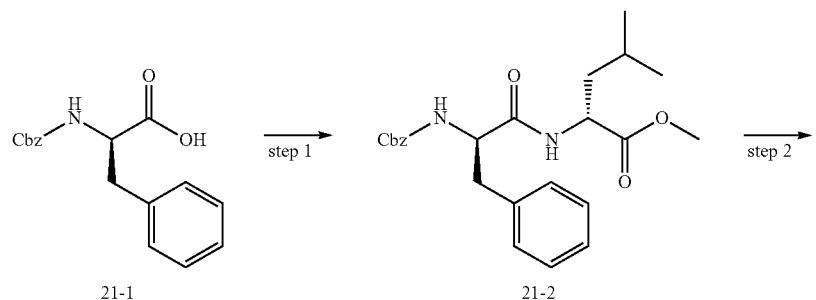
21-1    21-2
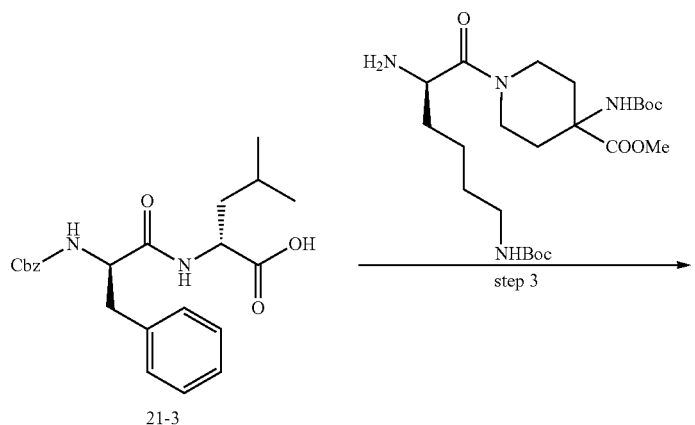
21-3
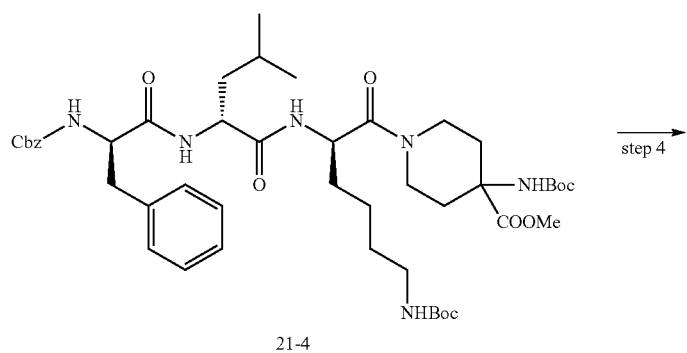
21-4
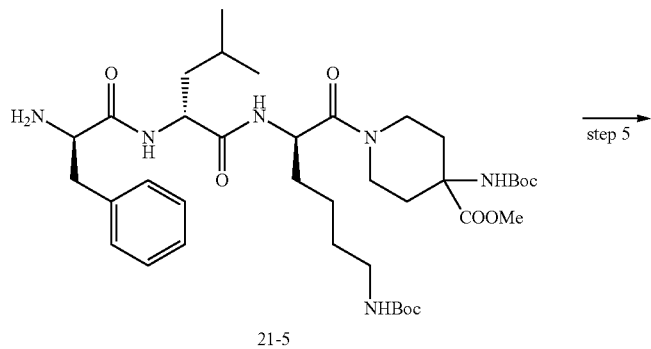
21-5

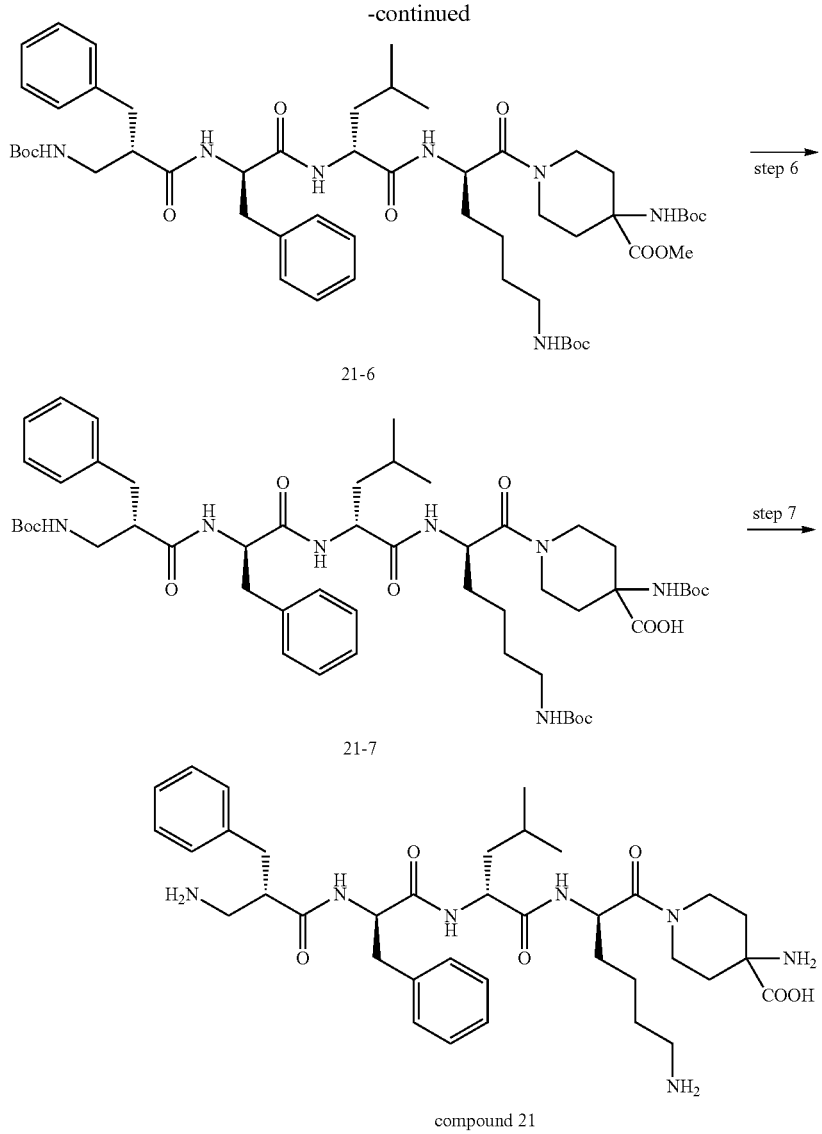

compound 21

Step 1: Synthesis of methyl ((R)-2-((R)-2-(benzyloxycarbonylamino)-3-phenylpropanamido)-4-methylvalerate (21-2)

N-benzyloxycarbonyl-D-phenylalanine (1.00 g, 3.33 mmol), D-leucine methyl ester hydrochloride (0.73 g, 4.00 mmol), DIEA (1.72 g, 13.30 mmol) and copper chloride dehydrate (0.68 g, 4.00 mmol) were dissolved in tetrahydrofuran (30 mL). Under the protection of nitrogen, the resultant mixture was cooled to −5° C., to which HOBt (0.68 g, 5.00 mmol), and HBTU (1.90 g, 5.00 mmol) were added. The reaction was carried out at 0° C. overnight. The title compound (a crude product, 1.40 g) was obtained after workup, and was used directly in the next step.

ESI-MS (m/z): 427 (M+H)$^+$.

Step 2: Synthesis of (R)-2-((R)-2-(benzyloxycarbonylamino)-3-phenylpropanamido)-4-methylvaleric acid (21-3)

Compound 21-2 (1.40 g, 3.28 mmol) was dissolved in a mixed solvent of tetrahydrofuran (30 mL) and water (6 mL). The resultant mixture was cooled to −5° C., to which lithium hydroxide (0.16 g, 6.57 mmol) was added. The reaction was carried out at 0° C. for 2 h. The resultant mixture was then diluted with 100 mL ice-water, and adjusted to pH=3 with 0.5 mol/L HCl. The title compound (a crude product, 1.28 g) was obtained after workup, and was used directly in the next step.

ESI-MS (m/z): 413 (M+H).

Step 3: Synthesis of methyl 1-((R)-2-((R)-2-((R)-2-benzyloxycarbonylamino-3-phenylpropanamido)-4-methylpentanamido)-6-tert-butyloxycarbonylamino-hexanamido)-4-tert-butyloxycarbonylaminopiperidin-4-carboxyl ate (21-4)

Compound 21-3 (1.28 g, 3.10 mmol) and Compound 18-5 (1.51 g, 3.10 mmol) were dissolved in dichloromethane (40 mL). Under the protection of nitrogen, the resultant mixture was cooled to −5° C., to which N-methylmorpholine (0.94 g, 9.30 mmol), HOBt (0.63 g, 4.65 mmol), and 1-(3-dimethylaminopropyl)-3-ethylcarbodiimide hydrochloride (0.89 g, 4.65 mmol) were added. The reaction was carried out at 0° C. overnight. The title compound (a crude product, 2.2 g) was obtained after workup, and was used directly in the next step.

Step 4: Synthesis of methyl 1-((R)-2-((R)-2-((R)-2-amino-3-phenylpropanamido)-4-methylpentanamido)-6-tert-butyloxycarbonylaminohexanoyl)-4-tert-butyloxycarbonylaminopiperidin-4-carboxylate (21-5)

Compound 21-4 (600 mg, 0.68 mmol) was dissolved in methanol (15 mL), 10% Pd/C (60 mg) was added, and the replacement with $H_2$ was performed. The reaction was carried out at room temperature for 3 h. After filtration through diatomite, washing with methanol, and drying by rotary evaporation, the title compound (480 mg) was obtained.
ESI-MS (m/z): 747.5 (M+H)⁺.

Step 5: Synthesis of methyl 1-((R)-2-((R)-2-((R)-2-((S)-3-tert-butyloxycarbonylamino-2-benzylpropanamido)-3-phenylpropanamido)-4-methylpentanamido)-6-tert-butyloxycarbonylaminohexanoyl)-4-tert-butyloxycarbonylaminopiperidin-4-carboxylate (21-6)

Compound 21-5 (320 mg, 0.43 mmol) and (S)-2-benzyl-3-N-tert-butyloxycarbonylaminopropionic acid (120 mg, 0.43 mmol) were dissolved in dichloromethane (20 mL). Under the protection of nitrogen, the resultant mixture was cooled to −5° C., to which N-methylmorpholine (130 mg, 1.29 mmol), HOBt (87 mg, 0.64 mmol), and 1-(3-dimethylaminopropyl)-3-ethylcarbodiimide hydrochloride (123 mg, 0.64 mmol) were added. The reaction was carried out at 0° C. overnight. The title compound (280 mg) was obtained after workup.
ESI-MS (m/z): 1008.5 (M+H)⁺

Step 6: Synthesis of 1-((R)-2-((R)-2-((R)-2-((S)-3-tert-butyloxycarbonylamino-2-benzylpropanamido)-3-phenylpropanamido)-4-methylpentanamido)-6-tert-butyloxycarbonylaminohexanoyl)-4-tert-butyloxycarbonylaminopiperidin-4-carboxylic acid (21-7)

Compound 21-6 (260 mg, 0.26 mmol) was dissolved in a mixed solvent of tetrahydrofuran (20 mL) and water (4 mL). Under the protection of $N_2$, the resultant mixture was cooled to −5° C., to which lithium hydroxide (25 m g, 1.05 mmol) was added. The reaction was performed at 0° C. for 72 h. The resultant mixture was adjusted to pH=3 with 0.5 mol/L hydrochloric acid. The title compound (a crude product, 0.20 g) was obtained after work up, and was used directly in the next step.
ESI-MS (m/z): 994.5 (M+H)⁺

Step 7: Synthesis of 4-amino-1-((R)-6-amino-2-((R)-2-((R)-2-((S)-3-amino-2-benzylpropanamido)-3-phenylpropanamido)-4-methylpentanamido)hexanoyl)piperidin-4-carboxylic acid (Compound 21)

Compound 21-7 (200 mg, 0.201 mmol) was dissolved in 1,4-dioxane (5 mL), and added with 4M HCl/1,4-dioxane (5 mL). The reaction was carried out for 4 h. The hydrochloride of the title compound (a crude product, 150 mg) was obtained after workup. The crude product was purified by preparative HPLC to obtain the trifluoroacetate of the title compound (89 mg).
¹H NMR (400 MHz, DMSO-d₆) δ 8.46-7.71 (m, 9H), 7.28-7.16 (m, 10H), 4.70-4.58 (m, 2H), 4.36-4.30 (m, 1H), 3.10-3.03 (m, 2H), 2.93-2.67 (m, 9H), 2.09-1.97 (m, 3H), 1.73-1.45 (m, 11H), 1.30-1.27 (m, 2H), 0.90-0.85 (m, 6H).
ESI-MS (m/z): 694.5 (M+H)⁺.

Example 21: 4-amino-1-((R)-6-amino-2-((R)-2-((R)-2-((R)-3-amino-2-benzylpropanamido)-3-phenylpropanamido)-4-methylpentanamido)hexanoyl)piperidin-4-carboxylic acid (Compound 22)

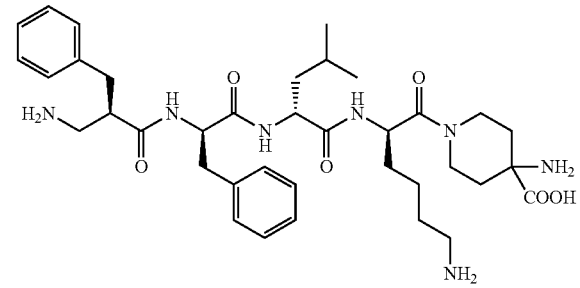 [SMILES: CC(C)C[C@@H](NC(=O)[C@@H](Cc1ccccc1)NC(=O)[C@@H](CN)Cc1ccccc1)C(=O)N[C@H](CCCCN)C(=O)N1CCC(N)(C(=O)O)CC1]

In accordance with the preparation method in Example 20, the hydrochloride of the title compound (a crude product, 250 mg) is synthesized, wherein, (R)-2-benzyl-3-N-tert-butyloxycarbonylaminopropionic acid was used in Step 5. The crude product was purified by preparative HPLC to obtain the trifluoroacetate of the title compound (184 mg).
¹H NMR (400 MHz, DMSO-d₆) δ 8.41-7.72 (m, 10H), 7.22-7.16 (m, 8H), 7.05-7.01 (m, 2H), 4.72-4.60 (m, 2H), 4.36-4.23 (m, 4H), 2.85-2.67 (m, 8H), 2.04-1.96 (m, 2H), 1.62-1.51 (m, 10H), 1.35-1.23 (m, 3H), 0.92-0.85 (m, 6H);
ESI-MS (m/z): 694.5 (M+H)⁺.

Example 22: 8-((R)-2-((R)-2-((R)-2-((R)-2-amino-3-phenylpropanamido)-3-phenylpropanamido)-4-methylpentanamido)-6-(2-(methoxyethoxy)ethylamino)hexanoyl)-2,8-diaza-spiro[4.5]decan-3-one (Compound 23)

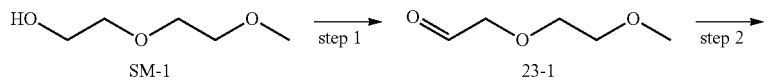

-continued
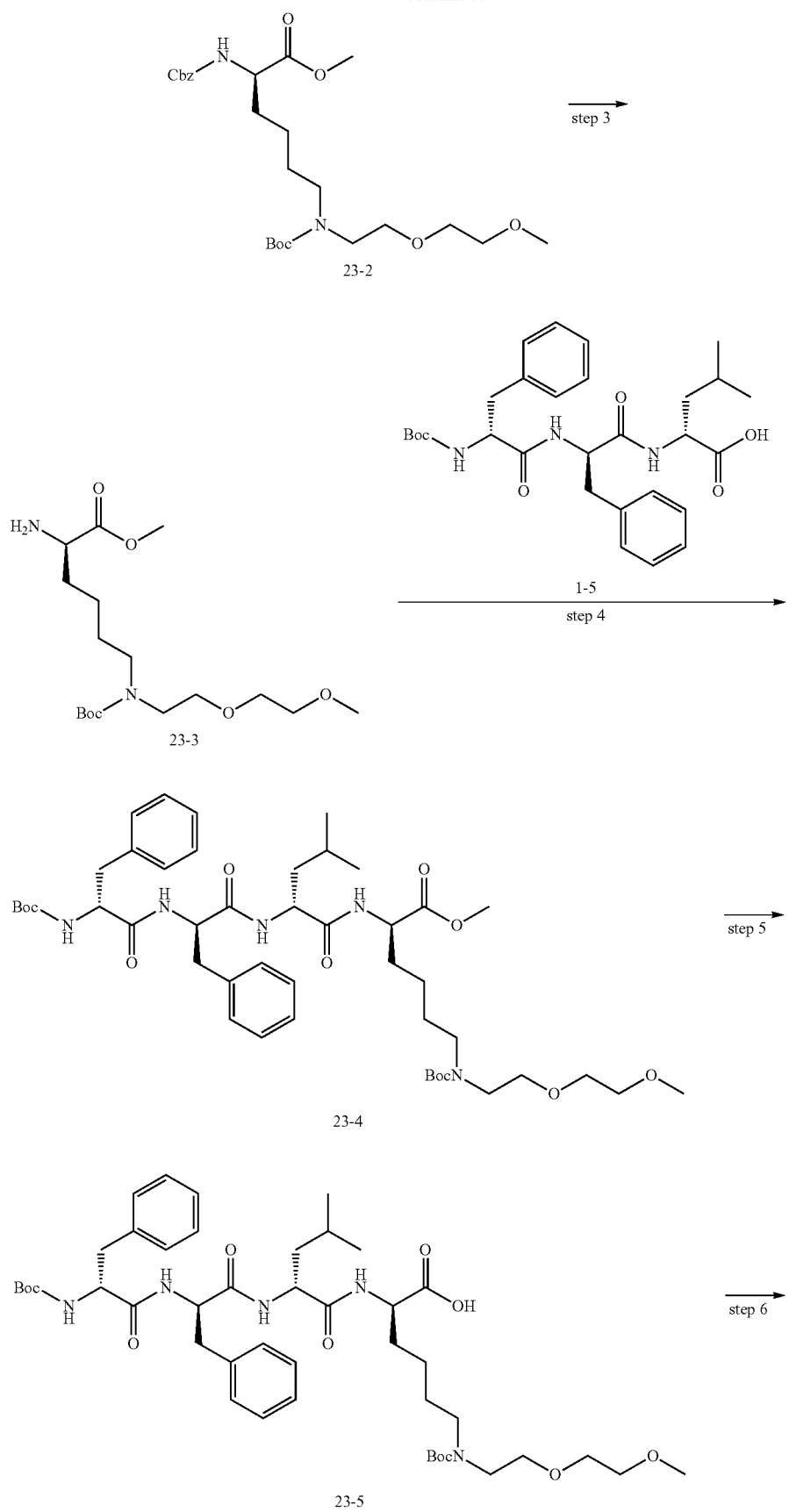

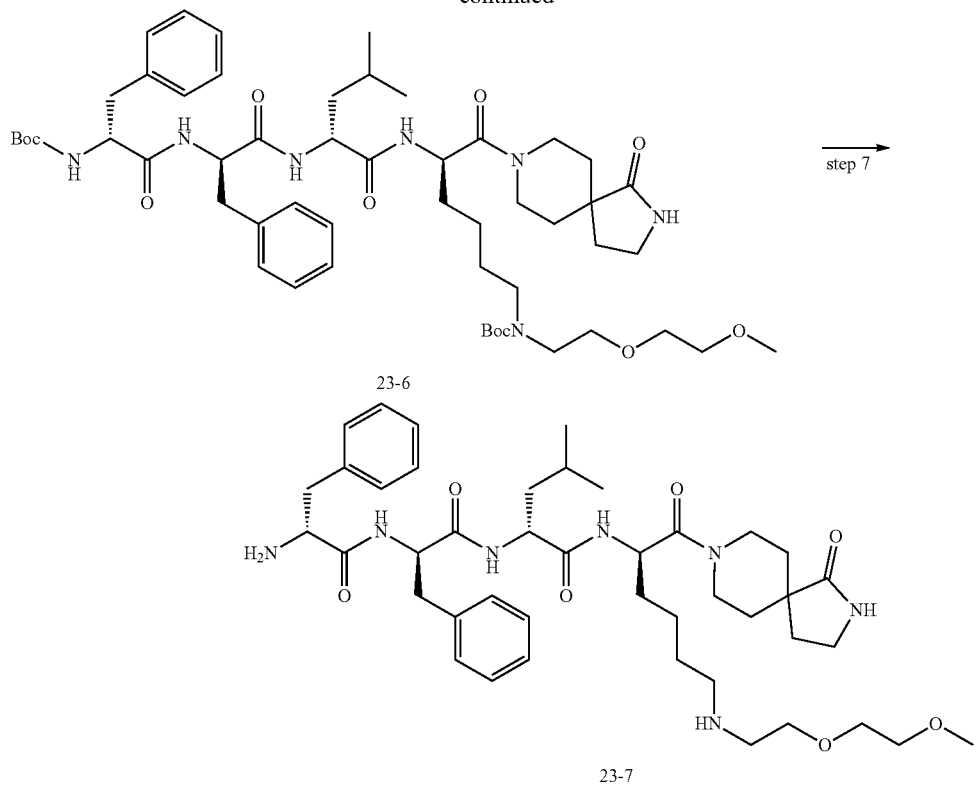

Step 1: Synthesis of 2-(2-methoxyethoxy)acetaldehyde (23-1)

Oxalyl chloride (8.87 g, 69.91 mmol) was dissolved in dichloromethane (80 ml) under the protection of nitrogen, and was cooled to <−70° C. A solution of dimethyl sulfoxide (7.8 g, 99.87 mmol) in dichloromethane (10 mL) was added dropwise and stirred at the temperature for 60 min after the addition; then followed by an addition of a solution of diethylene glycol monomethyl ether (8.0 g, 66.58 mmol) in dichloromethane (10 mL) dropwisely. A further stirring of 60 min at the temperature was conducted; triethylamine (13.47 g, 133.16 mmol) was added dropwise. After the addition, the temperature was warmed to room temperature slowly. The stirring was performed for 20 min to obtain the solution of the title compound in dichloromethane (143 mL), in which the content of the title compound was about 54 mg/mL.

Step 2: Synthesis of methyl (R)-2-benzyloxycarbonylamino-6-(N-tert-butyloxycarbonyl-N-(2-(2-methoxyethoxy)ethyl)amino)hexanoate (23-2)

To a solution of N-(9-benzyloxycarbonyl)-D-lysine hydrochloride (1.2 g, 3.63 mmol) in methanol (3.0 mL), a solution of Compound 23-1 in dichloromethane (15 mL, 5.63 mmol) was added. After stirring at room temperature for 30 min, sodium triacetoxyborohydride (1.9 g, 8.89 mmol) was added. The resultant reaction mixture was reacted at room temperature for 30 min. A mixture of DIEA (1.15 g, 8.89 mmol) and di-tert butyl dicarbonate (712 mg, 3.26 mmol) was cooled to 0° C., and then added to the solution above. After the addition, the resultant mixture was warmed to room temperature and reacted for 2 h. The title compound (750 mg) was obtained after workup.

Step 3: Synthesis of methyl (R)-2-amino-6-(N-tert-butyloxycarbonyl-N-(2-(2-methoxyethoxy)ethyl)amino)hexanoate (23-3)

Compound 23-2 (750 mg, 1.51 mmol) was dissolved in 10 mL methanol, and added with Pd/C (10%). The reaction was performed at the atmosphere of hydrogen for 2 h. Pd/C was removed by filtration, and the title compound (520 mg) was obtained by concentration under reduced pressure.

Step 4: Synthesis of methyl (R)-2-((R)-2-((R)-2-((R)-2-tert-butyloxycarbonylamino-3-phenylpropanamido)-3-phenylpropanamido)-4-methylpentanamido)-6-(N-tert-butyloxycarbonyl-N-(2-(2-methoxyethoxy)ethyl)amino) hexanoate (23-4)

Compound 1-5 (750 mg, 1.43 mmol) and Compound 23-3 (520 mg, 1.43 mmol) were dissolved in 10 mL tetrahydrofuran. The resultant mixture was cooled to 0° C., to which DIEA (590 mg, 4.58 mmol), copper dichloride dihydrate (267 mg, 1.57 mmol), HOBt (232 mg, 1.72 mmol) and HBTU (652 mg, 1.72 mmol) were added. Under the protection of nitrogen, the reaction was performed at 0° C. for 12 h. The title compound (a crude product, 1.0 g) was obtained after workup.

Step 5: Synthesis of (R)-2-((R)-2-((R)-2-((R)-2-tert-butyloxycarbonylamino-3-phenylpropanamido)-3-phenylpropanamido)-4-methylpentanamido)-6-(N-tert-butyloxycarbonyl-N-(2-(2-methoxyethoxy)ethyl)amino) hexanoic acid (23-5)

Compound 23-4 (1.0 g, 1.15 mmol) was dissolved in a mixed solvent of 8 mL tetrahydrofuran and 2 mL water.

Lithium hydroxide monohydrate (193 mg, 4.6 mmol) was added. The reaction was performed at 0° C. for 18 h. The resultant mixture was adjusted to pH=4-5 with 1.0 mol/L dilute hydrochloric acid. The title compound (a crude product, 980 mg) was obtained after workup, and was used directly in the next step.

Step 6: Synthesis of 8-((R)-2-((R)-2-((R)-2-((R)-2-tert-butyloxycarbonylamino-3-phenylpropanamido)-3-phenylpropanamido)-4-methylpentanamido)-6-(N-tert-butyloxycarbonyl-N-(2-(2-methoxyethoxy)ethyl)amino)hexanoyl)-2,8-diaza-spiro[4.5]decan-3-one (23-6)

Compound 23-5 (200 mg, 0.23 mmol) and 2,8-diazaspiro[4.5]decan-1-one (46 mg, 0.24 mmol) were dissolved in N,N-dimethyllformamide (10 mL). The resultant mixture was cooled to 0° C. DIEA (89 mg, 0.69 mmol) and HBTU (261 mg, 0.69 mmol) were added. The reaction was performed at 0° C. for 12 h. The title compound (a crude product, 220 mg) was obtained after workup, and was used directly in the next step.

Step 7: Synthesis of 8-((R)-2-((R)-2-((R)-2-((R)-2-amino-3-phenylpropanamido)-3-phenylpropanamido)-4-methylpentanamido)-6-(2-(methoxyethoxy)ethylamino)hexanoyl)-2,8-diaza-spiro[4.5]decan-3-one (Compound 23)

Compound 23-6 (220 mg, 0.22 mmol) was added in a 50 mL reaction bottle, followed by 10 mL HCl/1,4-dioxane (4.0 mol/L). The reaction was carried out at room temperature for 2 h. The crude product of the title compound (200 mg) was obtained directly by concentration under reduced pressure. After purification by preparative HPLC, the trifluoroacetate of the title compound (37 mg) was obtained.

$^1$H NMR (400 MHz, DMSO-d$_6$) δ 8.77 (t, J=8 Hz, 1H), δ 8.49 (s, 2H), 8.38 (d, J=8 Hz, 1H), 8.21-8.02 (m, 4H), 7.64 (d, J=9.6 Hz, 1H), 7.32-7.20 (m, 10H), 4.72-4.63 (m, 2H), 4.42-4.34 (m, 1H), 4.23-4.09 (m, 1H), 4.00 (s, 1H), 3.91-3.83 (m, 1H), 3.63 (t, J=5.2 Hz, 2H), 3.57-3.55 (m, 2H), 3.47-3.45 (m, 2H), 3.24 (s, 3H), 3.20-3.07 (m, 7H), 2.94-2.77 (m, 5H), 1.99-1.96 (m, 2H), 1.64-1.60 (m, 5H), 1.55-1.42 (m, 4H), 1.40-1.25 (m, 4H), 0.92-0.82 (m, 6H);
ESI-MS (m/z): 792.49 (M+H)$^+$.

Example 23: 8-((R)-2-((R)-2-((R)-2-((R)-2-amino-3-phenylpropanamido)-3-phenylpropanamido)-4-methylpentanamido)-6-(2-(methoxyethoxy)ethylamino)hexanoyl)-1,3,8-triaza-spiro[4.5]decane-2,4-dione (Compound 24)

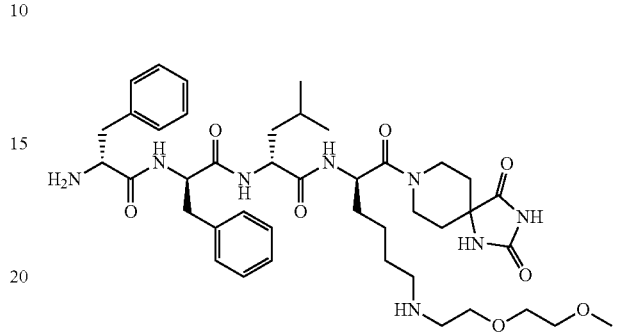

In accordance with the preparation method in Example 22, a crude product of the title compound (200 mg) was obtained, wherein, 1,3,8-triaza-spiro[4.5]decane-2,4-dione was used in Step 6. After purification by preparative HPLC, the trifluoroacetate of the title compound (31 mg) was obtained.

$^1$H NMR (400 MHz, DMSO-d$_6$) δ 10.77 (d, J=12 Hz, 1H), 8.75 (t, J=4 Hz, 1H), 8.65 (d, J=12 Hz, 1H), 8.46 (s, 2H), 8.37 (d, J=4 Hz, 1H), 8.31-8.15 (m, 1H), 8.01 (s, 3H), 7.30-7.22 (m, 10H), 4.72-4.67 (m, 2H), 4.41-4.34 (m, 1H), 4.26-4.13 (m, 1H), 3.99-3.87 (m, 2H), 3.63 (t, J=4 Hz, 2H), 3.58-3.55 (m, 2H), 3.47-3.45 (m, 2H), 3.24 (s, 3H), 3.12-3.05 (m, 5H), 2.99-2.77 (m, 5H), 1.83-1.74 (m, 1H), 1.64-1.44 (m, 10H), 1.32-1.28 (m, 2H), 0.92-0.87 (m, 6H);
ESI-MS (m/z): 807.47 (M+H).

Example 24: 2-(6-((R)-2-((R)-2-((R)-2-((R)-2-amino-3-phenylpropanamido)-3-phenylpropanamido)-4-methyl pentanamido)-6-((2-(2-methoxyethoxy)ethyl)amino)hexanoyl)-3,6-diazabicyclo[3.1.1]heptan-3-yl)acetic acid (Compound 25)

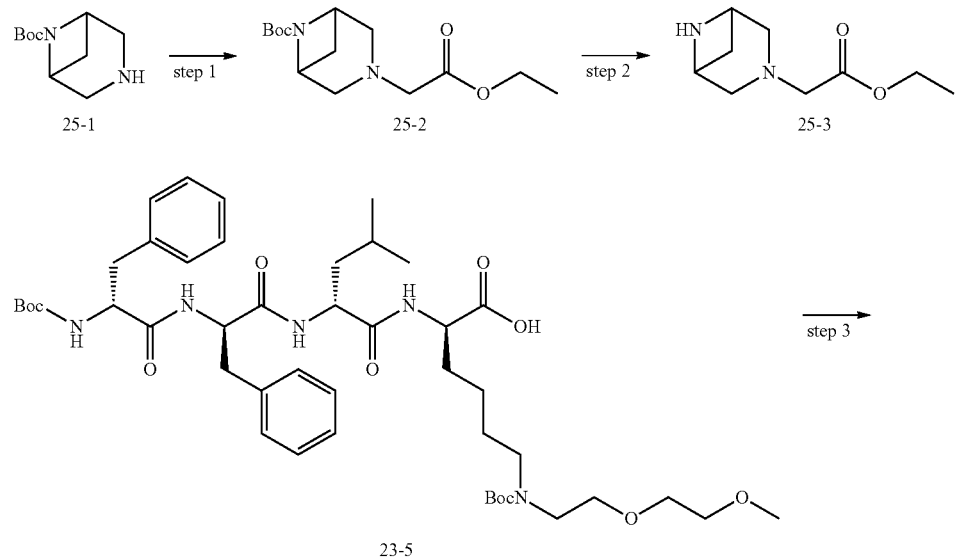

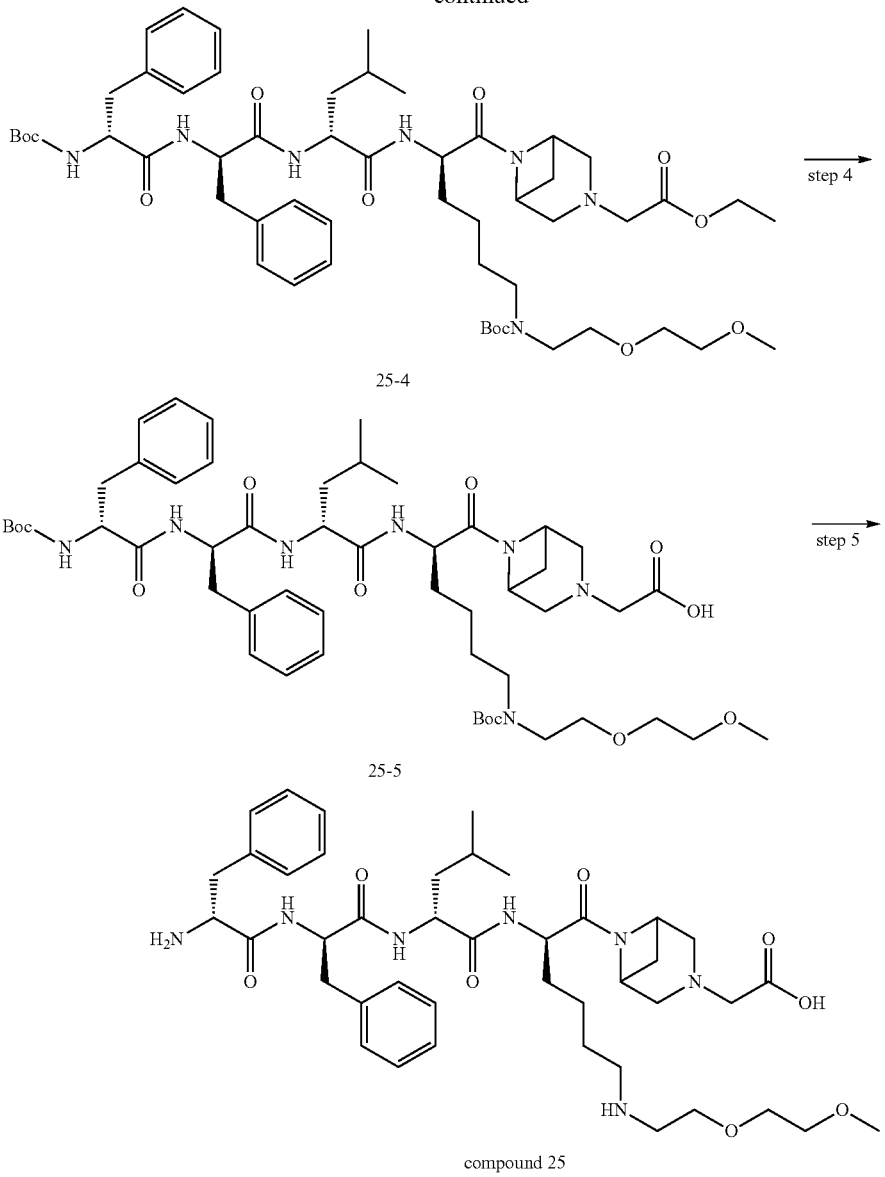

compound 25

Step 1: Synthesis of ethyl 2-(6-tert-butyloxycarbonyl-3,6-diaza bicyclo[3.1.1]heptan-3-yl)acetate (25-2)

6-Tert-butyloxycarbonyl-3,6-diazabicyclo[3.1.1]heptane (100 mg, 0.50 mmol) and ethyl glyoxylate (50% toluene, wt %) (103 mg, 1.0 mmol) were dissolved in 10 mL dichloromethane, and a little amount of glacial acetic acid was added. The resultant mixture was stirred at room temperature for 20 min, followed by an addition of sodium triacetoxyborohyride (534 mg, 2.52 mmol). The reaction was carried out at room temperature for 30 min. The title compound (a crude product, 300 mg) was obtained after workup, and was used directly in the next step.

Step 2: Synthesis of ethyl 2-(3,6-diazabicyclo[3.1.1]heptan-3-yl)acetate (25-3)

Compound 25-2 (300 mg, 1.06 mmol) was dissolved in 3 mL dichloromethane, and added with 1.0 mL trifluoroacetic acid. The resultant reaction mixture was stirred at room temperature for 2 h. The title compound (a crude product, 200 mg) was obtained after workup, and was used directly in the next step.

Step 3: Synthesis of ethyl 2-(6-((R)-2-((R)-2-((R)-2-((R)-2-tert-butyloxycarbonylamino-3-phenylpropanamido)-3-phenylpropanamido)-4-methylpentanamido)-6-(N-tert-butyloxycarbonyl-N-(2-(2-methoxyethoxy)ethyl)amino)hexanoyl)-3,6-diazabicyclo[3.1.1]heptan-3-yl)acetate (25-4)

Compound 23-5 (220 mg, 0.25 mmol) and Compound 25-3 (56 mg, 0.31 mmol) were dissolved in 10 mL N,N-dimethyllformamide. The resultant mixture was cooled to 0° C., and added with DIEA (105 mg, 0.81 mmol) and HBTU (308 mg, 0.81 mmol). The reaction was carried out at 0° C.

for 12 h. The title compound (a crude product, 250 mg) was obtained after workup, and was used directly in the next step.

Step 4: Synthesis of 2-(6-((R)-2-((R)-2-((R)-2-((R)-2-tert-butyloxycarbonylamino-3-phenylpropanamido)-3-phenylpropanamido)-4-methylpentanamido)-6-(N-tert-butyloxycarbonyl-N-(2-(2-methoxyethoxy)ethyl)amino)hexanoyl)-3,6-diazabicyclo[3.1.1]heptan-3-yl)acetic acid (25-5)

Compound 25-4 (250 mg, 0.24 mmol) was dissolved in 8 mL tetrahydrofuran, and added with 2 mL water. The resultant mixture was cooled to 0° C., to which lithium hydroxide (40 mg, 0.96 mmol) was added. The reaction was carried out overnight at this temperature. The resultant mixture was adjusted to pH=4-5 with 1.0 mol/L diluted hydrochloric acid. The title compound (a crude product, 230 mg) was obtained after workup, and was directly used in the next step.

Step 5: Synthesis of 2-(6-((R)-2-((R)-2-((R)-2-((R)-2-amino-3-phenylpropanamido)-3-phenylpropanamido)-4-methyl pentanamido)-6-((2-(2-methoxyethoxy)ethyl)amino)hexanoyl)-3,6-diazabicyclo[3.1.1]heptan-3-yl)acetic acid (Compound 25)

Compound (25-5) 230 mg was added in a 50 mL reaction bottle, and added with 10 mL HCl/1, 4-dioxane (4.0 mol/L). The reaction was carried out at room temperature for 2 h. A crude product of the title compound (200 mg) was obtained directly by concentration under reduced pressure. After purification by preparative HPLC, the trifluoroacetate of the title compound (37 mg) was obtained.

$^1$H NMR (400 MHz, DMSO-$d_6$) δ 8.75-8.73 (m, 1H), 8.48-8.42 (m, 2H), 8.37-8.33 (m, 1H), 8.25-8.23 (m, 1H), 8.01 (s, 3H), 7.29-7.20 (m, 10H), 4.67-4.63 (m, 1H), 4.55-4.53 (m, 1H), 4.43-4.32 (m, 1H), 4.26-3.95 (m, 4H), 3.65-3.47 (m, 10H), 3.25 (s, 3H), 3.09-3.01 (m, 5H), 2.92-2.76 (m, 4H), 1.99-1.80 (m, 1H), 168-1.29 (m, 10H), 0.92-0.87 (m, 6H);

ESI-MS (m/z): 794.47 (M+H)$^+$.

The other compounds could be synthesized by reference to the methods in the above Examples.

Biological Experiments

1. Experiment on κ-Opioid Receptor Agonistic Effect

The efficacy of the compounds of the invention as κ-opioid receptor agonists was determined by measuring the ability of the compounds of Examples to inhibit adenylate cyclase activity.

Cell culture: hamster ovary cells CHO stably expressing human κ-opioid receptor (KOR) gene were cultured in MEMα plus nucleosides medium (Invitrogen) containing 5% FBS.

Stimulation: the test compound was 4-fold diluted in a gradient manner to obtain 11 concentrations, and 100 nl of each was transferred to a 384-well plate, and then a stimulating solution (5 uL) containing NKH477 (Tocris) was added; the cells were digested, re-suspended, and counted; and then the cells (5 uL) were added to wells, mixed gently, and incubated at 37° C. for 30 min.

Detection: cAMP Assay Kit (Cisbio) was used, cAMP-$D_2$ and Anti-cAMP-Cryptate were added separately, and the resultant mixture was incubated for 1 h at room temperature. The plate was read using envision (Perkin Elmer) and $EC_{50}$ was obtained by means of fitting with a four-parameter equation.

| Experimental result | |
|---|---|
| Example No. | $ED_{50}$ (nM) |
| Example 1 | 0.09 |
| Example 2 | 0.08 |
| Example 3 | 0.06 |
| Example 4 | 0.07 |
| Example 5 | 0.05 |
| Example 6 | 0.11 |
| Example 8 | 0.03 |
| Example 15 | 0.06 |
| Example 17 | 0.42 |
| Example 23 | 0.016 |
| Example 24 | 0.005 |

It could be seen from the above result of $EC_{50}$: the compounds of Examples had an excellent agonistic effect for κ-opioid receptor. The other compounds of the invention had a similar agonistic effect for κ-opioid receptor.

2. Experiment on Selectivity for Opioid Receptors

The selectivity of the compounds of the invention for κ opioid receptors was determined by measuring the inhibitory effect of the compounds of Examples on the enzyme of KOR, MOR, and DOR.

Experimental Method

The compounds of Examples at different concentrations were incubated with the cell membrane with high expression of KOR, MOR, DOR and the corresponding radioligand (KOR: 3H-diprenophrine; MOR: 3H-DAMGO; DOR: 3H-DADLE) for 1 h, the compounds of Examples competed with the radioligands for binding to KOR, MOR, DOR. After the incubation, Cell harvest was used to collect cell membranes onto a Unifilter-96 GF/C filter plate, and the unbound radioligands were washed away. The plate was placed in a 50-degree oven for 1 h, and finally the scintillation solution Microscint 20 cocktail was added and the isotope signal was detected by MicroBeta2 Reader.

According to the intensity of the isotope signal at different concentrations, the $IC_{50}$ was calculated by means of fitting with a four-parameter equation, and the Ki value was calculated.

The Ki value was calculated according to the formula $Ki=IC_{50}/(1+[radioligand]/Kd)$, and Kd was the equilibrium dissociation constant of radioligand.

| | Experimental result | | | | | |
|---|---|---|---|---|---|---|
| | DOR | | MOR | | KOR | |
| Example No. | $IC_{50}$ (nM) | Ki (nM) | $IC_{50}$ (nM) | Ki (nM) | $IC_{50}$ (nM) | Ki (nM) |
| Example 3 | >20000 | >12048 | >20000 | >7182 | <0.03 | <0.01 |
| Example 4 | >20000 | >12048 | >20000 | >7182 | <0.03 | <0.01 |
| Example 5 | >20000 | >12048 | >20000 | >7182 | 0.05 | 0.02 |
| Example 6 | >20000 | >12048 | >20000 | >7182 | 0.33 | 0.11 |

It could be seen from the above results: the compounds of Example 3, 4, 5, and 6 had an excellent KOR selectivity for κ opioids. Other compounds of the invention had a similar KOR selectivity to κ opioids.

3. Acetic Acid-Induced Writhing Test in Mice (Evaluation of In Vivo Efficacy)

The analgesic effect of the compound of the invention was evaluated by measuring the ED50 of the compounds of Examples in the acetic acid-induced writhing test in mice.

Experimental Method

The commercial glacial acetic acid solution was diluted with physiological saline to 0.6% glacial acetic acid solution. The male ICR mice were randomly separated into the drug group and the model group (to which physiological saline was administration). 15 minutes after iv administration, 0.6% acetic acid solution was intraperitoneally injected at 10 ml/kg, and the mice was immediately recorded with DV camera for 15 min. After the recording, the number of writhes of the mice within 15 min was counted from the video by blind method, the inhibition rate for the writhes was calculated according to Formula (I), and the ED50 of the compound was calculated according to Formula (II).

(I) The inhibition rate for the writhes was calculated by the formula: Inhibition rate (%)=(the number of writhes in a model group−the number of writhes in a drug group)/the number of writhes in a model group*100.

(II) The $ED_{50}$ was calculated by the formula:

$$1 g\, LD_{55} = x_m - d\left(\Sigma_p - \frac{3 - pm - pm}{4}\right),$$

wherein Xm was the logarithm of the highest dose, d was the difference in the logarithm of two adjacent doses, p was the inhibition rate for each dose group, pm was the highest-dose inhibition rate, and pn was the lowest-dose inhibition rate.

| Experimental result | |
|---|---|
| Example No. | $ED_{50}$ (nM) |
| Example 3 | 0.041 |
| Example 4 | 0.029 |
| Example 5 | 0.017 |
| Example 6 | 0.036 |

As seen from the above result, the compounds of Examples 3, 4, 5, and 6 had significant analgesic effect. Other compounds of the invention had similar significant analgesic effect.

4. Pharmacokinetic (PK) Study in Rats

The pharmacokinetic profile of the compounds of Examples was studied by intravenous administration of the compounds of Examples to male SD rats. The dose for IV administration was 1 mg/kg, and the solvent was 5% DMSO: 5% solutol: 90% physiological saline. After IV administration, blood samples were collected at different time points for PK study. Plasma were treated by protein precipitation and then analyzed by LC-MS/MS.

In LC-MS/MS, mass spectrum was API 5500, and liquid chromatography was Shimadzu LC-30AD system. The column used for the test groups of Compound 3 and Compound 4 was Thermo C18 column (4.6 mm×100 mm, 3 μm); for mobile phases, phase A was water+0.1% formic acid, and phase B was methanol; the flow rate was 0.8 mL/min, and the column temperature was 40° C. The column used for the test group of Compound 5 was Agela AQ C18 column (2.1 mm×50 mm, 1.9 μm); for mobile phases, phase A was water+0.05% formic acid+5 mM acetic acid ammonium, and phase B was methanol+0.05% formic acid; the flow rate was 0.6 mL/min, and the column temperature was 40° C. The ion source used was the ESI source in positive ion mode, and the scanning mode was Multiple Reaction Monitoring (MRM).

| Experimental result | | | | | |
|---|---|---|---|---|---|
| / | | Example 3 | Example 4 | Example 5 | Example 6 |
| | | \multicolumn{4}{c}{Administration route} |
| | | Intravenous administration | Intravenous administration | Intravenous administration | Intravenous administration |
| | | \multicolumn{4}{c}{Gender} |
| | | male | male | male | male |
| Dose | mg/kg | 1 | 1 | 1 | 1 |
| $AUC_{last}$ | h*ng/ml | 1790 | 2410 | 783 | 2180 |
| $C_{max}$ | ng/ml | 2650 | 3590 | 1690 | 3660 |
| $T_{1/2}$ | h | 0.34 | 1.22 | 0.28 | 0.29 |
| $V_d$ | l/kg | 0.28 | 0.74 | 0.53 | 0.20 |

It was found by the PK study in rats that, the compounds of Example 3, 4, 5, and 6 had good exposure amount and Cmax, as well as other parameters. It indicated that the compounds of the present invention had good pharmacokinetics and absorption, and had significant pharmacokinetic and absorption effect.

5. Experiment on the Ability of Compounds to Pass Through the Blood-Brain Barrier After peripheral intravenous administration of the compound of each Example to the animal, samples of peripheral plasma and brain tissue were taken to determine the concentration of the compound in the peripheral plasma and brain tissue.

After intravenously injected with the compound of Example 5 at 1 mg/kg to male rats, samples of plasma and brain tissues were taken at various time points, and the contents of the test compound in the peripheral plasma and brain tissue were determined. The results were shown in the following table:

| Time after administration (min) | Concentration of the compound of Example 5 in peripheral plasma ng/mL | Concentration of the compound of Example 5 in brain tissue ng/mL |
|---|---|---|
| 5 | 1310 | 0 |
| 15 | 716 | 0 |
| 30 | 386 | 0.20 |
| 60 | 136 | 0.00 |

The experimental result above showed that the concentration of the test compound in the peripheral plasma was significantly higher than that in the brain tissue. It indicated that the compound of the invention could effectively reduce the toxic side effects (such as analgesia, sedation, hallucination or addiction, etc.) to the central nervous system whilst remaining the peripheral analgesic effect.

In addition to those described herein, various modifications of the invention will be apparent to those skilled in the art according to the contents as described above. It is also intended that such modifications fall into the scope of the set of claims attached.

The invention claimed is:

1. A compound having a structure of Formula (II):

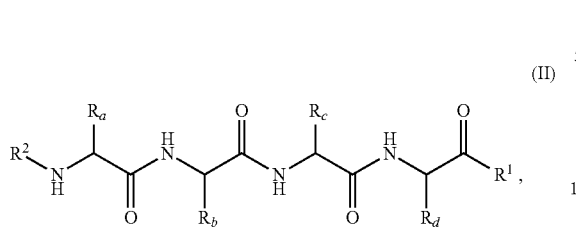

(II)

or a stereoisomer, a crystalline polymorph, a solvate, a prodrug, or a pharmaceutically acceptable salt or ester thereof, wherein $R_a$, $R_b$ and $R_c$ are substituents independently selected from the group consisting of: $(CH_3)_2CHCH_2—$ and

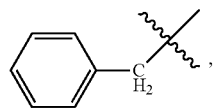 [SMILES: *Cc1ccccc1]

$R_d$ is selected from the group consisting of: $H_2NCH_2—$, $H_2NCH_2CH_2—$, $H_2N(CH_2)_2CH_2—$, $H_2N(CH_2)_3CH_2—$, $H_2N(CH_2)_4CH_2—$, $H_2N(CH_2)_5CH_2—$, $H_2NC(=NH)CH_2—$, $H_2NC(=NH)NHCH_2—$, $H_2NC(=NH)NHCH_2CH_2—$, $H_2NC(=NH)NH(CH_2)_2CH_2—$, and $H_2NC(=NH)NH(CH_2)_3CH_2—$, wherein $R_d$ is optionally substituted with one or more of $C_{1-4}$ alkyl, and wherein $R_d$ is substituted with one or more W groups, wherein the W group is selected from the group consisting of $HOCH_2(CHOH)_nCH_2—$, $(HOCH_2)_2CH—$, $—(CH_2)_aNH_2$, and $R^3O(CH_2CH_2O)_mCH_2CH_2—$;

$R^1$ is selected from the group consisting of:

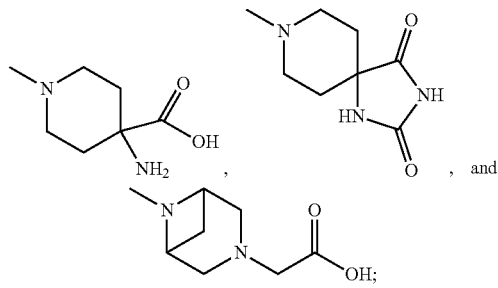

, and $R^2$ is —H;
$R^3$ is $C_{1-4}$alkyl;
each n is independently an integer from 1 to 8; and,
m is an integer from 1 to 20.

2. The compound of claim 1, or the stereoisomer, the crystalline polymorph, the solvate, the prodrug or the pharmaceutically acceptable salt or ester thereof wherein the compound has a structure of Formula (III):

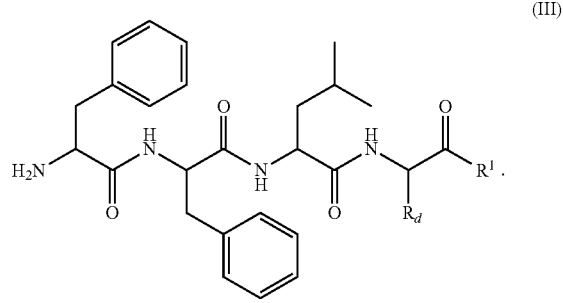

(III)

3. The compound of claim 1, or the stereoisomer, the crystalline polymorph, the solvate, the prodrug or the pharmaceutically acceptable salt or ester thereof, wherein m is an integer 1, 2, 3, 4, 5, 6, 7, 8, 9, 10 or 11.

4. The compound of claim 1, or the stereoisomer, the crystalline polymorph, the solvate, the prodrug or the pharmaceutically acceptable salt or ester thereof, wherein the compound is selected from the group consisting of:

4-amino-1-((R)-2-((R)-2-((R)-2-((R)-2-amino-3-phenylpropanamido)-3-phenylpropanamido)-4-methylpentanamido)-6-(((R)-2,3-dihydroxypropyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-(((S)-2,3-dihydroxypropyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((2-aminoethyl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((3-aminoprop yl)amino)hexano yl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((2-(2-methoxyethoxy)ethyl)amino)hexanoyl)piperidin-4-carboxylic acid;

4-amino-1-((R)-28-((R)-2-((R)-2-((R)-2-amino-3-phenylpropanamido)-3-phenylpropanamido)-4-methylpentanamido)-2,5,8,11,14,17,20-heptaoxa-23-azanonacosan-29-oyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-((1,3-dihydroxypropan-2-yl)amino)hexanoyl)piperidin-4-carboxylic acid;

4-amino-1-((R)-2-((R)-2-((R)-2-((R)-2-amino-3-phenylpropanamido)-3-phenylpropanamido)-4-methylpentanamido)-6-(di(2-(2-methoxyethoxy)ethyl)amino)hexanoyl)piperidin-4-carboxylic acid;

8-((R)-2-((R)-2-((R)-2-((R)-2-amino-3-phenylpropanamido)-3-phenylpropanamido)-4-methylpentanamido)-6-(2-(methoxyethoxy)ethylamino)hexanoyl)-1,3,8-triaza-spiro[4.5]decane-2,4-dione; and 2-(6-((R)-2-((R)-2-((R)-2-((R)-2-amino-3-phenylpropanamido)-3-phenylpropanamido)-4-methylpentanamido)-6-((2-(2-methoxyethoxy)ethyl)amino)hexanoyl)-3,6-diazabicyclo[3.1.1]heptan-3-yl)acetic acid.

5. A pharmaceutical composition comprising a therapeutically effective amount of the compound according to claim 1 and one or more pharmaceutically acceptable carriers.

6. The pharmaceutical composition according to claim 5, wherein the pharmaceutical composition is administered orally, intravenously, intraarterially, subcutaneously, intraperitoneally, intramuscularly or transdermally.

7. The compound, or the stereoisomer, the crystalline polymorph, the solvate, the prodrug or the pharmaceutically acceptable salt or ester thereof, according to claim 1, wherein n is an integer from 1 to 5.

8. The compound, or the stereoisomer, the crystalline polymorph, the solvate, the prodrug or the pharmaceutically acceptable salt or ester thereof, according to claim 1, wherein W is HOCH$_2$CH(OH)CH$_2$—, (HOCH$_2$)$_2$CH—, —CH$_2$NH$_2$, —(CH$_2$)$_2$NH$_2$, —(CH$_2$)$_3$NH$_2$, CH$_3$O(CH$_2$CH$_2$O)CH$_2$CH$_2$—, CH$_3$O(CH$_2$CH$_2$O)$_2$CH$_2$CH$_2$—, CH$_3$O(CH$_2$CH$_2$O)$_3$CH$_2$CH$_2$—, CH$_3$O(CH$_2$CH$_2$O)$_6$CH$_2$CH$_2$—, or CH$_3$O(CH$_2$CH$_2$O)$_{11}$CH$_2$CH$_2$.

9. The compound, or the stereoisomer, the crystalline polymorph, the solvate, the prodrug or the pharmaceutically acceptable salt or ester thereof, according to claim 1, wherein the compound has a structure of Formula (III)-1:

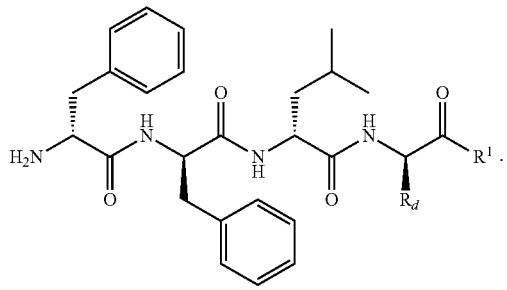

(III)-1

10. The compound, or the stereoisomer, the crystalline polymorph, the solvate, the prodrug or the pharmaceutically acceptable salt or ester thereof, according to claim 9, wherein R$_d$ is substituted with one or two W groups.

11. The compound, or the stereoisomer, the crystalline polymorph, the solvate, the prodrug or the pharmaceutically acceptable salt or ester thereof, according to claim 9, wherein
substitution of R$_d$ with one W group forms a group, which is selected from the group consisting of: W—NHCH$_2$—, W—NHCH$_2$CH$_2$—, W—NH(CH$_2$)$_2$CH$_2$—, W—NH(CH$_2$)$_3$CH$_2$—, W—NH(CH$_2$)$_4$CH$_2$—, W—NH(CH$_2$)$_5$CH$_2$—, W—NHC(=NH)CH$_2$—, W—NHC(=NH)NHCH$_2$—, W—NHC(=NH)NHCH$_2$CH$_2$—, W—NHC(=NH)NH(CH$_2$)$_2$CH$_2$—, and W—NHC(=NH)NH(CH$_2$)$_3$CH$_2$—, wherein W is selected from the group consisting of HOCH$_2$(CHOH)$_n$CH$_2$—, (HOCH$_2$)$_2$CH—, —(CH$_2$)$_n$NH$_2$, and R$^3$O(CH$_2$CH$_2$O)$_m$CH$_2$CH$_2$—, wherein
n is independently an integer from 1-8;
m is an integer from 1-20; and
R$^3$ is methyl, ethyl, n-propyl, isopropyl, n-butyl, isobutyl or tert-butyl.

12. The compound, or the stereoisomer, the crystalline polymorph, the solvate, the prodrug or the pharmaceutically acceptable salt or ester thereof, according to claim 9, wherein
substitution of R$_d$ with one W group forms a group, which is W—NH(CH$_2$)$_3$CH$_2$—;

wherein W is selected from the group consisting of HOCH$_2$(CHOH)$_n$CH$_2$—, (HOCH$_2$)$_2$CH—, —(CH$_2$)$_n$NH$_2$, and R$^3$O(CH$_2$CH$_2$O)$_m$CH$_2$CH$_2$—, wherein n is an integer from 1-8;
R$^3$ is methyl, ethyl, n-propyl, isopropyl, n-butyl, isobutyl or tert-butyl; and
m is 1, 2, 3, 4, 5, 6, 7, 8, 9, 10, 11, 12, 13, 14, 15, or 20.

13. The compound, or the stereoisomer, the crystalline polymorph, the solvate, the prodrug or the pharmaceutically acceptable salt or ester thereof, according to claim 9, wherein
substitution of R$_d$ with one W group forms a group, which is W—NH(CH$_2$)$_3$CH$_2$—;
wherein the W group is HOCH$_2$CHOHCH$_2$—, (HOCH$_2$)$_2$CH—, —CH$_2$NH$_2$, —(CH$_2$)$_2$NH$_2$, —(CH$_2$)$_3$NH$_2$, CH$_3$O(CH$_2$CH$_2$O)CH$_2$CH$_2$—, CH$_3$O(CH$_2$CH$_2$O)$_2$CH$_2$CH$_2$—, CH$_3$O(CH$_2$CH$_2$O)$_3$CH$_2$CH$_2$—, CH$_3$O(CH$_2$CH$_2$O)$_6$CH$_2$CH$_2$—, or CH$_3$O(CH$_2$CH$_2$O)$_{11}$CH$_2$CH$_2$—.

14. The compound, or the stereoisomer, the crystalline polymorph, the solvate, the prodrug or the pharmaceutically acceptable salt or ester thereof, according to claim 9, wherein
substitution of R$_d$ with one W group forms a group, which is W—NH(CH$_2$)$_3$CH$_2$—;
wherein the W group is CH$_3$O(CH$_2$CH$_2$O)CH$_2$CH$_2$—.

15. The compound, or the stereoisomer, the crystalline polymorph, the solvate, the prodrug or the pharmaceutically acceptable salt or ester thereof, according to claim 9, wherein
R$^1$ is

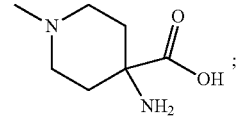

R$_d$ is selected from group consisting of: H$_2$NCH$_2$—, H$_2$NCH$_2$CH$_2$—, H$_2$N(CH$_2$)$_2$CH$_2$—, H$_2$N(CH$_2$)$_3$CH$_2$—, H$_2$N(CH$_2$)$_4$CH$_2$—, H$_2$N(CH$_2$)$_5$CH$_2$—, H$_2$NC(=NH)CH$_2$—, H$_2$NC(=NH)NHCH$_2$—, H$_2$NC(=NH)NHCH$_2$CH$_2$—, H$_2$NC(=NH)NH(CH$_2$)$_2$CH$_2$—, and H$_2$NC(=NH)NH(CH$_2$)$_3$CH$_2$—; wherein R$_d$ is optionally substituted with one or more H or C$_{1-4}$alkyl;
wherein substitution of R$_d$ with one W group forms a group, which is R$^3$O(CH$_2$CH$_2$O)$_m$CH$_2$CH$_2$—R$_d$;
R$^3$ is methyl; and
m is 1, 2, or 3.

16. The compound, or the stereoisomer, the crystalline polymorph, the solvate, the prodrug or the pharmaceutically acceptable salt or ester thereof, according to claim 9, wherein
R$^1$ is

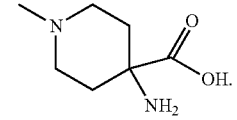

17. A pharmaceutical composition, comprising a therapeutically effective amount of the compound according to claim 2 and one or more pharmaceutically acceptable carriers.

18. The pharmaceutical composition according to claim 17, wherein the pharmaceutical composition is administered orally, intravenously, intraarterially, subcutaneously, intraperitoneally, intramuscularly or transdermally.

19. A pharmaceutical composition, comprising a therapeutically effective amount of the compound according to claim 9 and one or more pharmaceutically acceptable carriers.

20. The pharmaceutical composition according to claim 19, wherein the pharmaceutical composition is administered orally, intravenously, intraarterially, subcutaneously, intraperitoneally, intramuscularly or transdermally.

21. A pharmaceutical composition, comprising a therapeutically effective amount of the compound according to claim 4 and one or more pharmaceutically acceptable carriers.

22. The pharmaceutical composition according to claim 21, wherein the pharmaceutical composition is administered orally, intravenously, intraarterially, subcutaneously, intraperitoneally, intramuscularly or transdermally.

23. The compound of claim 1, or the stereoisomer, the crystalline polymorph, the solvate, the prodrug or the pharrmaceutically acceptable salt or ester thereof, wherein $R^1$ is

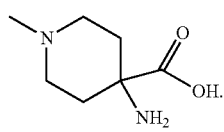

24. The compound of claim 23, or the stereoisomer, the crystalline polymorph, the solvate, the prodrug or the pharmaceutically acceptable salt or ester thereof, wherein the compound is selected from the group consisting of:
  4-amino-1-((R)-2-((R)-2-((R)-2-((R)-2-amino-3-phenylpropanamido)-3-phenylpropanamido)-4-methylpentanamido)-6-((2-aminoethyl)amino)hexanoyl)piperidin-4-carboxylic acid;
  4-amino-1-((R)-2-((R)-2-((R)-2-((R)-2-amino-3-phenylpropanamido)-3-phenylpropanamido)-4-methylpentanamido)-6-((3-aminopropyl)amino)hexanoyl)piperidin-4-carboxylic acid;
  4-amino-1-((R)-2-((R)-2-((R)-2-((R)-2-amino-3-phenylpropanamido)-3-phenylpropanamido)-4-methylpentanamido)-6-((2-(2-methoxyethoxy)ethyl)amino)hexanoyl)piperidin-4-carboxylic acid; and
  4-amino-1-((R)-28-((R)-2-((R)-2-((R)-2-amino-3-phenylpropanamido)-3-phenylpropanamido)-4-methylpentanamido)-2,5,8,11,14,17,20-heptaoxa-23-azanonacosan-29-oyl)piperidin-4-carboxylic acid.

25. A pharmaceutical composition, comprising a therapeutically effective amount of the compound according to claim 24 and one or more pharmaceutically acceptable carriers.

26. A method for preparing the compound of claim 1, or the stereoisomer, the crystalline polymorph, the solvate, the prodrug or the pharmaceutically acceptable salt or ester thereof, wherein $R_d$ is $H_2N(CH_2)_3CH_2$— and is substituted with one or two W groups, comprising:
  obtaining a compound of formula i-2 from a compound of formula i-1 by a condensation reaction with an α-amino ester, wherein the compound of formula i-1 and the compound of formula i-2 are:

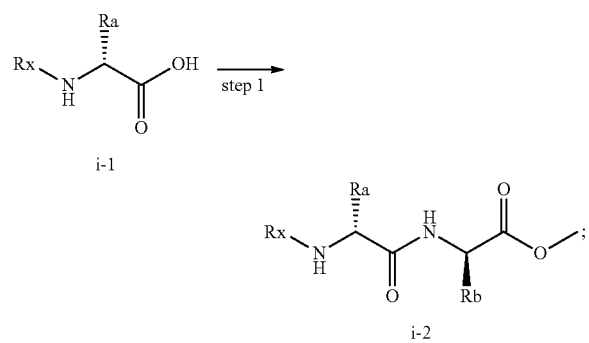

obtaining a compound of formula i-3 from the compound of formula i-2 by a hydrolysis reaction and a condensation reaction, wherein the compound of formula i-3 is:

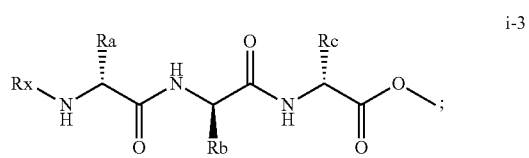

obtaining a compound of formula i-4 from the compound of formula i-3 by a hydrolysis reaction and a condensation reaction, wherein the compound of formula i-4 is:

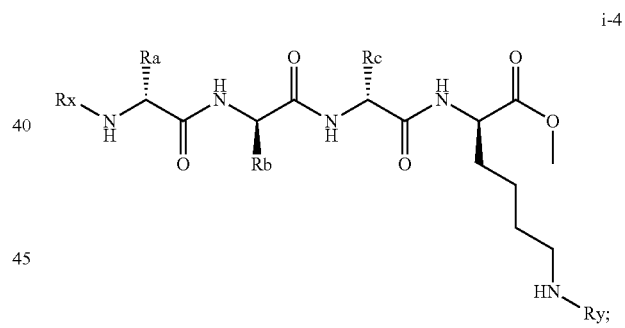

obtaining a compound of formula i-5 from the compound of formula i-4 by a hydrolysis reaction and a condensation reaction, wherein the compound of formula i-5 is:

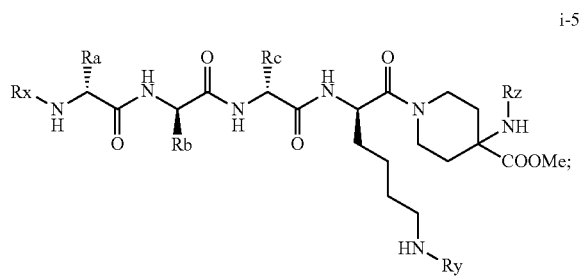

removing Ry from the compound of formula i-5 and introducing one or two W groups to produce a compound of formula i-6, wherein the compound of formula i-6 is:

i-6

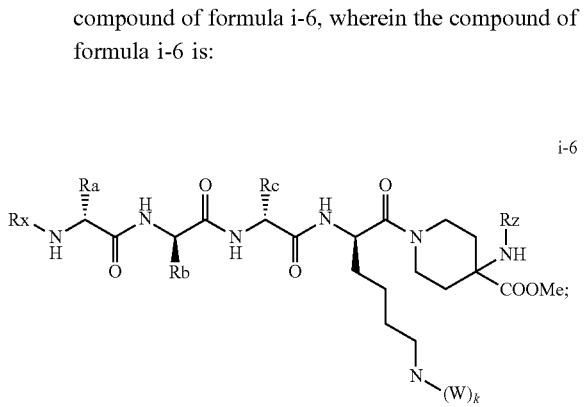

and obtaining compound of formula i-7 from the compound of formula i-6 by a hydrolysis reaction and a deprotection reaction, wherein the compound of formula i-7 is:

i-7 or obtaining a compound of formula iv-1 from the compound of formula i-3 by a hydrolysis reaction and a condensation reaction, wherein the compound of formula iv-1 is:

iv-1 obtaining a compound of formula iv-2 from the compound of formula iv-1 by a hydrolysis reaction and a condensation reaction, wherein the compound of formula iv-2 is:

iv-2 and obtaining a compound of formula iv-3 from the compound of formula iv-2 by a deprotection reaction, wherein the compound of formula iv-3 is:

iv-3 wherein Rx, Ry, and Rz, are independently amino-protecting groups, k is 1 or 2; and $R^1$, $R_a$, $R_b$, and $R_c$ are as defined in claim 1.

27. A method for treating a disease associated with κ-opioid receptor, comprising administering to a subject having a disease associated with κ-opioid receptor an effective amount of the compound, or the stereoisomer, the crystalline polymorph, the solvate, the prodrug or the pharmaceutically acceptable salt or ester thereof, according to claim 1 or a pharmaceutical composition comprising a therapeutically effective amount of the compound according to claim 1 and one or more pharmaceutically acceptable carriers, wherein, the disease associated with κ-opioid receptor is selected from the group consisting of pain, inflammation, itching, edema, hyponatremia, hypopotassaemia, intestinal obstruction, cough and glaucoma.

28. A method for enhancing the level or activity of κ-opioid receptor in a cell, comprising administering to the cell an effective amount of the compound, or the stereoisomer, the crystalline polymorph, the solvate, the prodrug or the pharmaceutically acceptable salt or ester thereof according to claim 1, or a pharmaceutical composition comprising a therapeutically effective amount of the compound according to claim 1 and one or more pharmaceutically acceptable carriers.

29. The method according to claim 27, wherein the pain is selected from the group consisting of neuropathic pain, somatic pain, visceral pain and skin pain.

30. The method according to claim 27, wherein the pain is selected from the group consisting of arthritis pain, nephrolith pain, hysterotrismus, dysmenorrhea, endometriosis, post-surgical pain, pain after medical treatment, eye pain, otitis pain, cancer pain and pain associated with gastrointestinal dysfunction.

31. A method for treating a disease associated with κ-opioid receptor, comprising administering to a subject having a disease associated with κ-opioid receptor an effective amount of the compound, or the stereoisomer, the crystalline polymorph, the solvate, the prodrug or the pharmaceutically acceptable salt or ester thereof, according to claim 2 or a pharmaceutical composition comprising a therapeutically effective amount of the compound according to claim 2 and one or more pharmaceutically acceptable carriers, wherein, the disease associated with κ-opioid receptor is selected from the group consisting of pain, inflammation, itching, edema, hyponatremia, hypopotassaemia, intestinal obstruction, cough and glaucoma.

32. A method for enhancing the level or activity of κ-opioid receptor in a cell, comprising administering to the cell an effective amount of the compound, or the stereoisomer, the crystalline polymorph, the solvate, the prodrug or the pharmaceutically acceptable salt or ester thereof, according to claim 2, or a pharmaceutical composition comprising a therapeutically effective amount of the compound according to claim 2 and one or more pharmaceutically acceptable carriers.

33. The method according to claim 31, wherein the pain is selected from the group consisting of neuropathic pain, somatic pain, visceral pain and skin pain.

34. The method according to claim 31, wherein the pain is selected from the group consisting of arthritis pain, nephrolith pain, hysterotrismus, dysmenorrhea, endometriosis, post-surgical pain, pain after medical treatment, eye pain, otitis pain, cancer pain and pain associated with gastrointestinal dysfunction.

35. A method for treating a disease associated with κ-opioid receptor, comprising administering to a subject having a disease associated with κ-opioid receptor an effective amount of the compound, or the stereoisomer, the crystalline polymorph, the solvate, the prodrug or the pharmaceutically acceptable salt or ester thereof, according to claim 9 or a pharmaceutical composition comprising a therapeutically effective amount of the compound according to claim 9 and one or more pharmaceutically acceptable carriers, wherein, the disease associated with κ-opioid receptor is selected from the group consisting of pain, inflammation, itching, edema, hyponatremia, hypopotassaemia, intestinal obstruction, cough and glaucoma.

36. A method for enhancing the level or activity of κ-opioid receptor in a cell, comprising administering to the cell an effective amount of the compound, or the stereoisomer, the crystalline polymorph, the solvate, the prodrug or the pharmaceutically acceptable salt or ester thereof according to claim 9, or a pharmaceutical composition comprising a therapeutically effective amount of the compound according to claim 9 and one or more pharmaceutically acceptable carriers.

37. The method according to claim 35, wherein the pain is selected from the group consisting of neuropathic pain, somatic pain, visceral pain and skin pain.

38. The method according to claim 35, wherein the pain is selected from the group consisting of arthritis pain, nephrolith pain, hysterotrismus, dysmenorrhea, endometriosis, post-surgical pain, pain after medical treatment, eye pain, otitis pain, cancer pain and pain associated with gastrointestinal dysfunction.

39. A method for treating a disease associated with κ-opioid receptor, comprising administering to a subject having a disease associated with κ-opioid receptor an effective amount of the compound, or the stereoisomer, the crystalline polymorph, the solvate, the prodrug or the pharmaceutically acceptable salt or ester thereof, according to claim 4 or a pharmaceutical composition comprising a therapeutically effective amount of the compound according to claim 4 and one or more pharmaceutically acceptable carriers, wherein, the disease associated with κ-opioid receptor is selected from the group consisting of pain, inflammation, itching, edema, hyponatremia, hypopotassaemia, intestinal obstruction, cough and glaucoma.

40. A method for enhancing the level or activity of κ-opioid receptor in a cell, comprising administering to the cell an effective amount of the compound, or the stereoisomer, the crystalline polymorph, the solvate, the prodrug or the pharmaceutically acceptable salt or ester thereof, according to claim 4, or a pharmaceutical composition comprising a therapeutically effective amount of the compound according to claim 4 and one or more pharmaceutically acceptable carriers.

41. The method according to claim 39, wherein the pain is selected from the group consisting of neuropathic pain, somatic pain, visceral pain and skin pain.

42. The method according to claim 39, wherein the pain is selected from the group consisting of arthritis pain, nephrolith pain, hysterotrismus, dysmenorrhea, endometriosis, post-surgical pain, pain after medical treatment, eye pain, otitis pain, cancer pain and pain associated with gastrointestinal dysfunction.

\* \* \* \* \*